(12) United States Patent
Wikberg et al.

(10) Patent No.: US 9,403,841 B2
(45) Date of Patent: Aug. 2, 2016

(54) PHRAGAMALIN LIMONOIDS FOR THE TREATMENT OF SEXUAL DYSFUNCTION

(71) Applicant: DICOTYLEDON AB, Sigtuna (SE)

(72) Inventors: Jarl Wikberg, Sigtuna (SE); Aigars Jirgensons, Riga (LV); Edvards Liepinsh, Riga (LV)

(73) Assignee: DICOTYLEDON AB, Sigtuna (SE)

( * ) Notice: Subject to any disclaimer, the term of this patent is extended or adjusted under 35 U.S.C. 154(b) by 0 days.

(21) Appl. No.: 14/374,356

(22) PCT Filed: Jan. 25, 2013

(86) PCT No.: PCT/EP2013/051413
§ 371 (c)(1),
(2) Date: Jul. 24, 2014

(87) PCT Pub. No.: WO2013/110744
PCT Pub. Date: Aug. 1, 2013

(65) Prior Publication Data
US 2015/0011616 A1     Jan. 8, 2015

(30) Foreign Application Priority Data

Jan. 25, 2012 (SE) ..................................... 1200052
Nov. 6, 2012 (SE) ..................................... 1200678
Jan. 4, 2013 (SE) ..................................... 1300011

(51) Int. Cl.
*C07D 493/22* (2006.01)
*C07D 493/18* (2006.01)

(52) U.S. Cl.
CPC ............ *C07D 493/22* (2013.01); *C07D 493/18* (2013.01)

(58) Field of Classification Search
CPC .......................... C07D 493/18; C07D 493/22
USPC .......................................... 514/450; 549/275
See application file for complete search history.

(56) References Cited

U.S. PATENT DOCUMENTS

2003/0180395 A1    9/2003    Bueter

FOREIGN PATENT DOCUMENTS

| JP | 2005-213202 | 8/2005 |
| WO | WO 2007/031830 | 3/2007 |
| WO | WO 2008/145996 | 12/2008 |

OTHER PUBLICATIONS

Abdelgaleil, S.A.M. et al., "Antifeeding activity of limonoids from *Khaua senegalesis* (Meliaceae)," J. Appl. Ent., 2003, 127:236-239.
Andersson, K.-E., "Pharmacology of Penile Erection," Pharmacological Reviews, 2001, 53(3):417-450.
Ansel et al., "Pharmaceutical Dosage Forms and Drug Delivery Systems," Seventh Edition, 1999, ISBN 0-683-30572-7.
Arndt et al., "The Structure of Phragmalin a Meliacin with a Norbornane Part Skeleton," Tetrahedron, 1972, 28:2333-2340.
Baldwin, "Sexual dysfunction associated with antidepressant drugs," Expert Opinion Drug Safety, 2004, 3(5):457-470.
Basson, R., "Female Sexual Response: The Role of Drugs in the Management of Sexual Dysfunction," Gynecol., 2001, 98(2):350-353.
Berge et al., "Pharmaceutical Salts," J. Pharm. Sci., 1977, 66:1-19.
Bernasconi et al., "Nucleophilic Addition to Olefins. $5_1$ Reaction of 1,1-Dinitro-2,2diphenylethylene with Water and Hydroxide Ion in 50% $Me_2SO$-50% Water. Complete Kinetic Analysis of Hydrolytic Cleavage of the C=C Double Bond in Acidic and Basic Solution," J. Am. Chem. Soc., 1981, 103 (16):4850-4860.
Bolour et al., "Testoterone therapy in women: a review," International Journal of Impotence Research, 2005, 17:399-408.
Boto, A. et al., "Hypervalent iodine reagents: Synthesis of a steroidal orthoacetate by a radical reaction," Tetrahedron Letters, 1994, 35(37):6933-6936.
Cappelleri et al., "The Sexual Health Inventory for Men (SHIM): a 5-year review of research and clinical experience," International Journal of Impotence Research, 2005, 17:307-319.
Carré, A., "Polar Interactions at liquid/polymer interfaces," J. Adhesion Sci. Technol., 2007, vol. 21, No. 10, pp. 961-981.
Charman et al., "Self-Emulsifying drug Delivery Systems: Formulation and Biopharmaceutic Evaluation of an Investional Lipophilic Compound," Pharmaceutical Research, 1992, 9(1):87-93.
Chen et al., "Phragmalin Limonoids from *Chukrasia tabularis* var. *velutina*," Planta Medica, 2012, vol. 78, No. 03, pp. 286-290.
Coombes et al., "Phragmalin limonoids from the Madagascan Meliaceae Neobeguea leandreana," Journal of Natural Products, 2003, vol. 66, No. 6, pp. 735-738.
Dálaigh et al., "Asymmetric acyl-transfer promoted by readily assembled chiral 4-N,N-dialkylaminopyridine derivates," Org. Biomol. Chem., 2006, 4:2785-2793.
Davis, S. R. et al., "Circulating Androgen Levels and Self-reported Sexual Function in Women," JAMA, 2005, 294(1):91-96.
Dess et al., "A Useful 12-I-5 Triacetoxyperiodinane (the Dess-Martin Periodinane) for the Selective Oxidation of Primary or Secondary Alcohols and a Variety of Related 12-I5 Species$^{Ia}$," J. Am. Chem. Soc., 1991, 113:7277-7287.
Enserink et al., "Let's Talk About Sex—and Drugs," Science, 2005, 308:1578-1580.
Gasteiger et al., "Chemoinformatics" 2003, ISBN 3-527-30681-1.
Gebauer et al., "A Short and Enantiospecific Synthesis of (-)-Nuphatamine," Synlett, 2005, 18:2826-2828.
Giuliano et al., "Neural control of erection," Physiology & Behavior, 2004, 83:189-201.

(Continued)

*Primary Examiner* — Taofiq A Solola
(74) *Attorney, Agent, or Firm* — Michael Best & Friedrich LLP

(57) ABSTRACT

The present invention relates to novel chemical compounds, to methods for synthesis of such compounds, and to the use of these novel compounds in the synthesis of other chemical compounds that, inter alia, may be used in the treatment of sexual dysfunction, and for eliciting enhancing effects on sexual behavior. The invention also relates to remarkable biological properties of the novel compounds in their capacity of inducing aggressive behavior.

1 Claim, 6 Drawing Sheets

(56) References Cited

OTHER PUBLICATIONS

Figure 1:
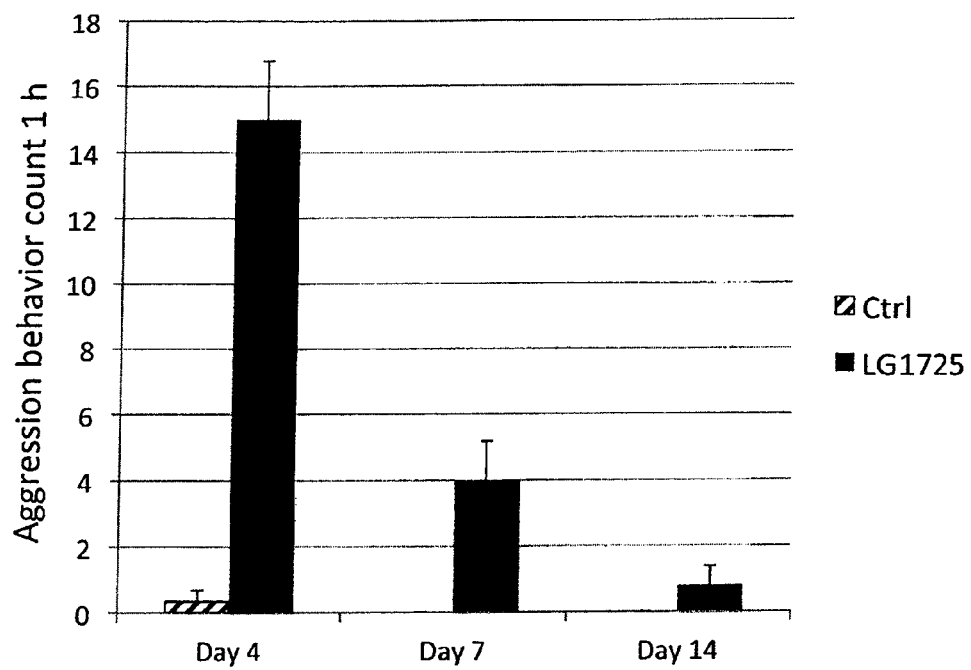

Grumbach et al., "Hydrophilic Interaction Chromatography Using Silica Columns for the Retention of Polar Analytes and Enhanced ESI-MS Sensitivity," LCGS Asia Pacific, 2004, 7(4):38-44.
Hafez et al., "Erectile Dysfuntion: Anatomical Parameters, Etiology, Diagnosis and Therapy," Archives of Andrology, 2005, 51:15-31.
Hoshino et al., Database WPI Week 200555 Thomson Scientific, London, GB, AN 2005-537835 XP002538721.
International Search Report and Written Opinion for Application No. PCT/EP2013/051413 dated Sep. 12, 2013 (20 pages).
Kendirci, M. et al., "The Impact of Vascular Risk Factors on Erectile Function," Drugs of Today, 2005, 41(1):65-74.
Kipassa, N.T., PhD thesis, Kagoshima University, Mar. 2008: Structural studies of tetranortriterpenoids from the Congolese species of *Entandrophragma angolense*; and efficient short step synthesis of Corey's Tamiflu intermediate.
Kotsos, M.P., MSc thesis, University of Natal, 1997: Extractives from Neobeguea mahafalensis and Cedrelopsis grevei.
Krauss et al., "A New Approach Towards (±)-4-Ipomeanol and its 2-Furyl Regioisomer," Turkish J Chemistry, 2005, 29(6):635-639.
Li et al., "Two new limonoids from the stem barks of *Chukrasia tabularis* var. *velutina*," Journal of Asian Natural Products Research, 2011, 13(9):781-786.
Liao et al., "Plant orthoesters," Chemical Reviews, 2009, vol. 109, No. 3, 1092-1140.
Liu et al., "Kv1.2 potassium channel inhibitors from *Chukrasia tabularis*," Organic & Biomolecular Chemistry, 2012, vol. 10, No. 7, p. 1448-1458.
Luo et al., "Chukvelutilides A-F, phragmalin limonoids from the stem barks of *Chukrasia tabularis* var. *velutina*," Thetrahedron, 2009, vol. 65, No. 17, pp. 3425-3431.
Luo et al., "D-Ring-Opened Phragmalin-Type Limonoids from *Chukrasia tabularis* var. *velutina*," Chemistry & Biodiversity, 2011, vol. 8, No. 12, pp. 2261-2269.
Luo et al., "Two new C-15 enolic acyl phragmalin-type limonoids from *Chukrasia tabularis* var. *velutina*," Natural Product Research, 2011, 27(7):597-602.
Mackay et al., "Enantioselective Acylation Using a Second-Genaration P-Aryl-2-phosphabicyclo[3.3.0]octane Catalyst," J. Org. Chem. (2004) 69:6934-6937.
Mansoori et al., "Bioseparation, Using Supercritical Fluid Extraction/Retrograde Condensation," Bio/Technology, 1988, 6:393-396.
Master et al., "Synthesis of Low Molecular Weight Compounds with Complement Inhibition Activity," Bioorganic & Medicinal Chemistry Letters, 2003, 13:1249-1251.
Meuleman et al., "Hypoactive sexual desire disorder: an understimated condition in men," BJU International, 2005, 95:291-296.
Miller et al., "Total Synthesis of (−)-Heptemerone B and (−)-Guanacastepene E," J. Am. Chem. Soc., 2006, 128 (51): 17057-17062.
Muellner et al., "Molecular Phylogenetics of Meliaceae (Sapindales) Based on Nuclear and Plastid DNA Sequences," Am. J. Bot., 2003, 90(3):471-80.
Mulholland et al., "Limonoid Extractives from the Genera *Capuronianthus neobeguea* and *Quivisianthe*," Phytochemistry, 1988, 27(6):1741-1743.
Mulholland, S.A. et al., "The chemistry of the Meliaceae and Ptaeroxylaceae of Southern and Eastern Africa and Madagascar," Current Organic Chemistry, 2000, 4:1011-1054.
Naidoo et al., "Limonoids and triterpenoids from the seed of *Neobeguea mahafalensis*," Biochemical Systematics and Ecology, 2003, 31(9):1047-1050.
Neises et al., "Simple Method for the Esterification of Carboxylic Acids[1 1]," Angew. Chem. Int. Ed., 1978, 17:522-523.
Ouk et al., "Dimethyl carbonate and phenols to alkyl aryl ethers via clean synthesis," Green Chemistry, 2000, 4:431-435.

Paris, R.R. et al., "On the polyphenols (phenolic acids, flavonoids) in leaves of 2 Meliaceae species of *Madagascar cedrelopsis-grevei* and *Neobeguea-mahafalensis*," Plantes Medicinales et Phytotherapies, 1972, 6(4):311-319. Ebstract translation attached.
Ralph et al., "Ejaculatory disorders and sexual function," BJU International, 2005, 95(9):1181-1186.
Randrianarivelojosia et al., "A Limonoid from *Neobeguea mahafelensis*," Phytochemistry, 1999, 52(6):1141-1143.
Rasoanaivo et al., "Medical plants used to treat malaria in Madagascar," Journal of Ethnopharmacology, 1992, 37:117-127.
Rasoanaivo et al., "Screening Extracts of Madagascan Plants in Search of Antiplasmodial Compounds," Phytotherapy Research (2004) 18, 742-747.
Rosen et al., "The International Index of Erectile Function (IIEF): A Multidimensional Scale for Assessment of Erectile Dysfunction," Urology, 1997, 49(6):822-30.
Ruiz-Jimenez et al., "Forward-and-back dynamic ultrasound-assisted extraction of fat bakery products," Anal Chim Acta, 2004, 502:75-82.
Ruiz-Jimenez et al., "Use of chemometrics and mid infrared spectroscopy for the selection of extraction alternatives to reference analytical methods for total fat isolation," Analytica Chimica Acta, 2004, 525:159-169.
Sandroni, P., "Aphrodisiacs past and present: a historical review," Clinical Autonomic Research 2001, 11:303-307.
Shabbir, M. et al., "Erectile dysfuntion: an underdiagnosed condition associated with multiple risk factors," Current Medical Research and Opinion, 2004, 20(5):603-606.
Tamburlin-Thumin et al., "Synthesis and biological evaluation of O-alkylated tropolones and related α-ketohydroxy derivates as ribonucleotide reductase inhibitors," Eur. J. Med. Chem., 2001, 36:561-568.
Von Soxhlet, F., "Dinglers Polytechnisches Journal," 1879, 232:461-5 (translation of abstract attached).
Yang et al., "Comparison of the International Index of Erectile Function erectile domain scores and nocturnal penile tumescence and rigidity measurements: does one predict the other?," BJU Int., 2006, 98(1):105-9.
Berge et al., "Resveratrol inhibits benzo[a]pyrene-DNA adduct formation in human bronchial epithelial cells," British Journal of Cancer, 2004, 91, 333-338.
Blay, G. et al., "A Non-Catalyzed Ring-Opening Aminolysis Reaction of Sequiterpene Lactone," Tetrahedron Letters, 1994, vol. 35, No. 6, pp. 931-934.
Bloomfield, J.J. et al., "Control of lithium aluminum hydrige reduction of cyclic dicarboxylic acid anhydrides to produce y-lactose or diols," Journal of Organic Chemistry, 1967, 32, 3919-24.
Brown, D.A. et al., "Carbon-13 nuclear magnetic resonance spectra of limonoids. Part IV. Extractives from Chukrasia tabularis A. Juss," J. Chem. Res., Synopses, 1978, 1, 20.
Chen, F.F. et al., "Mixed anhydrides in peptide synthesis. A study of urethane formation with a contribution on minimization of racemization," Can. J. Chem., 1987, 65, 613.
Chernega, A.N. et al., "The Chiral Auxiliary N-1-(1'-Naphthyl)ethyl-O-tert-butylhydroxylamine: A Chiral Weinreb Amide Equivalent," Organic Letters, 2009, 11(15), 3254-3257.
Colobert et al., "First Enantioselective Total Synthesis of (−)-Centrolobine," Organic Letters, 2002, vol. 4, No. 10, 1723-1725.
Connolly, J. et al., "Spicatin, a protolimonoid from Entandrophragma spicatum," Phytochemistry, 1981, 20(11), 2596-7.
Connolly, J.D. et al., "Limonoids from *Xylocarpus moluccensis* (Lam.) M. Roem," J. Chem. Soc., Perkin Trans. 1, 1976, 9, 1993-1996.
Connolly, J.D. et al., "Tetra-nortriterpenoids from the Seeds of *Chukrasia fabularis* (Meliaceae); Simple Esters of Phragmalin and 12α-Acetoxyphragmalin," J. Chem. Soc., Perkin Trans 1, 1978, 3, 285-288.
Cui, J. et al., "Xylocarpins A-I, Limonoids from the Chinese Mangrove Plant *Xylocarpus granatum*," J. Nat. Prod., 2007, 70, 772-778.
De Almeida et al., "Escalated aggressive behavior: Dopamine, serotonin and GABA," European Journal Pharmacology, 2005, 256, 51-64.

(56) References Cited

OTHER PUBLICATIONS

De Boer et al., "5-HT1A and 5-HT-1B receptor agonist and aggression: A pharmacological challenge of the serotonin deficiency hypothesis," European Journal of Pharmacology, 2005, 526, 125-139.
Dineen, T.A. et al., "Efficient Transamidation of Primary Carboxamides by in Situ Activation with N,N-Dialkylformamide Dimethyl Acetals," J. Am. Chem. Soc., 2006, 128, 16406-16409.
Ekong et al., "Novel meliacins (limonoids) from the wood of Pceucedrela kotschyii," Tetrahedron Lett., 1967, 8(36), 3525-3527.
Greene, T.W. & Wuts, P.GM., Protective Groups in Organic Synthesis, 3rd ed., John Wiley & Sons: New York, 1999.
Guex et al., "Die Busseine C, D, E, F, G, H, J, K, L and M, zehn neue Tetranortriterpene aus Entandrophragma bussei Harms," Helvetica Chimica Acta, 1984, vol. 67, Fasc. 3, Nr. 99, 885-901.
Guex et al., "Selective reactions of the tetranortriterpenes busseins A and B," Helvetica Chimica Acta, 1985, 68, 522-33.
Hay et al., "Limonoid Orthoacetates and Antiprotozoal Compounds from the Roots of Pseudocedrela kotschyii," J. Nat. Prod., 2007, 70, 9-13.
Hirner et al., "Synthesis of α-Amino Amides via N,O-Acetals Derived from Weinreb Amides," J. Org. Chem., 2009, 74, 7798-7803.
Jacobi et al., "Bis heteroannulation. 8. Total synthesis of (+)-paniculide-A," Tetrahedron Lett., 1984, 25(42), 4859-4862.
Jaipuri et al., "Microwave-assisted cleavage of Weinreb amide for carboxylate protection in the synthesis of a (R)-3-hydroxyalkanoic acid," Tetrahedron Letters, 2004, 45, 4149-4152.
Kocienski, P.J., Protecting Groups, 3rd ed., Georg Thieme Verlag: New York, 2005, selected pages.
Labeeuw et al., "Synthesis of modified Weinreb amides N-tert-butoxy-N-methylamides as effective acylating agents," Tetrahedron Letters, 2004, 45, 7107-7110.
Lebold et al., "Synthesis of the bridging framework of phragmaline-type limonoids," 2012, 14(8), 2110-2113.
Lin et al., "D-Ring-Opened Phragmalin-Type Limonoid Otrhoesters from the Twigs of Swietenia macrophylla," J. Nat. Prod., 2009, 72(7), 1305-1313.
Liu et al., "A mild method for ring-opening aminolysis of lactones," Tetrahedron Lett., 2001, 42, 2439-2441.
Macphillamy, "Plant Science Bulletin," Botanical Society of America, 1963, vol. 9, Issue 2, 15 pages.
Miczek et al., "Neurobiological Mechanisms Controlling Aggression: Preclinical Developments for Pharmacotherapeutic Interventions," Neurosci. Biobehav. Rev., 1994, 18(1):97-110.
Nahm et al., "N-methoxy-N-methylamides as effective acylating agents," Tetrahedron Lett., 1981, 22(39), 3815-3818.
Nakatani et al., "Phragmalin limonoids from Chukrasia tabularis," Phytochemistry 65, 2004, 2833-2841.
Narender et al., "13C NMR spectroscopy of D and B, D-ring seco-limonoids of Meliaceae family," Natural Product Research, 2008, 22(9), 763-800.
Niu et al., "A Powerful Reagent for Synthesis of Weinreb Amides Directly from Carboxylic Acids," Organic Letters, 2009, vol. 11, No. 19, 4474-4477.
Niven et al., "Revision of the structure of the limonoid pseudrelone B from pseudocedrela kotschyii," Phytochemistry, 1988, 27, 1542.
Oliver et al., "5-HT1B receptors and aggression: A review," European Journal of Pharmacology, 2005, 526, 207-217.
Pettit et al., "Steroids and related natural products-X. Reduction of lactones," Tetrahedron, 1962, vol. 18, pp. 953-958.
Phillipson, "New Drugs from Nature—It Could be Yew," Phytotherapy Research, 1999, 13, 2-8.
Piaz et al., "Structural characterization of tetranortriterpenes from Pseudrocedrela kotschyi and Trichilia emetica and study of their activity towards the chaperone Hsp90," Phytochemistry, 2012, 75, 78-89.
Ragettli et al., "Die Chukrasine A, B, C, D and E, fünf neue Tetranortriterpene aus Chukrasia tabularis A. Juss," Helvetica Chimica Acta, 1978, 61(5;174), 1814-1831.
Raskin et al., "Can an Apple a Day Keep the Doctor Away?" Current Pharmaceutical Design, 2004, 10, 3419-3429.
Remington's Pharmaceutical Sciences, 18th Edition, 1990, pp. 1435-1451, 1518-1545, 1632-1665.
Revilla et al., "Comparison of Several Procedures Used for the Extraction of Anthocyanins from Red Grapes," J. Agric. Food Chem., 1998, 45, 4592-4597.
Rowe RC et al. Handbook of Pharmaceutical Excipients, 3rd edition, A. Kibbe, Ed., APhA Publications, 6th edition, 2009, ISBN-13: 978-1582120584.
Saad et al., "Swietenialides, novel ring D opened phragmalin limonoid orthoesters from Swietenia mahogani JACQ," Tetrahedron, 2003, 59, 8027-8033.
Salvino et al., "Parallel Syntheis of Aldehydes and Ketone Facilitated by a New Solid-Phase Weinreb Amide," J. Org. Chem., 1999, 64, 1823-1830.
Sarigaputi et al., "Xyloccensin E," Acta Crystallographica, Section E: Structure Reports Online, 2010, E66(6), o1348-o1349.
Seidel, "Initial and Bulk Extraction," Natural Products Isolation, 2006, 2, 27-46.
Sha et al., "Anionic Cyclization Approach toward Perhydrobenzofuranone: Stereocontrolled Synthesis of the Hexahydrobenzofuran Subunit of Avermectin," J. Org. Chem., 2002, 67, 831-836.
Shimizu et al., "Efficient Method for Preparation of N-Methoxy-N-methyl Amides by Reaction of Lactones or Esters with $Me_2AlCl$—MeONHMe.HCl," Tetrahedron Lett., 1997, 38, 2685-2688.
Smith MB and Smith M. Organic Synthesis, 2nd edition, Mcgraw Hill (2001) ISBN-13: 978-0070482425.
Tanaka et al., "Andirolides H-P from the flower of andiroba (*Carapa guianensis*, Meliaceae)," Tetrahedron 68, 2012, 3669-3677.
Taylor, D.A.H., "C Nuclear Magnetic Resonance Spectra of Some Limonoids. The Structure of Procerin, an Extractive from Carapa procera," J. Chem. Soc., 1974, 437-441.
Taylor, D.A.H., "Functional Groups of Bussein," Chemistry & Industry, 1967, 14, 582.
Warren S and Wyatt P. Organic Synthesis—Strategy and Control, Wiley-Blackwell (2007). ISBN: 978-0471489405.
Warren S and Wyatt P. Organic Synthesis: The Disconnection Approach, 2nd edition. Wiley, (2008). ISBN-13: 978-0470712375.
Wikipedia, Bark, <http://en.wikipedia.org/wiki/Bark> Jun. 3, 2005.
Yi et al., "Identifying Lactone Hydrolysis in Pharmaceuticals. A tool for Metabolite Structural Characterization," Anal. Chem., 2005, 77, 6655-6663.
Yu et al., "A novel approach to the preparation of injectable emulsions by a spontaneous emulsification process," International Journal of Pharmaceutics, 1993, 89, 139-146.

PHRAGAMALIN LIMONOIDS FOR THE TREATMENT OF SEXUAL DYSFUNCTION

This application claims the benefit of prior PCT application WO 2008/145996 (Published on 4 Dec. 2008), the contents of which are incorporated herein in their entireties by this reference. (In the case there is any ambiguity in abbreviations, atom numbering (or the like) between the incorporated document and the present patent, the present patent shall take precedence).

FIELD AND BACKGROUND

The present invention relates to novel chemical compounds, to methods for synthesis of such compounds, and to the use of these novel compounds in the synthesis of other chemical compounds that, among other things, can be used in the treatment of sexual dysfunction, and for eliciting enhancing effects on sexual behavior. The invention also relates to remarkable biological properties of the novel compounds in their capacity of inducing aggressive behavior.

The previous application WO 2008/145996 described compounds with sexual enhancing activity having the general structure (1):

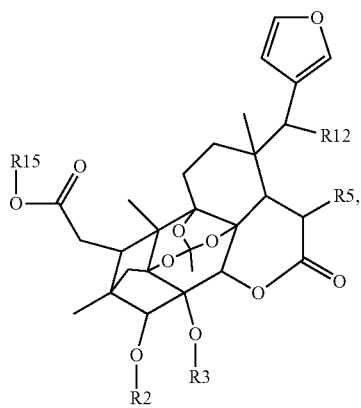

(1)

(i.e. structure III in WO 2008/145969; for substituents see substituents for structure III in WO 2008/145996; note that R15, R5, and R12 in (1) is, respectively, R1, R4 and R5 in WO 2009/145996; note however that for the present patent any reference to substituent or atom numbering does not refer to WO 2009/145996; rather they refer only to the substituent and atom numberings defined herein). WO 2008/145996 claimed the use of compound (1) for the treatment of sexual dysfunctions, such as erectile dysfunction.

However, compounds of structure (1) have hitherto been found only in some plants, and appear there to be rare; only a few representatives of (1) have been found among a few species of the Meliaceae family, where they are present in only small quantities (WO 2008/145996; Luo et al., 2009; see also below). These compounds are therefore difficult and expensive to isolate in any amounts of practical utility, e.g. for use as remedies for treatment of disease.

Working out the full synthesis of a compound according to (1) is a very difficult undertaking indeed, and has not been attempted thus far. However, structures according to the general formula (2a):

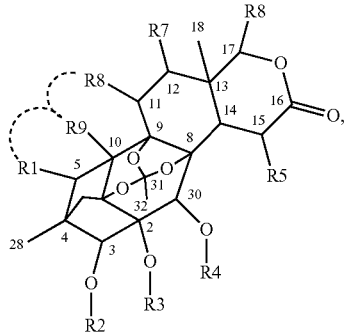

(2a)

wherein, the substituents R1 to R9 vary to a great deal, and where covalent bonds between R1 and R9, and R8 and R9 (marked as hatched lines) (and even between R2 and R3, R3 and R4, and R7 and R8) may or may not be present, are found ubiquitously in nature, where they constitute members of a class of compounds which generally is termed limonoids. Limonoids are particularly found among species of the Meliaceae, often in high quantities in woods, barks or seeds, and methods to isolate them are well known in the art.

Limonoids (2a) include, for example, compounds with the given names xyloccensin E (Connolly et al. 1976; Sarigaputi et al. 2010), xylocarpin I (Cui et al. 2007), kotschyins (Hay et al. 2007), phragmalins (Arndt et al. 1972; Connolly et al. 1978; Nakatani et al. 2004), swietenialides (Saad et al 2003), neobeguins (Randrianarivelojosia et al 1999), pseudrelones (Ekong and Olagbemi, 1967; Mulholland and Taylor 1988; Niven and Taylor 1988), busseins (Guex and Tamm 1984; Taylor 1967), chukrasins (Ragettli et al. 1978; Brown and Taylor 1978), tabulalides (Nakatani et al. 2004). See also Mulholland et al. 2000, and Narender et al. 2008 for compounds included among compounds with structure (2a).

Moreover, among compounds with CAS (Chemical Abstracts Service, at 2540 Olenstangy River Road, Columbus, Ohio 43202, USA) Registry numbers 1299464-67-7, 1267877-55-3, 1248571-24-5, 1219132-70-3, 1214981-83-5, 1214976-20-1, 1186131-42-9, 1126643-44-4, 1126643-43-3, 1126643-42-2, 1053209-52-1, 1045017-87-5, 1038746-45-0, 952615-91-7, 910578-31-3, 803723-28-6, 803723-27-5, 561307-83-3, 260794-07-8, 116408-24-3, 115391-10-1, 115367-50-5, 98401-23-1, 98379-64-7, 98379-62-5, 98379-61-4, 98379-60-3, 98379-59-0, 98379-58-9, 98379-57-8, 96386-37-7, 90955-39-8, 90931-03-6, 90931-02-5, 90931-01-4, 90931-00-3, 90930-99-7, 90930-98-6, 90930-97-5, 90930-96-4, 90930-95-3, 81584-75-0, 67931-05-9, 67931-04-8, 67904-58-9, 67904-57-8, 67904-56-7, 67904-55-6, 67904-54-5, 67904-53-4, 67895-40-3, 67895-39-0, 67895-38-9, 66939-94-4, 66901-32-4, 66901-31-3, 66901-30-2, 66884-81-9, 66884-80-8, 66884-79-5, 66884-78-4, 66884-77-3, 66495-42-9, 66451-22-7, 52724-62-6, 52681-81-9, 41508-26-3, 41060-14-4, 41060-13-3, 40185-37-3, 40185-36-2, 40185-34-0, 40185-33-9, 38575-45-0, 37832-02-3, 37665-93-3, 37665-92-2, 37665-91-1, 37665-90-0, 35183-64-3, 35055-81-3, 939775-81-2, structures of type (2a) are found.

Further more structures according to the general formula (2b) also exist in nature:

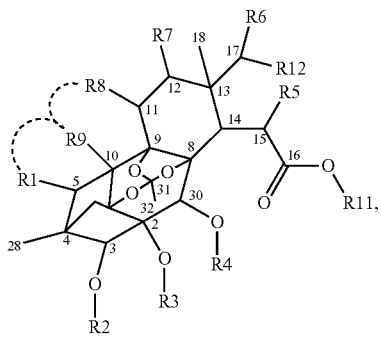

(2b)

wherein in (2b) R12 may often be —O—R10, or oxo, and wherein the substituents R1 to R12 vary to a great deal, and where covalent bonds between R1 and R9, and R8 and R9 (marked as hatched lines in 2a and 2b) (and even between R2 and R3, R3 and R4, and R7 and R8) may or may not be present, where they are also found to some extent among species of the Meliaceae family, albeit generally in comparatively much smaller amounts in the various plant tissues, compared to those for (2a).

Compounds (2b) include the leandreanin A and B, isolated from *Neobeguea leandreana* (Coombes et al.: J Nat Prod. 2003, 66(6):735-8.), kotschyins A, B and C, isolated from *Pseudocedrela kotschyi* (Hay et al.: J Nat Prod. 2007 January; 70(1):9-13.), phragmalin compounds listed as no. 1, 2, 3, 6 and 7 on page 80 in Piaz et al. (Piaz et al.; *Phytochemistry*. 2012, 75:78-89), ring opened phragmalins isolated from *Swietenia macrophyla* (Lin et al. J Nat Prod. 2009, 72(7):1305-13), *Swietenia mahogany* (Saad et al. *Tetrahedron* 2003, 59, 8027-8033) and *Carapa guianensis* (Tanaka et al.: *Tetrahedron* 2012, 68, 3669-3677).

Compounds (2b) also include compounds with CAS Registry numbers 1173892-10-8, 1173892-09-5, 1173892-08-4, 1173892-07-3, 1173892-06-2, 1173892-05-1, 1173892-04-0, 1173892-03-9, 1169770-19-7, 1169770-18-6, 1169770-17-5, 1159493-38-5, 1159493-37-4, 1159493-36-3, 1159493-35-2, 1159493-34-1, 1159493-33-0, 1088920-97-1, 1088920-95-9, 1088920-93-7, 1088920-91-5, 1088920-89-1, 1088920-87-9, 1088920-85-7, 1088920-83-5, 1088920-81-3, 1088920-69-7, 1088920-67-5, 1088920-65-3, 1088920-63-1, 1088920-61-9, 1088920-59-5, 1088920-57-3, 1088920-55-1, 1088920-53-9, 1088920-51-7, 1088920-49-3, 1088920-47-1, 1088920-44-8, 1088920-42-6, 629654-42-8, 629654-41-7, 926896-45-9, 926896-45-9.

(Hereinafter, the structures (2a) and (2b) are collectively referred to as "structure (2)". [Note also that the above numbering of the atoms in the skeleton of compound (2a) and (2b) apply throughout this patent also for the corresponding atoms in anyone of compounds (1), (2aa), (2bb), (3), (3a), (4), (4aa), (4bb), (4cc), (4dd), (4ee), (4ff), (4gg), (4hh), (5) and (5a) (listed compounds defined further below and in the amended claims), phragmalin, or compound with the corresponding phragmalin skeleton of this patent and in WO 2008/145996.]

Therefore, structures (2a) and (2b) confine potential starting materials for affording structure (1) [or for obtaining the even more general structure (5); see below] by semi-synthesis, a field that was the subject of our interest for some time. However, due to the fact that compounds with structure (2b) are less ubiquitous in nature and there known to be available only in only small amounts per weight of plant tissues of distinct species, structure (2b) is not particularly useful for the sake of the present invention, which aims for a highly efficient process for synthesis of compound (1), (5) and (5a). Compounds with structure (2b) [including (2bb)] are therefore for essentially all embodiments of the present invention for practical reasons excluded as starting material for synthesis of a compound (1) [and even for synthesis of (2b), (2bb), (3), (3a), (4), (4aa), (4bb), (4cc), (4dd), (4ee), (4ff), (4gg), (4hh), (5) and (5a); see below] by the process of the invention aiming for high yield synthesis.

However, specifically in synthesis of (1) [and even (5) and (5a)] affording a route for opening the lactone ring in (2a) and closing it into the lactone of (1) proved to be a vast more difficult task than expected and failed using many commonly applied methods for ring opening and closing. This included hydrolytic ring opening of compounds of structure (2a) (e.g. using 0.1 M potassium hydroxide in methanol or 0.1 M sodium hydroxide in water), which were not successful as many side products formed, and the expected carboxylates/their salts could not consistently be demonstrated with NMR analysis. Moreover, adjustment of pH of the reaction mixture led to re-lactonization of the eventually opened lactone ring, providing the starting compound but not the desired products of anyone of structures (1), (5) or (5a). Moreover, the high polarity of carboxylates as the attempted intermediates made monitoring of reactions and isolation of the products difficult, as well as the carboxylate salts formed limited the choice of solvents for oxidation-reactions to afford the most desired oxidation of the hydroxy group at carbon 17 following the ring opening [for atom numbering see structures (2a) and (2b)] prior to closing the lactone in the desired position. Over all these problems rendered the approach of hydrolytic ring opening of a compound (2a) for affording structures (1), (5) and (5a) useless.

Attempts to reductive openings of the lactone ring in compound (2a) were also unsuccessful. Thus, attempts to open the ring in O-protected phragmalins with diisobutylaluminium hydride (DIBAL-H), lithium aluminium hydride (LAH) essentially using procedures as in Bloomfield and Lee, 1967 and Pettit G R et al., 1962, or sodium bis(2-methoxyethoxy) aluminiumhydride (Red-Al) and lithium borohydride ($LiBH_4$) resulted all in complex mixtures (presumably due to stability issues of the ortho-ester functionality), which also rendered these approaches useless.

In addition several attempts on amidolytic ring opening of the lactone in compound (2a) failed. Thus thermal aminolysis with $NH_3$ in methanol at temperatures from 20 to 90° C., essentially using procedures as in Yi et al. 2005, as well as trimethyl aluminium ($Me_3Al$) promoted aminolysis with benzylamine in dichloromethane, essentially using procedures as in Liu et al. 2001, both failed in producing a product with opened ring.

However, this patent solves the problem of opening the lactone ring in a compound of structure (2a) and closing it in another position to provide a compound with structure (1), as well as how to provide a compound with structure (5) and (5a), and the compound of claim 40 [i.e. general structure (III)] in WO 2008/145996. However, the process required surprisingly distinct conditions and distinct reagents to proceed at all, while other closely similar conditions to the successful one led to the excessive formation non-desired side products without formation of any desired product at all. Accordingly the narrow range of suited conditions were indeed not foreseeable by prior art, but are disclosed in this patent. On top of this, for the most preferred embodiments of the invention [i.e. in particular those embodiments which used the most desired starting materials with structure (2a) to yield the most desired end products with structures (1), (5) and (5a)], the patent provides solutions for achieving a)

chemoselectivity and regioselectivity between chemically similar groups (e.g. lactone versus ester in formation of the specific Weinreb amide required in the process), b) regioselectivity between two or three secondary hydroxy groups for affording desired chemical reactions required in the process, and c) the appropriate protection of chemical groups to avoid unwarranted side reactions, all parts, a), b) and c), which were necessary and achieved by the processes of the invention in a surprising way (on top of the above mentioned surprisingly distinct conditions and distinct reagents required for the process to proceed at all) that would be impossible to foresee from prior art by anyone skilled in the art.

On top of this the patent provides a highly efficient process for the manufacture of a compound with structure (5), (5a), (1) or the compound of claim 40 [i.e. general structure (III)] in WO 2008/145996, from raw-materials which are possible to afford in large quantities; the disclosed process being markedly more efficient (i.e. in terms of yield of starting material) than any earlier reported processes for the provision of such compounds.

On top this, the process of this patent provides a direct way to afford a compound of structure (2b) from a compound of structure (2a). This is also a highly important embodiment of the invention, as compounds of structure (2b) have industrial and medical applicability; the unity inventive steps for this aspect of the invention being the same as for converting the compound (2a) or (2b) to a compound with structure (1), (5) and (5a).

On top of this, this patent provides a novel compound (3) [including the more specific structures (3a), (4), (4aa), (4bb), (4cc), (4dd), (4ee), (4ff), (4gg) and (4hh) confined in (3)], including an efficient process to obtain these compounds in high yield, which is in fact the key inventive step in the processes disclosed herein for synthesis of compound (5) [including synthesis of the more specific structure (1) and (5a) confined in (5) and those of claim 40 in WO 2008/145996 also confined in (5)], as well as in synthesis of (2b). Moreover on top of this compound (3) was totally unexpectedly and extremely surprising found to induce marked aggressive behavior when administered to a mammal, a feature that renders compound (3) further highly useful; all aspects and uses of compound (3) are disclosed herein.

DEFINITIONS

Unless otherwise stated, the term "alkyl" refers to an unbranched or branched, cyclic, saturated or unsaturated (so forming, for example, an alkenyl or alkynyl) hydrocarbyl radical, which may be substituted or unsubstituted (with, for example, one or more halogen atoms). Where the term "alkyl" refers to an acyclic group, it is preferably C1-10 alkyl and, more preferably, C1-6 alkyl (such as ethyl, propyl, (e.g. n-propyl or isopropyl), butyl (e.g. branched or unbranched butyl), pentyl or, more preferably, methyl). Where the term "alkyl" is a cyclic group (which may be where the group "cycloalkyl" is specified), it is preferably C3-12 cycloalkyl and, more preferably, C5-10 (e.g. C5-7) cycloalkyl.

When used herein, the term "alkylene" refers to C1-10 (e.g. C1-6) alkylene and, preferably C1-3 alkylene, such as pentylene, butylene (branched or unbranched), preferably, propylene (n-propylene or isopropylene), ethylene or, more preferably, methylene (i.e. —$CH_2$—).

The term "halogen", when used herein, includes fluorine, chlorine, bromine and iodine.

The term "halogeno", when used herein, includes fluorine, chlorine, bromine and iodine as substituent.

The term "heavy atom", when used herein, includes an atom which atomic weight is at least 6.9, i.e. lithium and any atom heavier than lithium. Preferred heavy atoms are nitrogen, oxygen, sulfur, phosphorous and halogen.

The term "aryl" when used herein includes C6-14 [such as C6-13 (e.g. C6-10)] aryl groups. Such groups may be monocyclic, bicyclic or tricyclic and have between 6 and 14 ring carbon atoms, in which at least one ring is aromatic. The point of attachment of aryl groups may be via any atom of the ring system. However, when aryl groups are bicyclic or tricyclic, they are linked to the rest of the molecule via an aromatic ring. C6-14 aryl groups include phenyl, naphthyl and the like, such as 1,2,3,4-tetrahydronaphthyl, indanyl, indenyl and fluorenyl. Most preferred aryl groups include phenyl.

The term "heteroaryl" when used herein refers to an aromatic group containing one or more heteroatom(s) (e.g. one to four heteroatoms) preferably selected from N, O and S (so forming, for example, a mono-, bi-, or tricyclic heteroaromatic group). Heteroaryl groups include those that have between 5 and 14 (e.g. 10) members (i.e. number of atoms in a ring) and may be monocyclic, bicyclic or tricyclic, provided that at least one of the rings is aromatic. However, when heteroaryl groups are bicyclic or tricyclic, they are linked to the rest of the molecule via an aromatic ring. Heterocyclic groups that may be mentioned include benzothiadiazolyl (including 2,1,3-benzothiadiazolyl), isothiochromanyl and, more preferably, acridinyl, benzimidazolyl, benzodioxanyl, benzodioxepinyl, benzodioxolyl (including 1,3-benzodioxolyl), benzofuranyl, benzofurazanyl, benzothiazolyl, benzoxadiazolyl (including 2,1,3-benzoxadiazolyl), benzoxazinyl (including 3,4-dihydro-2H 1,4-benzoxazinyl), benzoxazolyl, benzomorpholinyl, benzoselenadiazolyl (including 2,1,3 benzoselenadiazolyl), benzothienyl, carbazolyl, chromanyl, cinnolinyl, furanyl, imidazolyl, imidazo[1, 2-a]pyridyl, indazolyl, indolinyl, indolyl, isobenzofuranyl, isochromanyl, isoindolinyl, isoindolyl, isoquinolinyl, isothiaziolyl, isoxazolyl, naphthyridinyl (including 1,6-naphthyridinyl or, preferably, 1,5 naphthyridinyl and 1,8-naphthyridinyl), oxadiazolyl (including 1,2,3-oxadiazolyl, 1,2,4 oxadiazolyl and 1,3,4 oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7, 8-tetrahydroquinolinyl), tetrazolyl, thiadiazolyl (including 1,2,3-thiadiazolyl, 1,2,4-thiadiazolyl and 1,3,4 thiadiazolyl), thiazolyl, thiochromanyl, thiophenetyl, thienyl, triazolyl (including 1,2,3 triazolyl, 1,2,4 triazolyl and 1,3,4 triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-2 oxidised form. Particularly preferred heteroaryl groups include pyridyl, pyrrolyl, quinolinyl, furanyl, thienyl, oxadiazoly), thiadiazolyl, thiazolyl, oxazolyl, pyrazolyl, triazolyl, tetrazolyl, isoxazolyl, isothiazolyl, imidazolyl, pyrimidinyl, indolyl, pyrazinyl, indazolyl, pyrimidinyl, thiophenetyl, pyranyl, carbazolyl, acridinyl, quinolinyl, benzoimidazolyl, benzthiazolyl, purinyl, cinnolinyl and pterdinyl. Particularly preferred heteroaryl groups include monocyclic heteroaryl groups.

In the present patent structures (1), (2), (2a), (2aa), (2b), (2bb), (3), (3a), (4), (4aa), (4bb), (4cc), (4dd), (4ee), (4ff), (4gg), (4hh), (5) and (5a) are collectively referred to as structures "(1) to (5)".

In the present patent when reference is made to a structure "(2)" herein this includes also structure (2a), (2aa), (2b) and (2bb), when appropriate from a chemical point of view.

When reference is made to a structure "(2a)" herein this includes also structure (2aa), when appropriate from a chemical point of view.

When reference is made to a structure "(2b)" herein this includes also structure (2bb), when appropriate from a chemical point of view.

When reference is made to a structure "(5)" herein this includes also structure (1) and (5a), when appropriate from a chemical point of view.

When references is made to a structure "(3)" herein this includes also any of structures (3a), (4), (4aa), (4bb), (4cc), (4dd), (4ee), (4ff), (4gg), (4hh) when appropriate from a chemical point of view.

It is further noted that structures (1) to (5) and specific compounds described further on in this patent can represent any and all possible stereo-conformations of said compounds.

"r.t." refers to room temperature.
"eq" refers to equivalent.
"DCM" refers to dichloromethane.
"DMF" refers to dimethylformamide.
"EtOAc" refers to ethyl acetate.
"THF" refers to tetrahydrofuran.
"MeOH" refers to methanol.
"MeCN" refers to acetonitrile.
"Me" when used in chemical formula refers to methyl; i.e. —$CH_3$ as substituent.
"Et" when used in chemical formula refers to ethyl; i.e. —$CH_2CH_3$ as substituent.
"TES" when used in chemical formula refers to triethylsilyl; i.e. —$Si(CH_2CH_3)_3$ as substituent.
"Ac" when used in chemical formula refers to acetyl; i.e. —$C(O)CH_3$ as substituent.
"TESCl" refers to chlorotriethylsilane (which is mutatis mutandis intended to refer to the same as triethylsilyl chloride).
"DMAP" refers to 4-dimethylaminopyridine.
"EDCI" refers to 1-ethyl-3(3-dimethylaminopropyl)carbodiimide.
"TMS" refers to tetramethylsilane.
"$Ac_2O$" refers to acetic anhydride.
"TFA" refers to trifluoroacetic acid.
"MeNHOMe.HCl" refers to O-dimethylhydroxylamine hydrochloride which is mutatis mutandis intended to refer to the same as N,O-dimethylhydroxylamine.
"$Me_3Al$" refers to trimethyl aluminium.
"HEX" refers to hexane.
"Py" refers to pyridine.
"TMSOTf" refers to trimethylsilyl trifluoromethanesulfonate.
"IBA" refers to isobutyric anhydride.
"IBC" refers to isobutyryl chloride.
"DCC" refers to N,N'-dicyclohexylcarbodiimide.
"t-BuOK" refers to potassium tert-butoxide.
"MeMgBr" refers to $CH_3MgBr$.
"$Me_2AlCl$" refers to dimethylaluminum chloride.
"$Et_3Al$" refers to triethylaluminium.
"NaH" refers to sodium hydride.
"n-BuLi" refers to n-butyllithium.
"n-BuMgCl" refers to n-butylmagnesium chloride.
"DIBAL-H" refers to diisobutylaluminium hydride.

"Protective reagent" include, but are not limited to, chloroalkyl ether, chloromethyl ether, benzyl chloromethyl ether, chloromethyl methyl ether, bischloromethyl ether, β-methoxyethoxymethyl ether, tert-butyl chloromethyl ether, methoxyethyl chloromethyl ether, dichloromethyl methyl ether, Fmoc-Lys(4-methoxytrityl)-OH, 4-methoxytrityl chloride, 4-methoxytriphenylchloromethane, 4,4'-dimethoxytrityl chloride, trimethylsilyl chloride, bis(trimethylsilyl)acetamide, tert-butyldimethylsilylchloride, tri-iso-propylsilyloxymethylating agent, triisopropylsilyl ethers, triethylsilyl chloride, tetrahydropyran, imidate, benzyl trichloroacetimidate, benzyl bromide, protective reagents (i.e. reagent for introduction of protective group) mentioned in Kocienski, P. J. Protecting Groups, 3rd ed.; Georg Thieme Verlag: New York, 2005 and Greene, T. W.; Wuts, P. G. M. Protective Groups In Organic Synthesis, 3rd ed.; John Wiley & Sons: New York, 1991; Smith and Smith, 2011; Warren and Wyatt, 2007, 2009. A protective reagent is also sometimes in the scientific literature termed a protective group reagent which is also herein included into the meaning of protective reagent.

"Acylation reagent" include, but are not limited to, acid anhydride, acid chloride, acetic anhydride, acetylchloride, propionyl chloride, propionic anyhydride, butyric anhydride, butyric chloride, isobutyric anhydride, isobutyric chloride, benzoyl chloride, pivaloyl chloride, pivalic anhydride, acylating reagents in Smith and Smith, 2011; Warren and Wyatt, 2007, 2009.

In some aspects an acylating reagent is a protective reagent, as is clear for the one skilled in the art. In some other aspects a protective reagent may be an acylating agent, as is clear for the one skilled in the art.

"Oxidizing reagent" include, but are not limited to, oxygen, ozone, hydrogen peroxide, inorganic peroxides, fluorine, chlorine, iodine, bromine, nitric acid, nitrates, sulfuric acid, peroxydisulfuric acid, peroxymonosulfuric acid, chlorite, chlorate, perchlorate, hypochlorite, chromic and dichromic acids, chromium trioxide, pyridinium chlorochromate, chromate compounds, dichromate compounds, permanganates such as $KMnO_4$, sodium perborate, nitrous oxide ($N_2O$), silver oxide ($Ag_2O$), osmium tetroxide ($OsO_4$), Tollens' reagent, 2,2'-dipyridyldisulfide, manganese dioxide ($MnO_2$), perodinanes, Dess-Martin periodinane, oxidizing reagents mentioned in Smith and Smith, 2011; Warren and Wyatt, 2007, 2009.

"Amidolytic reagent" is herein defined as a reagent for formation of a Weinreb amide with structure (3), and include, but are not limited to, N,O-dimethylhydroxylamine hydrochloride (MeNHOMe.HCl), N-methyl-O-tert-butylhydroxylamine hydrochloride, N-1-(1'-naphthyl)-ethyl-O-tert-butyl-hydroxylamine, N-alkyl-O-alkylhydroxylamine, and reagents for formation of a Weinreb amide where R14 of structure (3) is covalently coupled to a resin by applying the procedures described in Salvino et al. J. Org. Chem. 1999, 64, 1823-1830 for creation of solid phase coupled Weinreb amides.

"Condensation reagent for formation of lactone cycle" include reagents capable of forming of lactone cycle, in particular (but not limited to) forming of lactone cycle from a hydroxy group and carboxy group, preferably (but not limited to) selected from the list of carbodiimides such as 1-ethyl-3-(3-dimethylaminopropyl)carbodiimide (EDCI), N,N'-dicyclohexylcarbodiimide (DCC), or condensation reagents (including those used in peptide synthesis) such as bis(2-oxo-3-oxazolidinyl)phosphonic chloride (BOPCl), O-(7-azabenzotriazol-1-yl)-N,N,N,N-tetramethyluronium hexafluorophosphate (HATU), or 2-chloro-1-methylpyridinium iodide (Mukaiyama reagent), or reagents used in the mixed anhydride method (Chen et al., 1987), and condensation reagents mentioned in Smith and Smith, 2011; Warren and Wyatt, 2007, 2009 for formation of lactone cycle.

"Alkylating reagent" refers to any compound that causes the substitution of preferably a hydrogen (or even other suited atom) of an organic compound with an alkyl group, and includes halogenated alkyl, alkyl iodide, methyl iodide, diac fdzomethane and alkylation reagent mentioned in Smith and Smith, 2011; Warren and Wyatt, 2007, 2009.

In the present patent "agent" and "reagent" is, mutatis mutandis, intended to refer to the same thing.

Wherever term "phragmalin" is used in the present invention it can be taken to represent any of xyloccensin, xylocarpin, kotschyin, phragmalin, swietenialid, neobeguin, pseudrelone, bussein, chukrasin, tabulalide or swietenitin with phragmalin being preferred, as well as it can be taken to represent any of the compounds with CAS Registry numbers 1299464-67-7, 1267877-55-3, 1248571-24-5, 1219132-70-3, 1214981-83-5, 1214976-20-1, 1186131-42-9, 1126643-44-4, 1126643-43-3, 1126643-42-2, 1053209-52-1, 1045017-87-5, 1038746-45-0, 952615-91-7, 910578-31-3, 803723-28-6, 803723-27-5, 561307-83-3, 260794-07-8, 116408-24-3, 115391-10-1, 115367-50-5, 98401-23-1, 98379-64-7, 98379-62-5, 98379-61-4, 98379-60-3, 98379-59-0, 98379-58-9, 98379-57-8, 96386-37-7, 90955-39-8, 90931-03-6, 90931-02-5, 90931-01-4, 90931-00-3, 90930-99-7, 90930-98-6, 90930-97-5, 90930-96-4, 90930-95-3, 81584-75-0, 67931-05-9, 67931-04-8, 67904-58-9, 67904-57-8, 67904-56-7, 67904-55-6, 67904-54-5, 67904-53-4, 67895-40-3, 67895-39-0, 67895-38-9, 66939-94-4, 66901-32-4, 66901-31-3, 66901-30-2, 66884-81-9, 66884-80-8, 66884-79-5, 66884-78-4, 66884-77-3, 66495-42-9, 66451-22-7, 52724-62-6, 52681-81-9, 41508-26-3, 41060-14-4, 41060-13-3, 40185-37-3, 40185-36-2, 40185-34-0, 40185-33-9, 38575-45-0, 37832-02-3, 37665-93-3, 37665-92-2, 37665-91-1, 37665-90-0, 35183-64-3, 35055-81-3 or 939775-81-2.

The present invention includes compounds of structure (1) with acronyms R306, R306AB, R306BA, R306C, R306D, R306E, R306F, R310, R310A, R310A3, R310A4, R310A5, R310B, R310B1, R310B2, R310B3, R310B4, R310B5, R310B6, R310B7, R310B8, R310B9, R310B10, R310B11, R310B12, R310B13, R310B14, R310B15, R310B16, R310B17, R310B18, as defined in WO 2008/145996.

"6" refers herein to phragmalin, when it is clear from the context that a reference to a compound is intended.

The numbers "7" to "23" refers herein to the compounds described in Examples 1 to 3 and 8, when it is clear from the context that a reference to a compound is intended.

"Aggression inducing effect" is defined herein as the effect being observable as an at least 50% increase, or even more preferably at least 100% increase, in the total number of aggressive attacks of male mice directed towards female mice (preferably the male and female mice being of 6 to 9 weeks age) after a compound has been administered (orally or sub-cutaneously) to the male mice, each male mouse thereafter being introduced separately to a female mouse; the individual aggressive attacks being counted and compared with the number of aggressive attacks of control male mice (i.e. control mice being male mice of the same age and strain as the treated ones, but which were not administered the compound but otherwise handled in the same way as the treated mice). Aggressive attacks counted in the test shall be comprised by attack bites by the male onto the female, and offensive leaps (including sideways leaps) by the male towards the female (see Miczek and O'Donnel, *Psychopharmacology*, 2012, 57, 47-55 for a description of mouse aggressive behavior and its assessment). The observation period shall be 1 h. It is further required that the number of male mice in each one of the treated and non-treated groups amount to at least three, more preferably to at least four, even more preferably to at least five, and most preferably to at least six in each group for the test to be valid; the average count of aggressive attacks for the non treated (here termed average_aggression_control) and treated (here termed average_aggression_treated) male mice during the 1 h observation period are then calculated and the percent increase (Agr_effect) is then being computed as:

$$\text{Agr\_effect} = 100 \times \frac{(\text{average\_aggression\_treated} - \text{average\_aggression\_control})}{\text{average\_aggression\_control}}$$

[For the case that average_aggression_control=0 (zero), average_aggression_control is set to the value 0.01.] In order for the effect to be regarded as being an aggression inducing effect, the numeric value of Agr_effect obtained shall amount to 50% or more, or even preferably to 100% or more. Moreover, preferably the effect should be statistically significant, at least at $p<0.05$, when assessed using an appropriate statistical method (e.g. t-test, Wilcoxon ranks sum test, chi-square, etc.) in order for the effect to be classified as aggression inducing. Example of a suited test to assess an aggression inducing effect is given in Example 4.

An "aggression inducing compound" (i.e. the compound being "aggression inducing") is herein defined a compound that in any suited dose and with any suited dosage schedule is capable of inducing an aggression inducing effect; preferably the compound being administered in a dose ranging from 0.04 to 40 mg/kg body weight. An example how to assess whether or not a compound is an aggression inducing compound is given in Example 4.

A "sexually enhancing effect" is defined herein as the effect being observable as an at least 50% increase, more preferably at least 75% increase, in the number of mounts of sexually naive male mice onto sexually receptive female mice (both preferably being of 8 to 10 weeks of age), after a compound has been administered (orally or sub-cutaneously) to the male mice, the male mice are thereafter, each one separately, being introduced to a sexually receptive female mouse; the observed number of mounts being compared with the number of mounts for control male mice (i.e. control mice being male mice of the same age and strain as the treated ones, but which were not administered the compound but otherwise handled in the same way as the treated mice). The observation period shall be 1 h. It is further required that the number of male mice in each one of the treated and non-treated groups amount to at least three, more preferably to at least four, even more preferably to at least five, and most preferably to at least six in each group for the test to be valid; the average number of mounts for the non treated (average_mount_control) and treated (average_mount_treated) during the 1 h observation period are then calculated and the percent increase (Effect) is then being computed as:

$$\text{Effect} = 100 \times \frac{(\text{average\_mount\_treated} - \text{average\_mount\_control})}{\text{average\_mount\_control}}$$

Thus, in order for the effect to be sexually enhancing the numeric value of Effect obtained shall amount to 50% or more, even more preferably 75% or more. Moreover, preferably the effect should be statistically significant, at least at p<0.05, when assessed using an appropriate statistical method (e.g. t-test, Wilcoxon ranks sum test chi-square, etc.) in order for the effect to be classified as a sexual enhancing. Example of a suited test to assess a sexual enhancing effect is given in Example 5 and in WO 2008/145996.

A "sexually enhancing compound" (i.e. the compound being "sexually enhancing") is herein defined as a compound that in any suited dose and any suited dosage schedule is capable of inducing a sexually enhancing effect; preferably the compound being administered in a dose ranging from 0.04 to 40 mg/kg body weight to the sexually naive male mice for three consecutive days and the sexual enhancing effect then being assessed on anyone of days four to fourteen, counting from the first day of administration of the compound. Examples how to assess whether a compound is a sexually enhancing compound or not are given in Example 5 and in WO 2008/145996.

"Essentially pure compound". The purity a compound of the invention can be determined by chromatography, preferably using a reversed phase chromatographic column as is well known in the art (e.g. using HPLC as described in Example 3 or Example 6, and FIGS. 5 and 6). Using chromatography the preparation of the compound of the invention, for which its purity is to be investigated, is separated into its components, the chromatographic peak corresponding to the compound of the invention is collected, the chromatographic solvent is evaporated, and the weight of the compound eluted from the column is thereafter determined. The weight thus obtained is multiplied by 100, and then divided by the weight of the preparation applied to the column, which gives a measure of the purity of the compound of the invention in percent. Alternatively the purity can be based on measurement of UV-absorption of the eluate from an HPLC column, e.g. as described in Example 3, FIGS. 5 and 6, as is also well known in the art. The purity based on UV-absorption of HPLC eluates (preferably with detection at 220 nM) can substitute for estimation of purity by weight, as defined in above in this paragraph, according to all aspects of the present invention. When the purity of a compound is at least 80% (more preferably at least 90%) according to anyone of the two here described methods it is in this invention regarded as being an essentially pure compound.

DISCLOSURE

In its most central aspect the present invention provides novel compounds with the general structure (3):

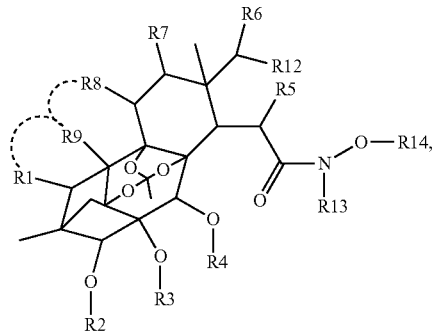

(3)

wherein the substituents and optional ring structures (denoted as hatched lines) are as detailed below in this DISCLOSURE section; specific embodiments of this aspect of the invention are given in Examples 1 to 3 of this patent, there referred to as compounds 7, 8, 14, 15, 18, 19 (LG-1725). Particularly useful embodiments of (3) are those for which R1 is 2-methoxy-2-oxoethyl, R2 is acyl, acetyl or isobutyryl, R3 is hydrogen, acetyl or isobutyryl, R4 is hydrogen, acyl or isobutyryl, R5 is hydrogen, R6 is 3-furanyl, R7 is hydrogen, R8 is hydrogen, hydroxy or acetyloxy, R9 is methyl, R12 is hydroxy, oxo or acetyloxy, R13 is methyl, and R14 is methyl. However, substituents in (3) can individually also be any of those defined further below in this DISCLOSURE section and claims amended herein, including with or without the rings denoted by hatched lines.

In yet another aspect the invention provides a process according to schema (I) comprising the reaction of a compound having the structure (2a) with amidolytic reagent(s), preferably under alkaline conditions, preferably the amidolytic reagent(s) being selected from the list of N,O-dimethylhydroxylamine hydrochloride (MeNHOMe.HCl), N-methyl-O-tert-butylhydroxylamine hydrochloride, N-alkyl-O-alkylhydroxylamine, with MeNHOMe.HCl being most preferred, preferably in the presence of an optional additional reagent (hereinafter the additional reagent being termed "additive") such as (but not limited to) those selected from the list of catalyst, metal catalyst, alkali-metal catalyst; the additive more specifically preferably being selected from the group of trimethylaluminium (Me$_3$Al), Me$_2$AlCl, Et$_3$Al, NaH, n-BuLi, MeMgBr, MgBr, Li, LiAlH$_4$, n-BuMgCl or DIBAL-H, with trimethylaluminium being most preferred, preferably the molar ratio of [(2a)]:[amidolytic reagent]:[additive] ranging from [0.1 to 10 equivalents for (2a)]:[1 to 100 equivalents for amidolytic reagent]:[2 to 200 equivalents for additive], more preferably ranging from [0.2 to 5 equivalents for (2a)]:[2 to 50 equivalents for amidolytic reagent]:[4 to 100 equivalents for additive], more preferably ranging from [0.4 to 2.5 equivalents for (2a)]:[4 to 25 equivalents for amidolytic reagent]:[8 to 50 equivalents for additive], most preferably ranging from [0.8 to 1.25 equivalents for (2a)]:[8 to 12.5 equivalents for amidolytic reagent]:[16 to 25 equivalents for additive], preferably using a temperature ranging from −10° C. to 100° C., more preferably ranging from 0° C. to 80° C., more preferably ranging from 10° C. to 60° C., more preferably ranging from 15° C. to 40° C., and most preferably ranging from 18° C. to 25° C., preferably using a reaction time ranging from 10 minutes to 72 hours, more preferably ranging from 10 minutes to 24 hours, more preferably ranging from 10 minutes to 6 hours, more preferably ranging from 20 minutes to 2 hours, and most preferably ranging 30 minutes to one hour, in order to obtain the compound according to structure (4) [which is a more specific representative of structure (3), wherein R12 is hydroxy], by ring opening of the lactone ring in structure (2a), as shown in the schema (I) below:

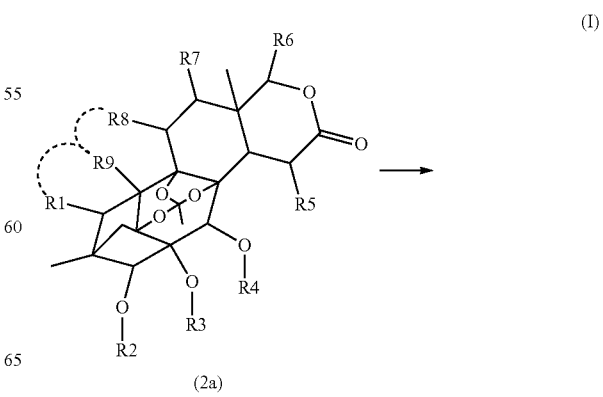

(I)

(2a)

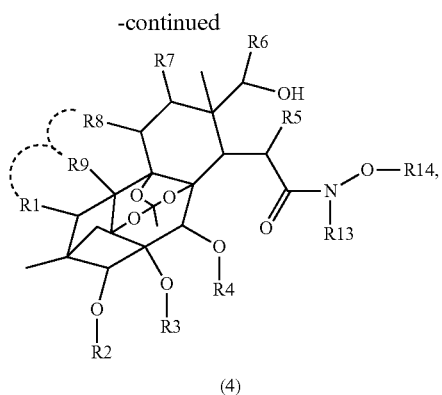

(4)

[wherein (2a) and (4) R1 is preferably 2-methoxy-2-oxo-ethyl, R2 is preferably acyl, acetyl or isobutyryl, R3 is preferably hydrogen, acyl, acetyl or isobutyryl, R4 is preferably hydrogen, acyl or isobutyryl, R5 is preferably hydrogen, R6 is preferably 3-furanyl, R7 is preferably hydrogen, R8 is preferably hydrogen, hydroxy or acetyloxy, R9 is preferably methyl, R13 is preferably methyl, and R14 is preferably methyl; albeit substituents in (2a) and (4) can individually be any of those defined further below in this DISCLOSURE section and claims amended herein, including with or without the rings denoted by hatched lines], wherein in schema (I) the substituents and optional ring structures (denoted as hatched lines) are as detailed below in this DISCLOSURE section; specific embodiments of this aspect of the invention is given in Examples 1 to 3 of this patent, there referred to as conversion of compound 6 to compound 7; conversion of compound 13 to compound 14; conversion of compound 17 to compound 18. [I.e. the invention providing the formation of Weinreb amide (4) from lactone (2a)].

In a more specific embodiment of schema (I) the invention provides a process according to schema (Ia) comprising the reaction of a compound according to structure (2aa) with amidolytic reagent(s), preferably under alkaline conditions, preferably the amidolytic reagent(s) being selected from the list of N,O-dimethylhydroxylamine hydrochloride (MeN-HOMe.HCl), N-methyl-O-tert-butylhydroxylamine hydrochloride, N-alkyl-O-alkylhydroxylamine, with MeN-HOMe.HCl being most preferred, preferably in the presence of an optional additional reagent ("additive") such as (but not limited to) those selected from the list of catalyst, metal catalyst, alkali-metal catalyst; the additive more specifically preferably being selected from the group of trimethylaluminium (Me$_3$Al), Me$_2$AlCl, Et$_3$Al, NaH, n-BuLi, MgBr, MeMgBr, Li, LiAlH$_4$, n-BuMgCl or DIBAL-H, with trimethylaluminium being most preferred, preferably the molar ratio of [(2aa)]:[amidolytic reagent]:[additive] ranging from [0.1 to 10 equivalents for (2aa)]:[1 to 100 equivalents for amidolytic reagent]:[2 to 200 equivalents for additive], more preferably ranging from [0.2 to 5 equivalents for (2aa)]:[2 to 50 equivalents for amidolytic reagent]:[4 to 100 equivalents for additive], more preferably ranging from [0.4 to 2.5 equivalents for (2aa)]:[4 to 25 equivalents for amidolytic reagent]:[8 to 50 equivalents for additive], most preferably ranging from [0.8 to 1.25 equivalents for (2aa)]:[8 to 12.5 equivalents for amidolytic reagent]:[16 to 25 equivalents for additive], preferably using a temperature ranging from −10° C. to 100° C., more preferably ranging from 0° C. to 80° C., more preferably ranging from 10° C. to 60° C., more preferably ranging from 15° C. to 40° C., and most preferably ranging from 18° C. to 25° C., preferably using a reaction time ranging from 10 minutes to 72 hours, more preferably ranging from 10 minutes to 24 hours, more preferably ranging from 10 minutes to 6 hours, more preferably ranging from 20 minutes to 2 hours, and most preferably ranging 30 minutes to one hour, in order to obtain the compound according to structure (4aa) [which is a more specific representative of structure (3)], by ring opening of the lactone ring in structure (2aa), thereby providing the chemoselective formation of a Weinreb amide (4aa) from the precursor (2aa) as shown in the schema (Ia) below:

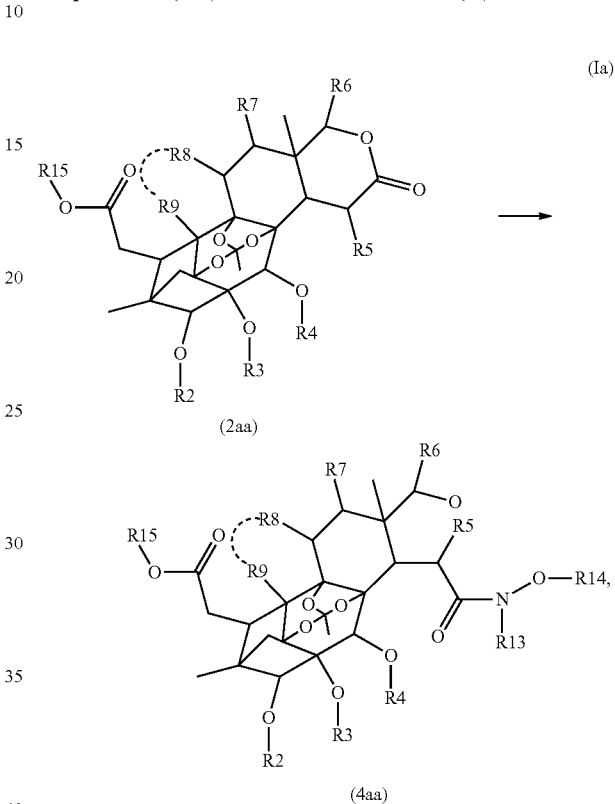

wherein (2aa) and (4aa) R15 is preferably methyl. Thus, in this more specific embodiment the invention provides the chemoselective opening of the lactone ring, which can be interpreted as a the hydrolysis of the lactone, forming an intermediate carboxylic acid, which is then followed by the formation of the Weinreb amide (4aa), while leaving the ester group at carbon 7 intact (thus providing chemoselectivity) [for atom numbering see number of atoms in the phragmalin structure (i.e. compound 6) below]. This feature of the invention is illustrated in Examples 1 to 3 of this patent, by the conversion compound 6 to compound 7; conversion of compound 13 to compound 14; conversion of compound 17 to compound 18. In most embodiments it is further preferred that in compound (2aa) and (4aa) R2 is acyl, acetyl or isobutyryl, R3 is hydrogen, acyl, acetyl or isobutyryl, R4 is hydrogen, acyl or isobutyryl, R5 is hydrogen, R6 is 3-furanyl, R7 is hydrogen, R8 is hydrogen, hydroxy or acetyloxy, R9 is methyl, R13 is methyl and R14 is methyl. However, substituents in (2aa) and (4aa) can individually be any of those defined below in this DISCLOSURE section and amended claims, including with or without the ring denoted by the hatched line, as well.

The conditions for forming (4) and (4aa) from, respectively, a compound (2a) or (2aa) according to, respectively schema (I) and (Ia), needed to be surprisingly distinct; only a certain range of molar ratios of MeNHOMe.HCl, Me$_3$Al and precursor (2a) or (2aa), as well as only the appropriate reaction temperature and only a narrow time window before quenching, formed the desired product (4) or (4aa). This is being evident by studying the conditions explored in Examples 1 and 3 for the conversion of compound 6 to compound 7 and the conversion of compound 17 to compound 18; the very specific conditions detailed in Examples 1 and 3 required to afford compound (4)/(4aa) comprise accordingly an extremely important embodiment of the invention, provided by this patent. Surprisingly, however, using of other closely similar reagents instead of Me₃Al in conjunction with MeNHOMe.HCl, such as trietylaluminium (Et₃Al), dimethylaluminium chloride (Me₂AlCl) or even isopropylmagnesium chloride (iPrMgCl) (which are well known in from prior art to be usable with MeNHOMe.HCl for formation of Weinreb amide in other cases) failed in forming the desired Weinreb amide and these failing reagents (i.e. Et₃Al, Me₂AlCl, iPrMgCl) are therefore in the most specific embodiments of the invention excluded from the list of "additive" according to the above specifications for affording process (I) and (Ia). Moreover too short time and too long time failed in providing the desired Weinreb amide, as well as only a certain molar ratio of MeNHOMe.HCl: Me₃Al gave the desired Weinreb amide; all of this thus showing the extremely distinct conditions required to afford the process (I) and (Ia), the conditions which are defined above, in the Examples and amended claims.

In a further aspect the invention provides a means to obtain a further structure (3) from the more specific structure (4) [as well as from the even more specific structure (4aa), and even from (4bb), (4cc), (4dd), (4ee), (4ff), (4gg) and (4hh), and even from structure (3) (for structures see below)] [said compounds which may have been obtained by anyone of the processes (I) and (Ia), or by other means] by subjecting the compound of structure (4) [and here listed other variations of (3)] to chemical reaction, such as derivatization, oxidation, catalysis, decomposition, replacement, substitution, addition, elimination, rearrangement, hydrolysis, acylation, alkylation, reduction, halogenation, hydrogenation, condensation, biochemical reaction, as would be evident by anyone skilled in the art (i.e. by subjecting the compound (4) [(3)] to reagents well known in the art, e.g. using acylation reagent, oxidizing reagent, reducing reagent, condensation reagent, coupling reagent, halogenating agent, protective reagent, reagents described in Smith and Smith, 2011; Warren and Wyatt, 2007, 2009), acid condition, alkaline condition, oxidizing condition, reducing condition; specific embodiments of this aspect of the invention are given in Examples 1 to 3, there being represented by conversion of compound 7 to compound 8 by derivatization using protective reagent; conversion of compound 14 to compound 15 by oxidation using oxidizing reagent; conversion of compound 18 to compound 19 by oxidation using oxidizing reagent; conversion of compound 7 to compound 14 by acylation using acylation reagent.

In a very specific embodiment of the aspect of the invention of the previous paragraph, the invention provides the process of schema (IV) comprising the regioselective oxidation of the structure (4bb) [which is a more specific structure of structure (3)] to afford another structure (4cc) [which is also a more specific structure of (3)], by subjecting the compound of structure (4bb) to oxidizing condition(s), preferably using oxidizing reagent, such as using any oxidizing reagent and/or condition described in Smith and Smith, 2011; Warren and Wyatt, 2007, 2009, preferably the oxidizing reagent being selected from the list of Dess-Martin periodinane or MnO₂, with Dess-Martin periodinane being most preferred, the overall reaction being in accordance with schema (IV):

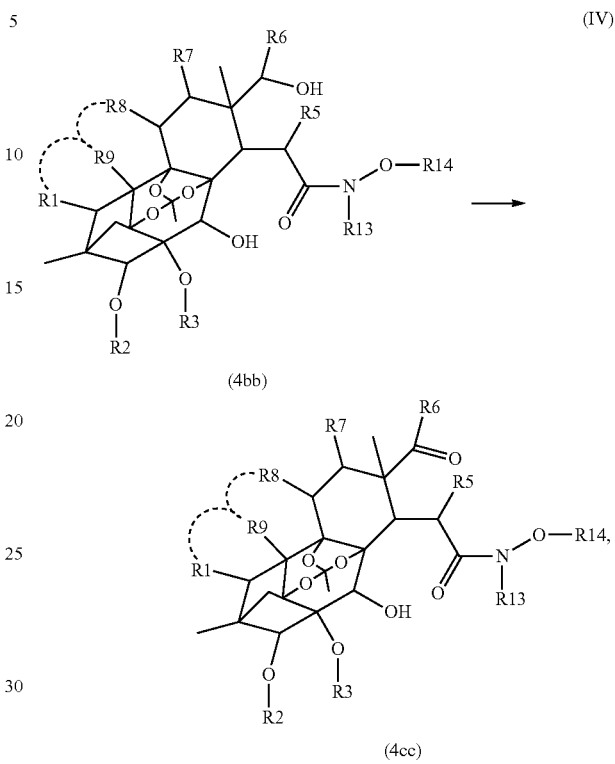

wherein R1 is preferably 2-methoxy-2-oxoethyl, R2 is preferably acyl, acetyl or isobutyryl, R3 is preferably hydrogen, acetyl or isobytyryl, R5 is preferably hydrogen, R6 is preferably 3-furanyl, R7 is preferably hydrogen, R8 is preferably hydrogen, hydroxy or acetyloxy, R9 is preferably methyl, R13 is preferably methyl and R14 is preferably methyl. However, substituents in (4bb) and (4cc) can individually be any of those defined below in this DISCLOSURE section and amended claims, including with or without the rings denoted by hatched lines, as well. The regioselective oxidation in (IV), affecting only the hydroxy group at carbon 17 but not the hydroxy group at carbon 30, can be achieved by using the specific conditions described in Example 2 and 3 for conversion of compound 14 to 15, and 18 to 19, but are not limited to these conditions; rather any type of method for oxidation can be used; oxidation methods being well-known in the art (see e.g. Smith and Smith, 2011; Warren and Wyatt, 2007, 2009). This is because the chemoselectivity is afforded by the intrinsic properties of (4bb), in a way that was not foreseeable by prior art, but provided herein as discovery; this discovery being highly useful in affording the more desired compounds of the invention where the hydroxy function at carbon 17 of the compound of the invention has been converted to a keto group.

Thus, accordingly in the process according to schema (IV) selective oxidation is afforded at the hydroxy group at carbon 17 by the process of the invention, while the hydroxy group at carbon 30 is left unaffected [atom numbering as in structure (2b)], which can preferably be afforded by use of Dess-Martin periodinane, although other methods for oxidation can be used as well. This feature of the invention is demonstrated in Examples 2 and 3 by the regioselective oxidation of compound 14 to compound 15, as well as the regioselective oxidation of compound 18 to compound 19. It was indeed a surprising finding not foreseeable by any prior chemical knowledge that the oxidation proceeded in this regioselective manner, and it is an important feature provided by this invention in order to proceed from a structure (4) [most specifically (4bb)] into formation of compounds of structure (5) (see below) wherein (5) R12 is oxo, such as to provide compound 21 (R306), R306AB, R306BA, R306C, R306E, R306D, R306F, compound 16 (SAE6) and compound 20 (SAE5), the processes for which are disclosed herein (i.e. processes of schema III, IIIa and IIIb) which are among the most desired embodiments of the invention.

A further aspect of the invention is that the hydroxy group at carbon 3 of a compound (4bb) needs to be protected with protective group or even more preferably acylated in order to provide structure (4cc) when affording the process according to schema (IV) of the invention; in the case R2 is hydrogen in (4bb), oxidation proceeds at the hydroxy group at carbon 3 which results in that the phragmalin skeleton is destroyed by the oxidation. (This was for example seen in the oxidation of compound 7 of Example 1 using manganese oxide ($MnO_2$) at r.t. for 4 h in acetonitrile). Thus, accordingly, for the specific embodiment of the invention provided by schema (IV) (or for that sake the case that any compound of structure (3) where R12 is hydroxy is subjected to oxidation in order to oxidize the hydroxy group at carbon 17) it is preferred that R2 is a protective group or an acyl group; preferred is that R2 is acyl, acetyl or isobutyryl, with isobutyryl being most preferred. It is moreover preferred that the protective group is introduced (or being present) already at the stage prior to the formation of the Weinreb amide; i.e. being in or being introduced into the compound (2a) or (2aa) [or even in/into (2b) or (2bb) when using the process according to schema (II) or (IIa) below], prior to formation of Weinreb amide (3), (3a), (4), (4aa), (4bb), (4cc), (4dd), (4ee), (4ff), (4gg), (4hh). This is because trying to introduce the acyl group or protective group in the latter Weinreb amides results in low yields with formation of many side products. [C.f. Example 2 where the preferred route is the conversion of 6 to 13 followed by conversion of 13 to 14 (overall yield from 6 to 14 being about 22%), to be compared with the less preferred route of first converting 6 to 7 (Example 1), followed by the conversion of 7 to 14 (Example 2) (overall yield from 6 to 14 being only about 10%); c.f. also Example 3 where the preferred route is conversion of 6 to 17 followed by conversion of 17 to 18 (overall yield from 6 to 18 being about 34%, to be compared with the less preferred route of conversion of 6 to 7 (Example 1) followed by conversion of 7 to 18 (Example 3); the latter giving negligible overall yield for conversion of 6 to 18 due to formation of many side products during the conversion of 7 to 18).] Therefore, accordingly, the invention incorporates optionally into the other processes described in this patent as a very important aspect the process P1 where a first compound according to structure (2a), where R2 is preferably hydrogen (other substituents being as described below in this DISCLOSURE section), is reacted with an acylating reagent or a protective reagent in order to form a second compound with structure (2a) where the hydroxy group at carbon 3 is preferably protected with an acyl group or protective group; therefore also accordingly the invention incorporates optionally into the other processes described in this patent as a very important aspect the process P2 where a first compound according to structure (2b), where R2 is preferably hydrogen (other substituents being as described below in this DISCLOSURE section), is reacted with an acylating reagent or a protective reagent in order to form a second compound with structure (2b) where the hydroxy group at carbon 3 is preferably protected with an acyl group or protective group; therefore also accordingly the invention incorporates optionally into the other processes described in this patent as a very important aspect the process P3 where a first compound according to structure (3), where R2 is preferably hydrogen (other substituents being as described below in this DISCLOSURE section), is reacted with an acylating reagent or a protective reagent in order to form a second compound with structure (3) where the hydroxy group at carbon 3 is preferably protected with an acyl group or protective group; methods for acylation and/or introduction of protective groups to be used in process P1 to P3 being well-known in the art (Smith and Smith, 2011; Warren and Wyatt, 2007, 2009). In particular in the process P1, P2 and P3 where an acylating reagent is used, the compound with the respective structure (2a), (2b) and (3) is preferably reacted with an acylating reagent selected from the list of acid anhydride, acid chloride, acetic anhydride, acetylchloride, propionyl chloride, propionic anyhydride, butyric anhydride, butyric chloride, isobutyric anhydride, isobutyric chloride, benzoyl chloride, pivaloyl chloride, pivalic anhydride. For the process P1, P2 and P3 where a protective reagent is used, the compound with the respective structure (2a), (2b) and (3) is preferably reacted with a protective reagent selected from the list of chloroalkyl ether, chloromethyl ether, benzyl chloromethyl ether, chloromethyl methyl ether, bischloromethyl ether, β-methoxyethoxymethyl ether, tert-butyl chloromethyl ether, methoxyethyl chloromethyl ether, dichloromethyl methyl ether, Fmoc-Lys(4-methoxytrityl)-OH, 4-methoxytrityl chloride, 4-methoxytriphenylchloromethane, 4,4'-dimethoxytrityl chloride, trimethylsilyl chloride, bis(trimethylsilyl)acetamide, tert-buty)dimethylsilylchloride, tri-iso-propylsilyloxymethylating agent, triisopropylsilyl ethers, triethylsilyl chloride, tetrahydropyran, imidate, benzyl trichloroacetimidate, benzyl bromide, protective reagents mentioned in Kocienski, P. J. Protecting Groups, 3rd ed.; Georg Thieme Verlag: New York, 2005 and Greene, T. W.; Wuts, P. G. M. Protective Groups In Organic Synthesis, 3rd ed.; John Wiley & Sons: New York, 1991. Moreover, for the sake of the present patent any of process P1 to P3 can be incorporated into any other of the processes of this patent (where appropriate from a chemical point of view) in order to introduce an acyl group or protective group onto a hydroxy group at any one of carbons 2, 3, 17 and 30 of compound with structure (2a), (2b) or (3) by introducing into the process of P1 to P3 as the first compound the respective compound (2a), (2b) or (3) where one, two, three or four of carbons 2, 3, 17 and 30 are substituted with a hydroxy group. While the processes P1 and P2 are preferred over process P3, the process P1 is most preferred for optional incorporation into any of the other processes of the present invention.

In a further aspect the invention provides a process according to schema (II) comprising the reaction of a compound according to structure (2b) with amidolytic reagent(s), preferably under alkaline conditions, preferably the amidolytic reagent(s) being selected from the list of N,O-dimethylhydroxylamine hydrochloride (MeNHOMe.HCl), N-methyl-O-tert-butylhydroxylamine hydrochloride, N-alkyl-O-alkylhydroxylamine, with MeNHOMe.HCl being most preferred, preferably in the presence of on optional additional reagent ("additive") such as (but not limited to) those selected from the list of catalyst, metal catalyst, alkali-metal catalyst; the additive more specifically preferably being selected from the group of trimethylaluminium ($Me_3Al$), $Me_2AlCl$, $Et_3Al$, NaH, MeMgBr, MgBr, Li, $LiAlH_4$, n-BuMgCl or DIBAL-H, with trimethylaluminium being most preferred, preferably the molar ratio of [(2b)]:[amidolytic reagent]:[additive] ranging from [0.1 to 10 equivalents for (2b)]:[1 to 100 equivalents for amidolytic reagent]:[2 to 200 equivalents for additive], more preferably ranging from [0.2 to 5 equivalents for (2b)]:[2 to 50 equivalents for amidolytic reagent]:[4 to 100 equivalents for additive], more preferably ranging from [0.4 to 2.5 equivalents for (2b)]:[4 to 25 equivalents for amidolytic reagent]:[8 to 50 equivalents for additive], most preferably ranging from [0.8 to 1.25 equivalents for (2b)]:[8 to 12.5 equivalents for amidolytic reagent]:[16 to 25 equivalents for additive], preferably using a temperature ranging from −10° C. to 100° C., more preferably ranging from 0° C. to 80° C., more preferably ranging from 10° C. to 60° C., more preferably ranging from 15° C. to 40° C., and most preferably ranging from 18° C. to 25° C., preferably using a reaction time ranging from 10 minutes to 72 hours, more preferably ranging from 10 minutes to 24 hours, more preferably ranging from 10 minutes to 6 hours, more preferably ranging from 20 minutes to 2 hours, and most preferably ranging 30 minutes to one hour, in order to obtain the compound according to structure (3), as shown in schema (II):

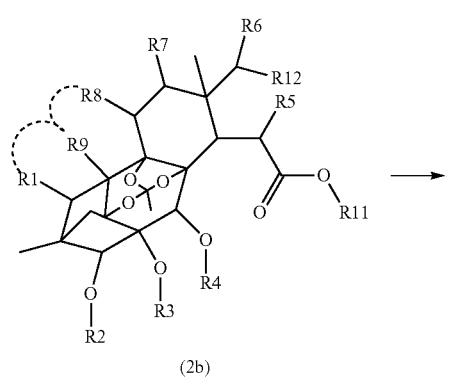

(2b)

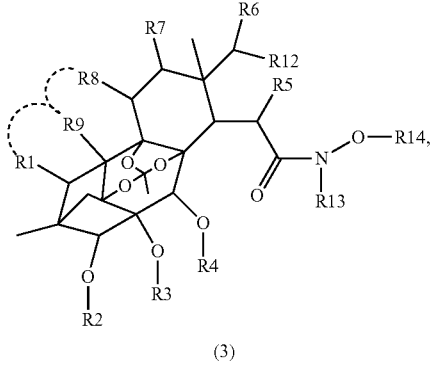

(3)

affording formation of Weinreb amide at carbon 16.

Moreover, in a more specific sense the invention provides a process according to schema (IIa) where a chemoselective formation of Weinreb amides at carbon 16 of a more specific compound (2bb) of (2b), forming the Weinreb amide (4dd), while leaving the ester group at carbon 7 intact [for atom numbering see structure (2b) above and phragmalin structure below] is afforded by substituting compound (2b) in the process according to schema (II) (as detailed above) with a compound with structure (2bb) in order to form the Weinreb amide (4dd) as shown in schema (IIa):

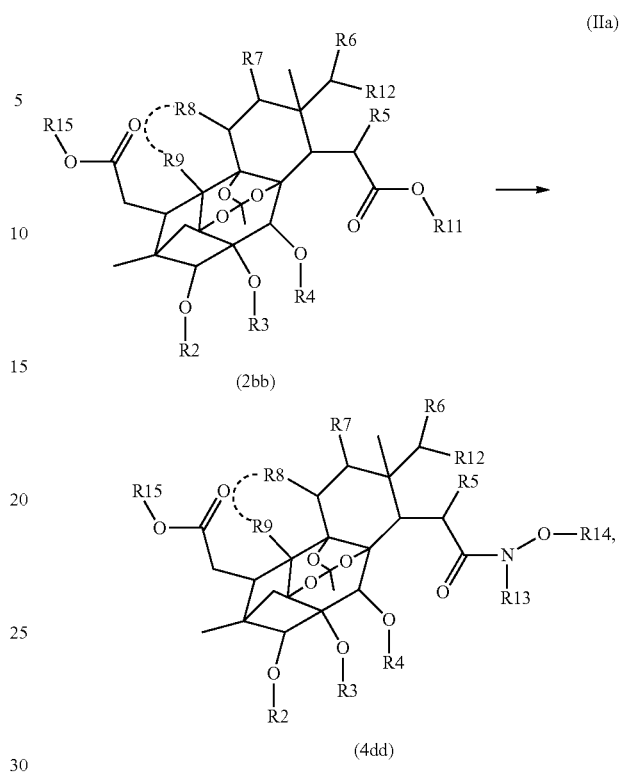

In schema (II) and (IIa) for compound (2b), (2bb), (3) and (4dd) R1 (when present) is preferably 2-methoxy-2-oxoethyl, R2 is preferably acyl, acetyl or isobutyryl, R3 is preferably hydrogen, acyl, acetyl or isobutyryl, R4 is preferably hydrogen, acyl, acetyl or isobutyryl, R5 is preferably hydrogen, R6 is preferably 3-furanyl, R7 is preferably hydrogen, R8 is preferably hydrogen, hydroxy or acetyloxy, R9 is preferably methyl, R11 is preferably hydrogen or methyl, R12 is preferably hydroxy, oxo or acetyloxy, with oxo being most preferred, R13 is preferably methyl, R14 is preferably methyl and R15 is preferably methyl (albeit substituents can individually be anyone as defined below in this DISCLOSURE section and amended claims, including with or without the rings denoted by hatched lines), the reaction preferably being afforded by use of amidolytic reagent(s); the amidolytic reagent preferably being N,O-dimethylhydroxylamine hydrochloride (MeNHOMe.HCl), preferably together with trimethyl aluminium ($Me_3Al$), wherein in schema (II) and (IIa) the substituents and optional ring structures (denoted as hatched lines) are as detailed below in this DISCLOSURE section. These routes are obvious stated the teachings of this patent for conversion of compound (2a)) to compound (3) and the variations of this reaction taught herein, including taking advantage of the regio- and chemoselectivities taught by the present invention. However, due to the small amounts of (2b) and (2bb) [in fact all known plant materials known comply with structure (2bb)] available in plants, schema (II) and (IIa) allow only minor quantities of compound (3) [or (4dd)] to be produced, compared to using schema (I) or (Ia). Therefore, the processes of schema (II) and (IIa) are specifically excluded from most processes of the invention (i.e. in particular those aiming for high yield), as well as the use of compound (2b) and (2bb) (in particular when obtained directly from a plant) as starting material for the production/synthesis of anyone of (1), (2b), (2bb), (3), (3a), (4), (4aa), (4bb), (4cc), (4dd), (4ee), (4ff), (4gg), (4hh), (5a) and (5) is excluded for the same reason. Moreover, even more specifically, the present patent includes most preferably only the process of the invention which is capable of providing anyone of compounds of (1), (2b), (2bb), (3), (3a), (4), (4aa), (4bb), (4cc), (4dd), (4ff), (4gg), (4hh), (5a) and (5) in a yield which is higher than 50 g, even more preferably higher than 100 g, and even more preferably higher than 150 g, even more preferably higher than 180 g, even more preferably higher than 250 g, even more preferably higher than 390 g, and most preferably higher than 450 g per starting ton (1000 kg) of dried plant material, which is in fact possible only when (2a) or (2aa) is used as starting material, as is demonstrated in Examples 1 to 3 and 8, and by the calculations provided below, but not by using a compound (2b) or (2bb) as starting material due to the low contents of (2b) and (2bb) in plant tissues.

In the present patent the process of scheme (Ia) is most preferred, followed by the process of scheme (I), followed by the process of scheme (IIa), followed by the process of scheme (II); this means that for the sake of this patent the starting compound with structure (2aa) is most preferred, (2a) is somewhat less preferred, (2bb) is even less preferred and (2b) is the least preferred for providing anyone of Weinreb amides (3), (3a), (4), (4aa), (4bb), (4cc), (4dd), (4ee), (4ff), (4gg), (4hh).

In yet another aspect the invention provides a process according to schema (III) where a starting compound with structure (3), wherein R4 in (3) is preferably hydrogen such as in compound (3a); [whenever a structure (3) is used in the process according to schema (III) as starting compound it is also intended the variation (3a), as well any of structures (4), (4aa), (4bb), (4cc), (4dd), (4ee), (4gg) and (4hh), which are also variations of structure (3), whenever appropriate from a chemical point of view and wherein R4 in (3), (4), (4aa), (4bb), (4cc), (4dd), (4ee), (4ff), (4gg) and (4hh). is preferably hydrogen], undergoes intramolecular lactonization so as to form a product with structure (5) [compound (5) encompassing structure (5a) and (1), as well as well as structures of claim 40 in WO 2008/145996], preferably by subjecting compound (3) [(3a), (4), (4aa), (4bb), (4cc), (4dd), (4ee), (4ff), (4gg), (4hh)] to reagent(s) comprised by Lewis acid(s), the Lewis acid(s) preferably being selected from the list of trimethylsilyl trifluoromethanesulfonate (TMSOTf), boron trifluoride diethyl complex ($BF_3.Et_2O$), aluminium triethanolate (Al(OEt)$_3$), zinc trifluoromethane-sulfonate (Zn(OTf)$_2$), iron(II) acetate (Fe(OAc)$_2$), iron(III) acetate (Fe(OAc)$_3$), iron(III) chloride (FeCl$_3$), copper(I) chloride (CuCl), copper(II) trifluoromethane-sulfonate (Cu(OTf)$_2$), magnesium chloride (MgCl$_2$), magnesium methylate (Mg(OMe)$_2$), magnesium trifluoromethanesulfonate (Mg(OTf)) and other related metal salts, hydroxides and alkoxides, or subjecting compound (3) to bases such as potassium carbonate (K$_2$CO$_3$), caesium carbonate (Cs$_2$CO$_3$), n-butyllithium (n-BuLi), lithium bis(trimethylsilyl)amide (LiHMDS), sodium bis(trimethylsilyl)amide (NaHMDS), the preferred reagent being TMSOTf.

In another variation the invention provides a process according to schema (III) where a starting compound with structure (3), wherein R4 in (3) is preferably hydrogen such as in compound (3a); [whenever a structure (3) is used in the process according to schema (III) as starting compound it is also intended the variation (3a), as well any of structures (4), (4aa), (4bb), (4cc), (4dd), (4ee), (4ff) (4gg) and (4hh), which are also variations of structure (3), whenever appropriate from a chemical point of view and wherein R4 in (4), (4aa), (4bb), (4cc), (4dd), (4ee), (4ff), (4gg) and (4hh), is preferably hydrogen], undergoes intramolecular lactonization so as to form a product with structure (5) [compound (5) encompassing structure (5a) and (1), as well as well as structures of claim 40 in WO 2008/145996], by a first step comprised by subjecting compound (3) [(3a), (4), (4aa), (4bb), (4cc), (4dd), (4ee), (4ff), (4gg) or (4hh)] to the reaction of deamidation, preferably by the process of hydrolysis using alkaline conditions, so as to form a free carboxylic function at carbon 16, preferably the alkaline condition being afforded with use of KOH or t-BuOK, followed a second step to afford intramolecular ring closure forming the lactone cycle by applying methods well known in the art, preferably the second step comprised by reacting the product from the first step with a condensation reagent for formation of lactone cycle, preferably using a condensation reagent for formation of lactone cycle such as those described in Smith and Smith, 2011; Warren and Wyatt, 2007, 2009, or the condensation reagent preferably being selected from the list of carbodiimide, 1-ethyl-3-(3-dimethylaminopropyl)carbodiimide (EDCl), N,N'-dicyclohexylcarbodiimide (DCC), bis(2-oxo-3-oxazolidinyl)phosphonic chloride (BOPCl), O-(7-azabenzotriazol-1-yl)-N,N,N,N-tetramethyluronium hexafluorophosphate (HATU), 2-chloro-1-methylpyridinium iodide (Mukaiyama reagent), or by applying the mixed anhydride method (Chen et al., 1987), with reagent EDCI being preferred.

The processes according to schema (III) described above is summarized as follows:

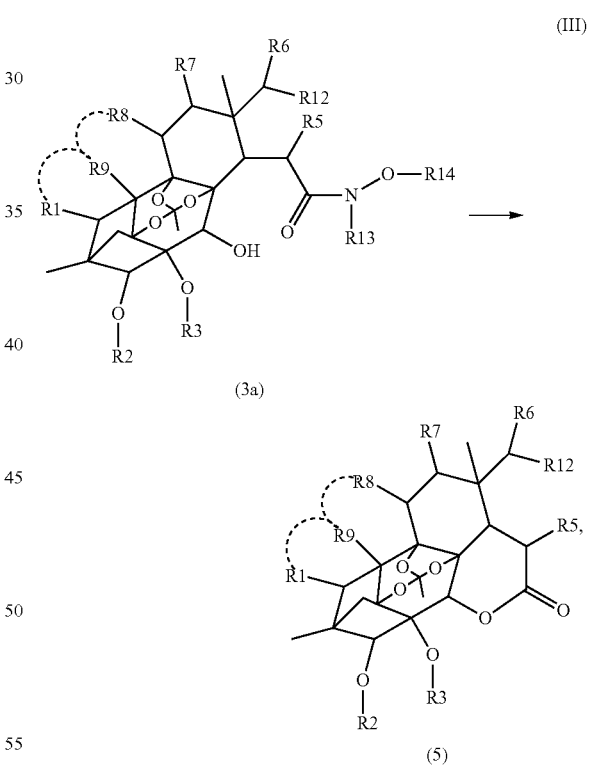

where the compound (3a) [and its variations (3), (4), (4aa), (4bb), (4cc), (4dd), (4ee), (4ff), (4gg) and (4hh)] is subjected to deamidation followed by closing of a ring with formation of a lactone with structure (5), wherein in schema (III) the substituents and optional ring structures (denoted as hatched lines) are as detailed below in this DISCLOSURE section; specific embodiments of this aspect of the invention are given in Examples 1 to 3, there referred to as conversion of compound 8 to compound 9; conversion of compound 15 to compound 16; conversion of compound 19 to compound 20.

Particularly useful embodiments of schema (III) are those wherein (3a) and (5) R1 is 2-methoxy-2-oxoethyl, R2 is acyl, acetyl or isobutyryl, R3 is hydrogen, acetyl or isobutyryl, R5 is hydrogen, R6 is 3-furanyl, R7 is hydrogen, R8 is hydrogen, hydroxy or acetyloxy, R9 is methyl, R12 is hydroxy, oxo or acetyloxy, R13 is methyl, and R14 is methyl. However, substituents in (3a) and (5) can individually also be any of those defined further below in this DISCLOSURE section and claims amended herein, including with or without the rings denoted by hatched lines.

A more specific variation of the process according to schema (III) is provided by the process according to schema (IIIa):

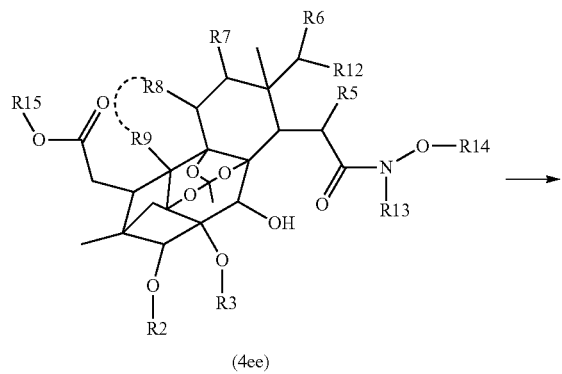
(IIIa)

and an even more very specific variation of schema (III) is provided by schema (IIIb):

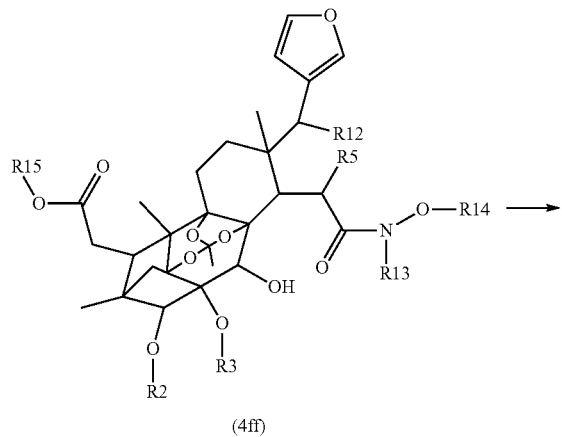
(IIIb)

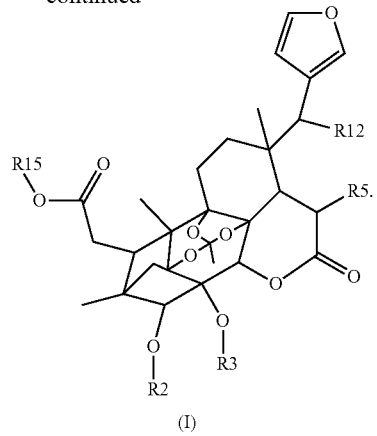
(I)

The processes according to schema (IIIa) and (IIIb) are performed in an identical fashion as the processes of schema (III), however with the difference that the starting compound (3) [(3a)] used as starting compound in process (III) is exchanged with the compound (4ee) or (4ff) [or they could even exchanged with the compounds (4gg) or (4hh) defined in the claims section in a very specific variation, (4ee) and (4ff) being more specific variations of (4ee) and (4ff)] as starting compound in the respective process (IIIa) and (IIIb). Particularly useful embodiments of the processes of schema (IIIa) and (IIIb) are those wherein in (4ee), (4ff) [or even in (4gg) or (4hh)], (1) and (5a) 82 is acyl, acetyl or isobutyryl, R3 is hydrogen, acyl, acetyl or isobutyryl, R5 is hydrogen, R6 is 3-furanyl, R7 is hydrogen, R8 is hydrogen, hydroxy or acetyloxy, R9 is methyl, R12 is hydroxy, oxo or acetyloxy, R13 is methyl, R14 is methyl and R15 is methyl. However, substituents in (4ee), (4ff), [and even (4gg) and (4hh)], (1) and (5a) can individually also be any of those defined further below in this DISCLOSURE section and claims amended herein, including with or without the rings denoted by hatched lines. [Compounds (4ee) and (4ff) and even (4gg) and (4hh) can of course be obtained from the appropriate variation of a compound (2) or (3) as starting compound by use of the processes of schemes (I), (Ia), (II), (IIa), (IV), P1 to P3 and combinations thereof].

The ring closure according to schema (III), (IIIa) and (IIIb) can thus be afforded by hydrolysis of the Weinreb amide (3) so as to form a free carboxylic acid at carbon 16 followed by the ring closing, e.g. using the coupling reagent EDCI (see Example 1 for conversion of 8 to 9 for a specific example of this embodiment of the invention). However, ring closing to lactone can also be performed by use of Lewis acids, preferably by use of trimethylsilyl trifluoromethanesulfonate (TM-SOTf), as is demonstrated in Example 2 for the conversion of 15 to 16, and in Example 3 for the conversion of 19 to 20. Other methods for ring closing so as to form the desired lactone are well known in the art, and can be used as well (see e.g. Smith and Smith, 2011; Warren and Wyatt, 2007, 2009).

In a further aspect the invention provides the compound (3) for use to obtain a further structure by subjecting compound (3) to chemical reaction, the chemical reaction e.g. being anyone of (but not limited to) derivatization, oxidation, catalysis, decomposition, disconnection, replacement, substitution, addition, elimination, rearrangement, hydrolysis, acylation, alkylation, reduction, halogenation, hydrogenation, condensation, biochemical reaction; that is by introducing compound (3) [or any of its more specific variations (3a), (4), (4aa), (4bb), (4cc), (4dd), (4ee), (4ff), (4gg) or (4hh)] with chemical reagent and/or condition, such as oxidizing reagent, reducing reagent, acylating reagent, protecting reagent, condensation reagent, coupling reagent, halogenating agent, alkylating reagent, alkaline condition, acidic condition, oxidizing condition, reducing condition, as would be evident by anyone skilled in the art, applying methods well known in the art, e.g. including introducing compound (3) with reagents described in Smith and Smith, 2011; Warren and Wyatt, 2007, 2009.

In a very specific embodiment of the aspect of the invention of the preceeding paragraph, the invention provides a process were a starting compound with structure (3) is used for obtaining a compound (2b) by subjecting compound (3) to the reaction of deamidation, preferably by the process of hydrolysis using alkaline conditions, preferably the alkaline condition being afforded by use of potassium t-BuOK or KOH, so as to form a carboxy function at position 16, thus forming a first compound with structure (2b) where R11 is hydrogen, which may be optionally followed by alkylation of the first compound (2b) at position 16 by subjecting the first compound (2b) to an alkylating agent so as to form a second compound with structure (2b) where R11 is an alkyl group, using alkylating reagents well known in the art, the alkylating reagent preferably being selected from the list of halogenated alkyl, alkyl iodide, methyl iodide, diazomethane (for further methods and reagents for amidolysis and alkylation useful for this aspect of the invention see e.g. Smith and Smith, 2011; Warren and Wyatt, 2007, 2009), according to schema (V):

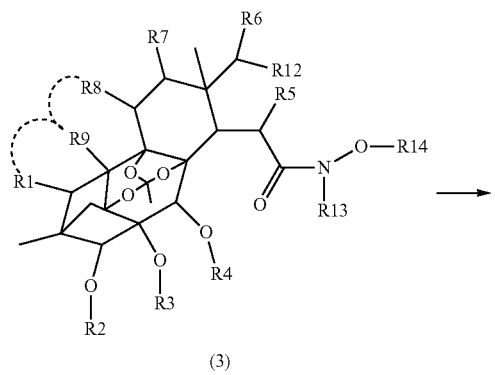
(3)

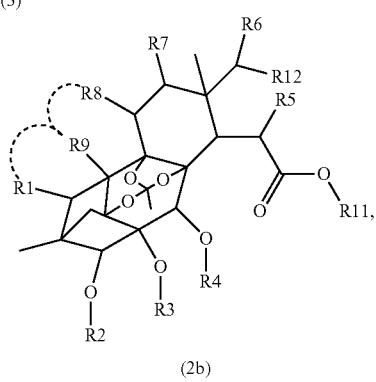
(2b)

as well as a more specific embodiment of this aspect of the invention is for obtaining the more specific compound (2bb) from compound (4dd) by exchanging starting compound (3) in the process of schema (V) with the compound (4dd) according to schema (Va):

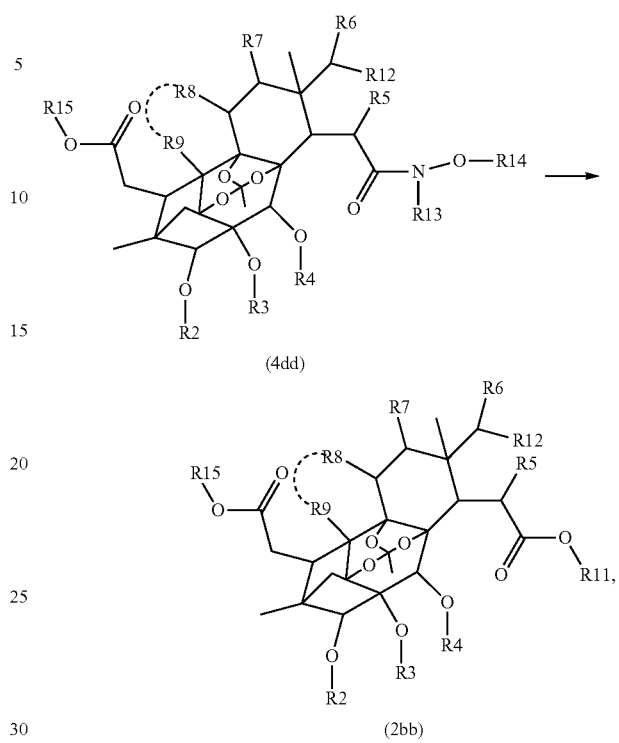
(4dd)

(2bb)

wherein in (3) and (2b) of schema (V) and (4dd) and (2bb) of schema (Va), R1 (when present) is preferably 2-methoxy-2-oxoethyl, R2 is preferably 2-methylbutyryl, pentanoyl, 2-ethylbutyryl, 2,3-dimethylbutyryl, 2-methylpentanoyl, 3-methylpentanoyl, hexanoyl, cyclohexanecarbonyl, with 2-methylbutyryl being most preferred, R3 is preferably hydrogen, acetyl or isobutyryl with hydrogen being most preferred, R4 is preferably hydrogen, acyl or isobutyryl with isobutyryl being most preferred, R5 is preferably hydrogen, R6 is preferably 3-furanyl, R7 is preferably hydrogen, R8 is preferably hydrogen, hydroxy or acetyloxy, with acetyloxy being most preferred, R9 is preferably methyl, R11 is preferably hydrogen or methyl, R12 is preferably hydroxy, oxo or acetyloxy with oxo being most preferred, R13 is preferably methyl, R14 is preferably methyl and R15 is preferably methyl [albeit substituents in (3), (2b), (4dd) and (2bb) can individually also be any of those defined further below in this DISCLOSURE section and claims amended herein, including with or without the rings denoted by hatched line], preferably by hydrolysis (deamidation) of (3) or (4dd) so as to form compound (2b) or (2bb) where R11 is hydrogen, which may then be followed by optional substitution of said hydrogen with another substituent R11 being different than hydrogen; e.g. by alkylation. Accordingly, combining schema (I) or (Ia) with schema (V) or (Va) allows a compound (2a) or (2aa) to be converted to a compound (2b) or (2bb), which is a highly desired embodiment of the invention as industrially desired compounds (2b) and (2bb) can then synthesized from readily available compounds (2a) or (2aa). Very specific embodiments of schema (Va) are given in Example 8.

In structures (1), (2), (2a), (2aa), (2b), (2bb), (3), (3a), (4), (4aa), (4bb), (4cc), (4dd), (4ee), (4ff), (4gg), (4hh), (5) and (5a) [i.e. structures (1) to (5)], R1 to R15 independently represents, when used herein, a substituent, connected by single or double bond, comprised from one to 40 atoms, and with less than 30 atoms preferred, and with less than 25 atoms more preferred, and with less than 20 atoms even more preferred, and with less than 18 atoms even more preferred, and with less than 15 atoms even more preferred, and with less than 12 atoms even more preferred, and with less than 9 atoms even more preferred, and with less than 6 atoms even more preferred with hydrogen, oxygen, carbon, sulfur, nitrogen, phosphorous and halogen atoms being preferred; where atoms are connected by single or double bonds so as to form a single linear, branched and/or cyclic structure, said substituent optionally preferably comprising zero heavy atom(s), at least 1 heavy atom, even more preferably at least 2 heavy atoms, even more preferably at least 3 heavy atoms, even more preferably at least 4 heavy atoms, and even more preferably at least 5 heavy atoms, and even more preferably at least 6 heavy atoms most preferably at least 9 heavy atoms, and where R14 may optionally be coupled to a resin via covalent bond, and/or in structures (1) to (5), R1 to R15 independently represents hydrogen, halogeno, oxo (=O), —$R^{16}$, —$N(R^{18})C(O)R^{19}$, —$NR^{20}R^{21}$, —$SR^{22}$, —$Si(R^{23})_3$, —$OC(O)R^{24}$, —$C(O)OR^{25}$, —$C(O)R^{26}$, —$C(O)NR^{27}R^{28}$, —$S(O)_2NR^{29}R^{30}$, aryl or heteroaryl (which aryl and heteroaryl groups are themselves optionally and independently substituted by one or more groups selected from halogeno and $R^{31}$) and $R^{16}$, $R^{17}$, $R^{18}$, $R^{19}$, $R^{20}$, $R^{21}$, $R^{22}$, $R^{23}$, $R^{24}$, $R^{24}$, $R^{26}$, $R^{27}$, $R^{28}$, $R^{29}$, $R^{30}$, $R^{31}$ is selected from H, alkyl, cycloalkyl, alkylene, aryl or heteroaryl, and where R14 may optionally be coupled to a resin via covalent bond, and where R1 to R15 preferably and independently from each other is anyone of (2-furanyl)(acetyloxy)-methyl, (3-furanyl)(acetyloxy)-methyl, (4-halogenobenzoyl)oxy-2-methylpropylidene, (acetyloxy)-(2-furyl)methyl, (acetyloxy)-(3-furyl)methyl, (acetyloxy)methyl, 1-acetyloxy-2-methoxy-2-oxoethyl, 1-acetyloxy-2-methylpropylidene, 1-halogenoacetyloxy-2-methylpropylidene, 1-hydroxy-2-methoxy-2-oxoethyl, 1-hydroxy-2-methylpropylidene, 1-hydroxyethylidene, 1-hydroxypropylidene, 1-methoxy-2-methoxy-2-oxoethyl, 1-methoxy-2-methylpropylidene, 1-methyl-1-methoxyethyl, 1-oxo-2-methoxy-2-oxoethyl, 2-(acetyloxy)-2-(2-furyl)ethyl, 2-(acetyloxy)-2-(3-furyl)ethyl, 2-alkoxy-2-oxoethyl, 2-butoxy-2-oxoethyl, 2-ethoxy-2-oxoethyl, 2-furanyl, 2-furoyl, 2-hydroxy-2-oxoethyl, 2-hydroxyisobutyryl, 2-isobutoxy-2-oxoethyl, 2-isopropoxy-2-oxoethyl, 2-methoxy-2-oxoethyl, 2-methyl-1-oxo-2-butenyl, 2-methyl-2-hydroxybutyryl, 2-methylbutyryl, 2-oxy-2-methyl-ethyl, 2-propoxy-2-oxoethyl, 2,3-dimethyl-2,3-dihydroxybutyryl, 2,3-dimethyloxirane-2-carbonyl, 2,3:4,5-diepoxy-2,3,4,5-tetrahydro-3-furanyl, 2,5-dihydro-5-acetyloxy-2-oxo-3-furanyl, 2,5-dihydro-5-hydroxy-2-oxo-3-furanyl, 3-furanyl, 3-furoyl, 3-hydroxy-3-oxopropionyl, acetyl, acetyloxy, alkylene, alkenyl, alkoxy, alkoxy-oxomethyl, alkyl, alkyryl, alkyryloxy, allyloxy, aryl, heteroaryl, benzyl, butenyl, butoxy, butoxy-oxomethyl, butyryl, butyl, butyryl, butyryloxy, dimethoxymethyl, ethenyl, ethoxy, ethoxy-oxomethyl, ethyl, halogen, halogeno, halogenoacetyl, halogenoacetyloxy, halogenoaryl, halogenoxo, halogenobenzyl, hydrogen, hydroxy, hydroxy-oxomethyl, hydroxyalkyl, hydroxybutyl, hydroxyethyl, hydroxyisobutyl, hydroxyispropyl, hydroxyl, hydroxymethyl, hydroxymethylene, hydroxypopyl, isobutenyl, isobutoxy, isobutoxy-oxomethyl, isobutyryl, isobutyryloxy, isopropenyl, isopropionyl, isopropionyloxy, isopropoxy, isopropoxy-oxomethyl, isopropyl, isopropynyl, methoxy, methoxy-oxomethyl, methoxymethyl, methyl, methylene, nicotinoyl, oxo, propenyl, propionyl, propionyloxy, propoxy, propoxy-oxomethyl, propyl, tert-butyl, tert-butyl-dimethylsilyl, triethylsilyl, trifluoroacetyl, vinyloxy, penatonyl, 2-ethylbutyryl, 2,3-dimethylbutyryl, 2-methylpenatonyl, 3-methylpentanoyl, hexanoyl, cyclohexanecarbonyl, cyclopentanecarbonyl, alkyloxy, benzyl, p-chlorobenzyl, p-bromobenzyl, connected heavy atom(s) substituted with hydrogens, and where R14 may optionally be coupled to a resin via covalent bond, and where for R1 a 2-methoxy-2-oxoethyl is being most preferred, and wherein R1 is optionally connected by covalent bond(s) to R9 so as to form ring(s), and where for R2 a hydrogen, acetyl, propanoyl, butyryl, isobutyryl, 2-methylbutyryl, pentanoyl, 2-ethylbutyryl, 2,3-dimethylbutyryl, 2-methylpentanoyl, 3-methylpentanoyl, 3-methylpentanoyl, hexanoyl, cyclohexanecarbonyl, cyclopentanecarbonyl is being more preferred, with an acetyl or isobutyryl being even more preferred, and with an isobutyryl being most preferred, and where for R3 a hydrogen or acetyl or isobutyryl is being more preferred, with a hydrogen or isobutyryl being even more preferred, and with a hydrogen being most preferred, and where for R4 a hydrogen, acetyl or isobutyryl or is being even more preferred, and with a hydrogen being most preferred, and where for R5 a hydrogen, isobutyryl or 1-hydroxy-2-methylpropylidene is being even more preferred, with a hydrogen being most preferred, and where for R6 a 3-furanyl, 3-furoyl or (3-furanyl)(acetyloxy)-methyl is being more preferred, with a 3-furanyl being most preferred, and where for R7 a hydrogen, hydroxy, methoxy, acetyloxy, isobutyryloxy and (acetyloxy)methyl is being more preferred, with a hydrogen being most preferred, and where for R8 a hydrogen, hydroxy, methoxy, acetyloxy, isobutyryloxy and (acetyloxy)methyl is being more preferred, with a hydrogen being most preferred, and wherein the substituent R8 is optionally connected to substituent R9 by covalent bond(s) so as to form ring(s), and where for R9 a hydrogen, methyl and acetyloxy being more preferred, with a methyl being most preferred, and wherein R9 is optionally connected to R1 and/or R8 by covalent bonds so as to form ring(s), and where for R10 a hydrogen, acetyl or isobutyryl being more preferred, with a hydrogen being most preferred, and where for R11 a methyl is being most preferred, and where for R12 an oxo, hydroxy or acetyloxy is being more preferred, with an oxo being most preferred, and where for R13 a methyl being most preferred, and where for R14 a methyl or tert-butyl is being more preferred, with a methyl being most preferred, and where for R15 an alkyl, methyl, or hydrogen is being more preferred, with a methyl being most preferred.

In structures (1) to (5), R1 to R31 could also be common protecting groups well-known for the person skilled in the art, and described in the following general references: Kocienski, P. J. Protecting Groups, 3rd ed.; Georg Thieme Verlag: New York, 2005 and Greene, T. W.; Wuts, P. G. M. Protective Groups In Organic Synthesis, 3rd ed.; John Wiley & Sons: New York, 1991. These references also describe the processes how to introduce a protective group using protective reagents as well as remove protective groups, processes which are well-known in the art, and also described in Smith and Smith, 2011; Warren and Wyatt, 2007, 2009.

In structures (1) to (5), R2 and/or R10 could also be absent (i.e. being comprised by no atom), the oxygen to which R2 and/or R10 otherwise would have been connected to then being attached to the remainder of anyone of the molecules (1) to (5) with a double bond.

Most embodiments of the present invention prefer R1 and R9 not to be connected to each other with covalent bond(s).

Most embodiments of the present invention prefer R9 and R8 not to be connected to each other with covalent bond(s).

It is further noted that it is possible to form a compound where R2 is connected to R3 with a covalent bond so as to form a ring, e.g. by appropriately attaching a protective group, as is well-known in the art, without any negative impact on any of the of the embodiments of the present invention being induced. Accordingly, any such modified compound of anyone of compounds (1) to (5) could be exchanged for the respective compound (1) to (5) for all aspects of the present invention.

It is further noted that it is possible to form a compound where R3 is connected to R4 with a covalent bond so as to form a ring, e.g. by appropriately attaching a protective group, without any negative impact on any of the of the embodiments of the present invention being induced. Accordingly, any such modified compound of anyone of compounds (1) to (5) could be exchanged for the respective compound (1) to (5) for most aspects of the present invention.

It is further noted that it is possible to form a compound where R7 is connected to R8 with a covalent bond so as to form a ring, e.g. by appropriately attaching a protective group, without any negative impact on any of the of the embodiments of the present invention being induced. Accordingly, any such modified compound of anyone of compounds (1) to (5) could be exchanged for the respective compound (1) to (5) for all aspects of the present invention.

It is further noted that a compound of anyone of structures (1) to (5) can be subjected to minor modification by the exchange of one, or two, or three hydrogens with methyl, hydroxy, halogeno, halogen, methoxy, or acetyloxy, or by the removal of a methyl group in the compound, exchanging it with a hydrogen, without having any negative impact on any of the of the embodiments of the present invention. Accordingly, any such modified compound of anyone of compounds (1) to (5) could be exchanged for the respective compound (1) to (5) for all aspects of the present invention.

In its most central part the invention provides the compound with structure (3). Compound (3) thus being the most preferred embodiment of the invention.

A further highly desired embodiment of the invention is the use of compound (3) [including (3a), (4), (4aa), (4bb), (4cc), (4dd), (4ee), (4ff), (4gg), (4hh)] in a process for synthesis of a compound derived from (3) [including from (3a), (4), (4aa), (4bb), (4cc), (4dd), (4ee), (4ff), (4gg) or (4hh)]. A more specific embodiment of this aspect of the invention provides the compound (3) [including (3a), (4), (4aa), (4bb), (4cc), (4dd), (4ee), (4ff), (4gg) and (4hh)] for use in a process for providing compounds with structure (5) [which includes the process for providing compounds with structure (1), (5a) and the compound of claim 40 in WO 2008/145996], the compounds (5), (5a) and (1), and those in claim 40 in WO 2008/145996, being highly desired compounds due to their sexual enhancing activity.

In a further highly desired embodiment, the invention provides the process to afford the compound with structure (3) from the compound with structure (2); i.e. either the compound with structure (2a) [including (2aa)] or (2b) [including (2bb)], with structure (2a) being preferred, and (2aa) being most preferred.

A yet a further highly desired embodiment the invention provides a process for affording a compound with structure (5) [including compound with structure (1), (5a) and the compound of claim 40 in WO 2008/145996] from a compound with structure (2); i.e. either a compound with structure (2a) [including (2aa)] or (2b) [including (2bb)], with (2a) being preferred, and with (2aa) being most preferred, by forming a compound with structure (3) [including optionally forming a compound with structure (3), (3a), (4), (4aa), (4bb), (4cc), (4dd), (4ee), (4ff), (4gg) or (4hh)] as an intermediate.

In a yet further highly desired embodiment, the invention provides a process for affording a further compound of structure (5) [including compound with structure (1), (5a) and the compound of claim 40 in WO 2008/145996] from a compound with structure (5) [including the compound with structure (1) and (5a) and the compound of claim 40 in WO 2008/145996] that has been directly obtained by the process of the invention, as defined in the previous paragraphs. An Example for this is provided in Example 3 by the conversion of 20 to compound 21, 20 being originally obtained from phragmalin by the process of the invention.

A yet further embodiment of the invention provides the process of affording a compound with structure (2b) or (2bb) from a compound with structure (3) [including from (4), (4aa), (4bb), (4cc), (4dd), (4ee), (4ff), (4gg), (4hh) or (3a)].

A yet further embodiment, the invention provides the process of affording a compound with structure (2b) [including (2bb)] from a compound with structure (2a) [including (2aa)], by forming a compound with structure (3) [including optionally forming a compound with structure (4), (4aa), (4bb), (4cc), (4dd), (4ee), (4ff), (4gg), (4aa) or (3a)] as an intermediate.

In structures (1) to (5) anyone of R1 to R31, in particular R14, can be coupled to a resin or other high molecular weight component by covalent bond(s), which may in particular be desired as part of the invention in its use for synthesis of compounds complying with structures (1), (2b), (2bb), (3), (3a), (4), (4aa), (4bb), (4cc), (4dd), (4ee), (4ff), (4gg), (4hh), (5a) or (5) or the compound of claim 40 in WO 2008/145996.

BEST MODE

Weinreb amides with structure (3) [including its variations (3a), (4), (4aa), (4bb), (4cc), (4dd), (4ee), (4ff), (4gg) and (4hh), which for sake of this patent are automatically included in (3) whenever appropriate from a chemical point of view] have been found to be highly useful to afford the desired product with structure (5) [including its variation (1) and (5a), which for the sake of this patent is automatically included in (5) whenever appropriate from a chemical point of view] and even structure (2b) [including its variation (2bb), which for the sake of this patent is automatically included in (2b) when appropriate from a chemical point of view]. The invention therefore provides the Weinreb amide (3), irrespectively of its mode of preparation. In a process where a Weinreb amide (3) is used to form a structure (5) or (2b), the Weinreb amide (3) may prior to the inclusion in said process have been isolated in purified form (i.e. being "pure"; viz. being an essentially pure compound), or it may exist as an intermediate in a mixture (i.e. being in non-purified form; viz. being "impure"), the latter as would be the case if (3) was formed from a precursor capable of forming Weinreb amide (3) in a reaction mixture without isolating (3). Preferred embodiments of the invention apply Weinreb amide (3) in a purified form into a process of chemical reaction or for induction of aggression by administration to an animal or even to a human in therapy.

Weinreb amide (3) where R13 and R14 is methyl can be prepared from the appropriate starting compound by processes well known in the art using amidolytic reagents, the amidolytic reagent preferably being MeNHOMe.HCl, as is well known in the art, starting from e.g. carboxylic acids (i.e. R11 being H in compound (2b)) (e.g. as described in Niu et al., Organic Letters, 2009, vol. 11, No. 19, 4474-4477 and in references therein), acid chlorides [i.e. —O—R11 being Cl in compound (2b)] (e.g. as described in Nahm and Weinreb, Tetrahedron Lett. 1981, vol. 22, No. 39, 3815-3818; Jaipuri et al. Tetrahedron Lett., 2004, 45, 4149-4152), lactones [i.e. as in compound (2a)] (e.g. as described in Shimizu et al., Tetrahedron Lett., 1997, 38, 2685-2688; Jaipuri et al. Tetrahedron Lett., 2004, 45, 4149-4152 and as described below), esters [e.g. R11 in compound (2b) being alkyl, alkylene, aryl or heteroaryl, or e.g. R11 in compound (2b) being as defined for R15 above] (e.g. as described in Shimizu et al., Tetrahedron Lett., 1997, 38, 2685-2688; Sha et al., J. Org. Chem. 2002, 67, 831-836; Colobert et al. Org. Lett. 2002, 4, 1723-1725), amides [i.e. —O—R11 in compound (2b) being substituted by —NR$^{20}$R$^{21}$; —NR$^{20}$R$^{21}$ being as defined above] (e.g. as described in Dineen et al., J. Am. Chem. Soc., 2006, 128, 16406-16409) and anhydrides [i.e. R$^{11}$ in (2b) being —C(O)R$^{26}$ as defined above](e.g. as described in Jacobi et al., Tetrahedron Lett., 1984, vol. 25, No. 42, 4859-4862).

While in structure (3) most preferred is methyl for both substituents R13 and R14, the synthesis of Weinreb amides with other substituents are well known in the art. For example Chernega et al. (Chernega, A N et al. Organic Letters, 2009, vol. 11, No. 15, 3254-3257) describe a process for synthesis of Weinreb amides (e.g. chiral equivalents), which can be used to synthesize structure (3) where R13 is 1-(1'-naphthyl) ethyl and R14 is tert-butyl, using as amidolytic reagent N-1-(1'-naphthyl)-ethyl-O-tert-butylhydroxylamine.

Another approach for synthesis of Weinreb amides is described by Salvino et al. (Salvino, J M et al. J. Org. Chem., 1999, 64, 1823-1830) which can be used to synthesize structure (3) where R13 is benzyl, p-chlorobenzyl, or p-bromobenzyl and R14 is methyl-phenoxymethylcopoly-(styrene-1%-divinylbenzene)resin (preferably 100-200 Mesh) (i.e. R14 of compound (3) being coupled to a solid resin support). Solid phase synthesis is a method well known in the art, which can be used for the sake of the present patent.

Yet another approach for synthesis of Weinreb amides is described by Hirner and Somfai (Hirner, S and Somfai, P, J. Org. Chem., 2009, 74, 7798-7803) which can be used to synthesize structure (3) where R13 is methyl and R14 is tert-butyl or methyl.

Yet another approach for synthesis of Weinreb amides is described by Labeeuw et al. (Labeeuw, O et al. Tetrahedron Lett, 2004, 45, 7107-7110) that can be used to synthesize structure (3) where R13 is methyl and R14 is tert-butyl.

Naturally thus structure (3) can be synthesized where R13 and R14 is any suited substituent, although for the present invention methyl is preferred for R13 as well as methyl is preferred for R14.

The Weinreb amide (3) can be obtained using MeNHOMe.HCl, e.g. together with additive (additional reagent) Me$_2$AlCl (Shimizu et al., Tetrahedron Lett., 1997, 38, 2685-2688) or trimethylaluminium (Me$_3$Al); however MeNHOMe.HCl can be substituted with other amidolytic reagent, well known in the art, such as e.g. N-methyl-O-tert-butylhydroxylamine hydrochloride (Hirner, S and Somfai, P, J. Org. Chem., 2009, 74, 7798-7803; Labeeuw, O et al. Tetrahedron Lett, 2004, 45, 7107-7110) or N-1-(1'-naphthyl)-ethyl-O-tert-butylhydroxylamine (Chernega, A N et al. Organic Letters, 2009, vol. 11, No. 15, 3254-3257). Moreover, the additive (additional reagent) trimethylaluminium (Me$_3$Al) is optional and can be excluded or substituted with other additives (additional reagents) such as dimethylaluminium chloride (AlMe$_2$Cl), sodium hydride (NaH), n-butyllithium (n-BuLi), methylmagnesium bromide (MeMgBr), or diisobutylaluminium hydride (DIBAL-H) or other additives (additional reagents), in particular those described in Labeeuw, O et al. Tetrahedron Lett., 2004, 45, 7107-7110; Shimizu et al., Tetrahedron Lett., 1997, 38, 2685-2688; Hirner, S and Somfai, P, J. Org. Chem., 2009, 74, 7798-7803; Chernega, A N et al. Organic Letters, 2009, vol. 11, No. 15, 3254-3257.

However, in the most preferred embodiment of the invention a lactone of structure (2a) is converted to the Weinreb amide (3) using O-dimethylhydroxylamine hydrochloride (N,O-dimethylhydroxylamine hydrochloride; MeNHOMe.HCl), promoted by the presence of trimethylaluminium (Me$_3$Al) as additive. Specific embodiments for this process are given in Examples 1 to 3. As has already been pointed out above the conditions for this reaction was surprisingly distinct, practically excluding other methods for formation of the desired Weinreb amide (3). Moreover, as already pointed out above the formation of the Weinreb amide could be afforded in a chemoselective/regioselective manner affecting only the lactone cycle, but not ester at carbon 7, again practically excluding other methods for formation of the Weinreb amide. All these features contribute separately as well as combined very important inventive steps for this invention.

The most highly preferred embodiment of the invention starts from phragmalin, a structure complying with structure (2a):

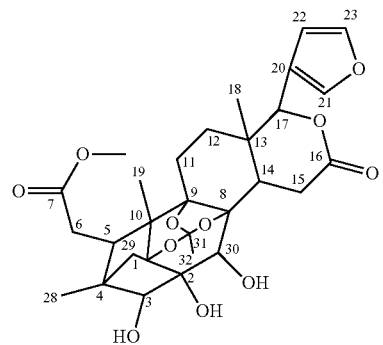 [SMILES: COC(=O)CC1C2(C)CC34OC5(C)OC6(C7CC(=O)OC(c8ccoc8)C7(C)CCC6(O5)C13C)C(O)C4(O)C2O]

Phragmalin (herein also called compound 6) is readily available from many sources, as is well known in the art, and can be prepared using methods well known in the art, e.g. as described (R. R. Arndt and W. H. Baarshers, Tetrahedron, 1972, 28, 2333-2340; J. D. Connolly at al, J. C. S. Perkin I, 1978, 285-288). Specific examples how to get compounds of structure (3) from phragmalin using MeNHOMe.HCl as amidolytic agent is given in Examples 1 to 3 (i.e. for obtaining compounds 7, 8, 14, 15, 18 and 19).

However, any other phragmalin-like compound with structure (2a) or (2b) can be used as starting point for the process which include (but is not limited to) xyloccensin E, xylocarpin I, kotschyins, phragmalins, swietenialides, leandreanins, neobeguins, pseudrelones, busseins, chukrasins, tabulalides, swietenitins, compounds with CAS (Chemical Abstracts Service) Registry numbers 1299464-67-7, 1267877-55-3, 1248571-24-5, 1219132-70-3, 1214981-83-5, 1214976-20-1, 1186131-42-9, 1126643-44-4, 1126643-43-3, 1126643-42-2, 1053209-52-1, 1045017-87-5, 1038746-45-0, 952615-91-7, 910578-31-3, 803723-28-6, 803723-27-5, 561307-83-3, 260794-07-8, 116408-24-3, 115391-10-1, 115367-50-5, 98401-23-1, 98379-64-7, 98379-62-5, 98379-61-4, 98379-60-3, 98379-59-0, 98379-58-9, 98379-57-8, 96386-37-7, 90955-39-8, 90931-03-6, 90931-02-5, 90931-01-4, 90931-00-3, 90930-99-7, 90930-98-6, 90930-97-5, 90930-96-4, 90930-95-3, 81584-75-0, 67931-05-9, 67931-04-8, 67904-58-9, 67904-57-8, 67904-56-7, 67904-55-6, 67904-54-5, 67904-53-4, 67895-40-3, 67895-39-0, 67895-38-9, 66939-94-4, 66901-32-4, 66901-31-3, 66901-30-2, 66884-81-9, 66884-80-8, 66884-79-5, 66884-78-4, 66884-77-3, 66495-42-9, 66451-22-7, 52724-62-6, 52681-81-9, 41508-26-3, 41060-14-4, 41060-13-3, 40185-37-3, 40185-36-2, 40185-34-0, 40185-33-9, 38575-45-0, 37832-02-3, 37665-93-3, 37665-92-2, 37665-91-1, 37665-90-0, 35183-64-3, 35055-81-3, 939775-81-2, 1173892-10-8, 1173892-09-5, 1173892-08-4, 1173892-07-3, 1173892-06-2, 1173892-05-1, 1173892-04-0, 1173892-03-9, 1169770-19-7, 1169770-18-6, 1169770-17-5, 1159493-38-5, 1159493-37-4, 1159493-36-3, 1159493-35-2, 1159493-34-1, 1159493-33-0, 1088920-97-1, 1088920-95-9, 1088920-93-7, 1088920-91-5, 1088920-89-1, 1088920-87-9, 1088920-85-7, 1088920-83-5, 1088920-81-3, 1088920-69-7, 1088920-67-5, 1088920-65-3, 1088920-63-1, 1088920-61-9, 1088920-59-5, 1088920-57-3, 1088920-55-1, 1088920-53-9, 1088920-51-7, 1088920-49-3, 1088920-47-1, 1088920-44-8, 1088920-42-6, 629654-42-8, 629654-41-7, 926896-45-9, and any other compound being member of the general structure (2a) or (2b) such as the one which obtained by synthesis, e.g. applying procedures along the lines described by Lebold et al., 2012. For the sake of the present patent a structure (2a) or (2aa) is preferred over a structure (2b) or (2bb) as starting material for synthesis of structure (3). Most preferred is a structure (2aa).

The process (III) [including for all aspects of this invention the more specific variations (IIIa) and (IIIb)] of the invention provides intramolecular lactonization, for which in a highly preferred embodiment of the invention the Weinreb amide of structure (3) is converted to a lactone with structure (5) as shown in Scheme (III) by the reaction of deamidation (i.e. hydrolysis using basic conditions) followed by intramolecular ring closure forming the lactone by methods well known in the art, e.g. using condensation reagent for formation of lactone cycle such as 1-ethyl-3-(3-dimethylaminopropyl)carbodiimide (EDCI), N,N'-dicyclohexylcarbodiimide (DCC), bis(2-oxo-3-oxazolidinyl)phosphonic chloride (BOPCl), O-(7-azabenzotriazol-1-yl)-N,N,N,N-tetramethyluronium hexafluorophosphate (HATU), 2-chloro-1-methylpyridinium iodide (Mukaiyama reagent), or mixed anhydride method (Chen et al., 1987), with EDCI being preferred. An example for this aspect of the invention is the conversion of compound 8 to compound 9 as described in Example 1; see in particular Scheme 1 of Example 1.

Another specific embodiment of process (III) of the invention comprises the transformation of the Weinreb amide to lactone by using Lewis acid, e.g. by use of trimethylsilyl trifluoromethanesulfonate (TMSOTf), boron trifluoride diethyl complex ($BF_3.Et_2O$), aluminium triethanolate (Al(OEt)$_3$), zinc trifluoromethane-sulfonate (Zn(OTf)$_2$), iron(II) acetate (Fe(OAc)$_2$), iron(III) acetate (Fe(OAc)$_3$), iron(III) chloride (FeCl$_3$), copper(I) chloride (CuCl), copper(II) trifluoromethane-sulfonate (Cu(OTf)$_2$), magnesium chloride (MgCl$_2$), magnesium methylate (Mg(OMe)$_2$), magnesium trifluoromethanesulfonate (Mg(OTf)) and other related metal salts, hydroxides and alkoxides. The lactonisation can also be afforded using bases such as potassium carbonate (K$_2$CO$_3$), caesium carbonate (Cs$_2$CO$_3$), n-butyllithium (n-BuLi), lithium bis(trimethylsilyl)amide (LiHMDS), sodium bis(trimethylsilyl)amide (NaHMDS), as would be evident to anyone skilled in the art; the trimethylsilyl trifluoromethanesulfonate (TMSOTf) being the preferred reagent. Specific embodiments of this aspect of the invention is shown by the conversion of compound 15 to compound 16 in Example 2, and the conversion of compound 19 to compound 20 in Example 3.

In the case of using a compound (2a) or (2b) where R2 is H (hydrogen) as a starting material for the synthesis of compounds (3) [eventually followed by the synthesis of a compound (5)] a preferred route for the synthesis starts with protecting the hydroxy group at carbon 3 in compound (2a) or (2b) [the carbon numbering being marked in structure (2a) and (2b) above] by a protective group or by acylation, to afford protection (e.g. in particular in the case that a subsequent step involves oxidation), which is then followed by the formation of Weinreb amide according to schemes (I), (Ia), (II) or (IIa), which is subsequently followed by the ring closure according to schema (III), (IIIa) or (IIIb). Indeed it was found that the hydroxy group at carbon 3 [i.e. the case that R2 is H in a compound (2) or (3)] was sensitive to oxidation (e.g. when using Dess-Martin perodinane for oxidation, as described in Example 2 for the oxidation of compound 14 to compound 15), so that in the unprotective form for the hydroxy group at carbon 3 of a compound (2) or (3) the oxidation resulted in the destruction of the phragmalin skeleton into non-desired structures. Specific examples of affording protection of a hydroxy group at this position 3 are the acylations provided in Examples 2 and 3 in the conversions of compound 6 to compound 13, and compound 6 to compound 17.

In the case of using a compound (2a) or (2b), where both R2 and R4 is H (hydrogen), as starting material for synthesis of a compound (5) via a compound (3), a key inventive step provided by the present patent is the regioselective protection of the secondary hydroxy group at carbon 3 in a compound (2a) or (2b) to provide a further compound (2a) or (2b), while leaving the secondary hydroxy group at carbon 30 in compound (2a) or (2b) untouched. This key step was demonstrated in Examples 2 and 3 by the selective acylations of compound 6 at carbon 3 to provide compound 13 or compound 17. This is a key inventive step, as it subsequently allows the so obtained protected compound (2) to be converted to the desired compound (5) via the intermediate compound (3) by ring closing so as to form the lactone ring of compound (5). Suited conditions for selective protection of a free hydroxy group at position 3 in a compound (2a) or (2b) are evident from Examples 2 and 3, but are not limited to these conditions; other conditions well known in the art for introduction of protective group or acylation can be used (e.g. those described in Smith and Smith, 2011; Warren and Wyatt, 2007, 2009); this is because primarily the regioselectivity is afforded in a surprising way by the intrinsic properties of the compound (2) or (3) (i.e. not by the particular method applied), in a manner that was not foreseeable by prior art (i.e. here provided as a discovery), and is thus an important inventive step in the overall conversion of a compound (2a) or (2b) to a compound (5) via the intermediate (3).

Introducing a protective group or acylation at carbon 3 in compound (2a) or (2b) is preferred prior to the formation of compound (3), over introducing the protective group or performing the acylation in a compound (3). This is because attempts to protect the free hydroxy group at carbon 3 of compound 7 in Example 3 by isobutyrylation to afford compound 18 resulted in a low yield with formation of many side products.

A further important inventive step is the method for selective oxidation or the protection of the hydroxy group at carbon 17 in a compound (3) where R12 is hydroxy, over a free hydroxy group at carbon 30, when R4 in compound (3) is hydrogen [atom numberings of the phragmalin skeleton in (3) being identical as in (2a)], as is exemplified in Example 2 and 3 by the selective oxidation of the hydroxy group at carbon 17 to keto, while leaving the hydroxy group at carbon 30 untouched in the conversion of compound 14 to compound 15, and in the conversion of compound 18 to compound 19, as well as in the regioselective protection of the hydroxy group at carbon 17 over the hydroxy group at carbon 30 in the conversion of compound 7 to compound 8 of Example 1. This is indeed a key inventive step in the present patent as this makes it possible to provide a further compound (5) by intramolecular lactonization where R12 is oxo, which results in a highly desired compound for treatment of sexual dysfunction as is evident from WO 2008/145996. It shall be observed that for the case that both carbon 17 and 30 are substituted with non-protected hydroxy groups, the lactone ring is closed at the non-desired carbon 17 during the lactonization process, rather than at the desired carbon 30. This thus again shows that the selective oxidation or protection of a hydroxy group at carbon 17 is a key inventive step in the present patent. It shall be further noted that the regioselective oxidation of the hydroxy function at carbon 17 over the hydroxyfunction at carbon 30 is not limited to the conditions given in Examples 2 and 3; other processes for oxidation, well known in the art, can be used as well (e.g. those described by Smith and Smith, 2011; Warren and Wyatt, 2007, 2009). This is because the regioselectivity is afforded in a surprising way by the intrinsic properties of the compound (3) in a manner that is not foreseeable by prior art, but not by the specific reagent or process for oxidation used, which this patent provides as a discovery.

Specific examples for the most preferred route of synthesis, when starting from a phragmalin compound are given in Examples 2 and 3, where the hydroxy group at carbon 3 of phragmalin is first selectively acylated to afford protection; the acylation starting at phragmalin in order to afford the highest yield. The compound is then converted to a Weinreb amide using a Lewis acid, which yields a compound with a hydroxy group at carbon 17 (c.f. compounds 14 and 18). This compound is then selectively oxidized at the hydroxy group at carbon 17, forming a keto group at carbon 17. The lactone ring is subsequently closed in the desired position to form a compound with the structure (1).

Acylation of the hydroxy group at carbon 3 in (2a), (2b) or phragmalin, can be done using any acylating agent well known in the art, such as by use of acetic anhydride, acetylchloride, isobutyric anhydride, isobutyric chloride, or other acid anhydrides or chlorides. Specific examples for the use of acetic anhydride, isobutyric anhydride and isobutyric chloride for the regioselective protection of the hydroxy group at carbon 3 are given in Examples 2 and 3.

The hydroxy group at carbon 3 can also be protected with any type of protecting group, using protective reagent, well know for the person skilled in the art (e.g. as described in Smith and Smith, 2011; Warren and Wyatt, 2007, 2009).

For the case that in compound (3), R12 is hydroxy it is often more desired that this hydroxy group is selectively converted to a keto-function via oxidation, which can also be afforded in a regioselective manner as shown in Examples 2 and 3. This is advantageous as it allows a ring closure with a free hydroxy group at carbon 30 at a following step, as also shown in Examples 2 and 3, which results in the most desired variants of structure (5) wherein R12 is oxo. Another possibility to protect a free hydroxy group at carbon 17 with a protective group, which can be afforded by the invention in a regioselective manner, using a protective reagent, as demonstrated in Example 1. This can then also afford a route for ring closure with a free hydroxy group at carbon 30 at a following step, as is also demonstrated in Example 1.

The invention encompasses processes of synthetic schemes (I), (Ia), (II), (IIa), (III), (IIIa), (IIIb) (IV), (IVa), (V) and (Va), and processes P1, P2 and P3 of which anyone have been optimized with respect to the yield of production of anyone of compounds (1), (2a), (2aa), (2b), (2bb), (3), (3a), (4), (4aa), (4bb), (4cc), (4dd), (4ee), (4ff), (4gg), (4hh), (5) and (5a) or anyone of the compounds mentioned in Examples 1 to 3 or in the claims amended herein or the compounds of claim 40 of WO 2008/145996; such optimized processes being possible to afford for anyone skilled in the art, stated the teachings provided by this invention.

Aggression Inducing Effect of Compound (3)

A yet further embodiment of the invention provides compound (3) for eliciting a biological effect in a living organism. Very surprising the compound (3) of the invention elicits aggressive behavioral effects when administered to an animal capable of showing aggressive behavior; i.e. compound (3) is an aggression inducing compound. This is clearly demonstrated in Example 4.

It is a remarkable property of a compound to induce aggression on peripheral administration into the body of an animal (in particular the induction of aggression of a male directed to a female), i.e. when the administration is done outside of the central nervous system (i.e. a peripheral administration), as is demonstrated in Example 4 for the subcutaneous administration of 19 (LG-1725) (LG-1725 being provided as described in Example 3) into mice. Such unprecedented induction of marked aggressive behavior in a male directed to a female upon the peripheral administration of a chemical into the male seems to be unique, as well as it seems to be a unique feature of (3) to be capable of inducing aggression on peripheral administration; previously known compounds of various types capable of inducing aggression could induce the aggression only when introduced directly into (regions of) the brain (see Miczek et al., 1994; de Boer and Koolhaas, 2005; Olivier and Oorschot, 2005; de Almeida et al., 2005; and references therein; aggressive behavioral patterns in animals, in particular mammals, are well known among those skilled in the art; methods for their study are given in the cited references, and in the references cited in these references).

The study of aggression is an important scientific field, and aggressive behavior among humans has very large socio-economic impact. The compound (3) of the invention has therefore a large value for studying the biological and molecular mechanisms underlying aggressive behavior. Accordingly the present patent provides the use of compound (3) for eliciting aggression (or other biological effect) in an animal, preferably a mammal (including even a human), e.g. as an experimental tool in vivo, or otherwise for use in in vitro to explore mechanisms of aggressive behavior, and even in therapy. The most important embodiment of this aspect of the invention is compound 19 (LG-1725) but other variants of (3) can be used as well.

It is further contemplated that the aggression inducing effect of compound (3) and its variants described herein is useful for treating of psychiatric and/or neurological conditions. Many psychiatric conditions relate to both increased and decreased anger and aggression. This includes schizophrenia, bipolar disorders, schizoaffective disorder, posttraumatic stress disorder, mania, depression, substance abuse, anxiety disorder, phobias, generalized anxiety disorder, social anxiety disorder, panic disorder, agoraphobia, obsessive-compulsive disorder, post-traumatic stress disorder, psychotic disorder, delusional disorder, personality disorders including antisocial, borderline, histrionic or narcissistic personality disorders, eating disorders (including anorexia nervosa, bulimia nervosa, exercise bulimia and binge eating disorders), sexual disorders (including sexual and gender identity disorders, dyspareunia, gender identity disorder, and ego-dystonic homosexuality and paraphilia), dissociative identity disorder, such as depersonalization disorder or Dissociative Identity Disorder, multiple personality disorder, memory or cognitive disorders (including amnesia and dementia), developmental disorders [including autism, spectrum disorders, oppositional defiant disorder, conduct disorder, and attention deficit hyperactivity disorder (ADHD)]. Moreover included are also neurasthenia, anti-aggressive behavior, self-defeating personality disorder, sadistic personality disorder, passive-aggressive personality disorder and premenstrual dysphoric disorder. Compound (3) and its variants can accordingly be used for treatment of said list of psychiatric conditions as well as for treatment of neurologic conditions.

Use of Compound (3) for Synthesis of a Compound (2b), Preferably Starting from a Compound (2a)

While compounds with structure (2b) are present in nature they are of a limited chemical variability as to their substituents R1 to R9, R11, and R12. However, some compounds pertaining to structure (2b) were isolated form natural sources and shown to have interesting pharmacological properties. [In fact those that were isolated were limited to the more narrow structure (2bb)]. This includes compounds with antiprotozoal activities (Hay et al, 2007) and antifeedant activities in insect larvae (Nakatani et al., 2004), and compounds with CAS registry numbers 1173892-10-8, 1173892-09-5, 1173892-08-4, 1173892-07-3, 1173892-06-2, 1173892-05-1, 1173892-04-0, 1173892-03-9, 1169770-19-7, 1169770-18-6, 1169770-17-5, 1159493-38-5, 1159493-37-4, 1159493-36-3, 1159493-35-2, 1159493-34-1, 1159493-33-0, 1088920-97-1, 1088920-95-9, 1088920-93-7, 1088920-91-5, 1088920-89-1, 1088920-87-9, 1088920-85-7, 1088920-83-5, 1088920-81-3, 1088920-69-7, 1088920-67-5, 1088920-65-3, 1088920-63-1, 1088920-61-9, 1088920-59-5, 1088920-57-3, 1088920-55-1, 1088920-53-9, 1088920-51-7, 1088920-49-3, 1088920-47-1, 1088920-44-8, 1088920-42-6, 629654-42-8, 629654-41-7, 926896-45-9, 926896-45-9.

Due to the interesting biological/pharmacological properties of compounds (2b) it is of high interest to be able to provide novel such compounds with larger variability in their substituents. Moreover, the compounds (2b) isolated earlier were present in only small quantities in plant tissues and it is desired to be able to produce them in large quantities for therapeutic, agricultural and industrial purposes, and other purposes as well.

The present patent provides a process wherein a compound (2a) or (2aa) which are present in large quantities in some species of Meliaceae can be converted to a compound (3), (3a), (4), (4aa), (4bb), (4cc), (4dd), (4ee), (4ff), (4gg) and (4hh) according to schema (I), (Ia), (IV) and combinations thereof, the compound (3), (4), (4aa), (4bb), (4cc), (4dd), (4ee), (4ff), (4gg) or (4hh) thereafter being converted to (2b) or (2bb) according to schema (V) or (Va). Naturally, this process can take advantage of all inventive steps described herein, including the chemoselective conversion of (2aa) to Weinreb amide at carbon 16, the regioselective oxidation of the hydroxy function at carbon 17, the regioselective deprotection of the hydroxyfunction at carbon 3 (c.f. the regioselective deprotection in conversion of compound 8 to 9 in Example 8), chemoselective acylation of a free hydroxyfunction at carbon 3 (see Examples 1 to 3); the latter acylation preferably being done on any of compounds (2a) or (2aa) prior to the conversion to Weinreb amide; however the acylation step at carbon 3 also being possible to perform after the conversion of (2a) or (2aa) to the Weinreb amide. A very specific embodiment of this process is given in Example 8 where hydrolysis of compound 8 [obtained from a compound of type (2aa), namely phragmalin] with potassium tert-butoxide (t-BuOK) or 10 M aqueous KOH gives compound 22, 22 subsequently being converted to its methyl ester, compound 23, using $CH_2N_2$ in diethyl ether or methyl iodide ($CH_3I$) as alkylating agents.

Moreover, naturally it is evident from the disclosures herein that any compound (2b) or (2bb) can be converted to another compound (2b) or (2bb), using a compound (3) as intermediate, which this patent thus provide as an additional feature.

For the sake of the present invention for the aspect of the invention of this section it is preferred to produce a structure (2b) or (2bb) where R1 is preferably 2-methoxy-2-oxoethyl, R2 is preferably hydrogen, acetyl, propanoyl, butyryl, isobutyryl, 2-methylbutyryl, pentanoyl, 2-ethylbutyryl, 2,3-dimethylbutyryl, 2-methylpentanoyl, 3-methylpentanoyl, 3-methylpentanoyl, hexanoyl, cyclohexanecarbonyl, cyclopentanecarbonyl, with 2-methylbutyryl being most preferred, R3 is preferably a hydrogen, acetyl, propanoyl, butyryl, isobutyryl, 2-methylbutyryl, pentanoyl, 2-ethylbutyryl, 2,3-dimethylbutyryl, 2-methylpentanoyl, 3-methylpentanoyl, 3-methylpentanoyl, hexanoyl, cyclohexanecarbonyl, cyclopentanecarbonyl, with a hydrogen being most preferred, R4 is preferably a hydrogen, acetyl, propanoyl, butyryl, isobutyryl, 2-methylbutyryl, pentanoyl, 2-ethylbutyryl, 2,3-dimethylbutyryl, 2-methylpentanoyl, 3-methylpentanoyl, 3-methylpentanoyl, hexanoyl, cyclohexanecarbonyl, cyclopentanecarbonyl, with an isobutyryl being most preferred, R5 is preferably a hydrogen, isobutyryl or 1-hydroxy-2-methylpropylidene, with a hydrogen being most preferred, R6 is preferably a 3-furanyl, R7 is preferably a hydrogen, hydroxyl, hydroxy, methoxy, acetyloxy, isobutyryloxy and (acetyloxy)methyl, with a hydrogen being most preferred, R8 is preferably a hydrogen, hydroxyl, hydroxy, methoxy, acetyloxy, isobutyryloxy and (acetyloxy)methyl, with an acetyloxy being most preferred, R9 is preferably hydrogen, methyl and acetyloxy, with a methyl being most preferred, R11 is preferably a methyl, R12 is preferably a hydrogen, oxo, hydroxy or acetyloxy, with an oxo being most preferred, and R15 is preferably a methyl. However, substituents can individually be as disclosed in the above DISCLOSURE section and in the claims amended herein, as well.

Because of the fact that the process of the present invention is capable of providing novel previously never before synthesized compounds, the present invention claims the compound (2b) of the invention, more preferably the compound (2bb) of the invention (with substituents defined in the previous paragraph) which is directly obtained by the process of the invention, preferably the process of the invention that proceeds with the process according to schema (I) or (Ia) (followed by optional intermediate steps) prior to the process according to schema (V) or (Va), preferably said process proceeding in high yield.

The present patent accordingly prefers any compound of structure (2b) or (2bb), which is produced with the process of the invention with a yield of more than 50 g/ton, even more preferably more than 100 g/ton, even more preferably more than 150 g/ton, even more preferably more than 180 g/ton, even more preferably more than 250 g/ton, even more preferably more than 390 g/ton and most preferably more than 450 g/ton of starting dried plant material. This claim is clearly supported from the computations of yields given below:

Yield of Compound (2b)

Based on the yields given in Examples 8 and Example 6 (an taking into account molecular weights of the compounds involved and the purity of starting compound phragmalin) the overall yields of compounds from Examples 8 complying with structure (2b) from 1 ton of dried *Chukrasia tabularis* seeds can be calculated as follows:

| Compound | Overall yield from 1 ton of seeds |
|----------|-----------------------------------|
| 22       | 726 g                             |
| 23       | 685 g                             |

Sexual Enhancing Effect of GL-1203, SAE6 and SAE5

The sexual enhancing effect of GL-1203, SAE6 and SAE5 were demonstrated in Example 5, essentially using the procedures detailed in WO 2008/145996. All three compounds showed a sexually enhancing effect as defined herein (as well as in WO 2008/145996, page 11), i.e. the increase in mounts for all of GL-1203, SAE6 and SAE5 exceeding 50% (even exceeding 75%) over the controls at the appropriate dose(s) given.

It shall be noted that GL-1203, SAE6 and SAE5 are novel compounds never before synthesized, which can be obtained by the processes described in the present patent. Moreover, the known compound R306 with sexually enhancing activity can also be obtained, as demonstrated in Example 3. Therefore GL-1203, SAE6, SAE5 and R306 are extremely important sexual enhancing compounds of the invention, which can be obtained directly by the process of the invention.

Comparison of the Efficiency of the Current Process to Obtain Compounds of Structure (5) or (1) with Previously Known Procedures Example 6 demonstrates that the raw material phragmalin used in the synthesis of GL-1203, SAE6, SAE5 and R306 can be obtained from commercially obtained dried *Chukrasia tabularis* seeds in quantities of 3.52 kg per ton of seeds at 95% purity. Examples 1 to 3 demonstrate that GL-1203, SAE6, SAE5 and R306 can be obtained from phragmalin with overall yields 4.14, 5.33, 15.48 and 14.55%, respectively. From these data (and the known molecular weights of the compounds involved, as well as taking into account the 95% purity of the starting material, phragmalin) it can be calculated that from one ton (1000 kg) of *Chukrasia tabularis* seeds we can get, respectively, 389, 191, 613 and 639 grams of, respectively, GL-1203, SAE6, SAE5 and R306, i.e. these being compounds complying with structure (5) of this patent. The purity of the obtained compounds are high, as demonstrated for SAE5 by analytical HPLC in Example 3; the purity of SAE5 approaching 100%.

The previously known processes to obtain the compound of structure (5) [as well as structure (5a) and (1), as well as those of claim 40 of WO 2008/145996] of the present invention are as follows:

i) The isolation of compound R306 in WO 2008/145996 from the roots of *Neobeguea mahafalensis* Example 41 of WO 2008/145996 shows that 12 mg of pure R306 ("Grade 3") was obtained from 722 grams of dried *Neobeguea mahafalensis* roots; thus 1 ton of roots would give 17 grams of R306 according to this process, which is substantially less effective than the present process which gives 639 grams for R306 per ton of starting material. Another process of WO 2008/145996, described in its Example 42, was even less efficient and gave only 1.2 mg of pure R306 from 124 g of roots of *Neobeguea mahafalensis* (see page 148 of WO 2008/145996); this thus amounts to 9.7 grams of R306 per ton of roots of *Neobeguea mahafalensis*, which is also markedly inferior to yield of the process of the present invention.

ii) The isolation of compound R310 in WO 2008/145996 from the dried roots of *Neobeguea mahafalensis*, which in its Example 41, page 145 was reported to give 24 mg of crude R310 from 722 grams of *Neobeguea mahafalensis* roots; thus 1 ton of roots would give 33 grams of crude R310 according to this process; the pure compound obtainable thus being substantially less than 33 grams per ton of *Neobeguea mahafalensis* roots (albeit the exact yield of pure compound not reported in WO 2008/145996), which is obviously markedly inferior to the process of the present invention.

iii) The isolation of a compounds termed "compound 6" described in a thesis by Nsima Tenabe Kipassa, from the Graduate School of Science and Engineering if Kagoshima University, Japan, March 2008, which is a member of structure (1) of this patent. (Structure of Kispassa "compound 6" drawn on page 45, FIG. 1 of the thesis). According to this report 1 kg of dried root bark of *Entandrophragma angolese* gave 3.2 mg of Kispassa "compound 6". Thus the previously known process of Kispassa yielded only 3.2 grams of the desired compound (1) of this invention per ton of the root bark of *Entandrophragma angolese*, which is a by far inferior process compared to the process of the present invention.

iv) The isolation of chukuvelutides A-F from dried stem bark of *Chukrasia tabularis* ver. *velutina* (Luo et al. 2009), all complying with structures (1) of the present invention. From 10 kg of stem bark chukuvelutides A-F were isolated with yields 15, 20, 5, 6, 5 and 6 mg, respectively. Thus the process of manufacturing the compound (1) of the invention by the process of Luo et al. (2009), yielding only from between 0.6 to 2 g per ton of *Chukrasia tabularis* stem bark, is a by far inferior compared with the present invention.

v) The isolation of chukuvelutide G (H) from of *Chukrasia tabularis* ver. *velutina* (Luo et al. 2012), complying with structures (1) and (5) of the present invention. From 10 kg of dried stem bark chukuvelutide G (H) was isolated with a yield of 20 mg. Thus the process of manufacturing the compound (1) of the invention by the process of Luo et al. (2012) yielded only 2 g per ton of *Chukrasia tabularis* stem bark, which is by far inferior compared with the present invention.

vi) The isolation of chubularisins L, M and N from the stem bark of *Chukrasia tabularis* (Liu et al., 2012). From 9 kg of dried stem bark respectively, 12, 9 and 3 mg of chubularisins L, M and N were isolated. Thus the process of manufacturing the compound (1) of the invention by the process of Luo et al. (2012) yielded only 0.3 to 1.3 g per ton of *Chukrasia tabularis* stem bark, which is by far inferior to the present invention.

vii) The isolation of tabulalin C from the dried stem bark of *Chukrasia tabularis* by Luo et al. (2011). From 10 kg 22 mg of tabulalin C was isolated. Thus the process of manufacturing the compound (1) of the invention by the process of Luo et al. (2011) yielded only 2.2 g per ton of *Chukrasia tabularis* stem bark, which is by far inferior to the present invention.

In the process of the present invention to afford the compound (1), (5) or (5a) of the invention, it is most preferred to afford compound (1) of the invention, even more preferred is the compound (1) of the invention where R12 is oxo, even more preferred is the compound (1) of the invention where R5 is hydrogen, and most preferred is the compound (1) of the invention where R12 is oxo and R5 is hydrogen. This is because the more preferred structures of structure (1) show more potent sexual enhancing activity compared with the less preferred. E.g. R306, SAE5 and SAE6 are more efficient sexual enhancing compounds compared with GL-1203 and R310 (see Example 5 and WO 2008/145996); the most desired compounds to afford by the process of the invention are compound 20 (SAE5), compound 16 (SAE6), compound 21 (R306), R306AB, R306BA, R306C, R306D, R306E, R306F, with SAE5 being most preferred.

It may be noted that in the above listed previously known processes i) to vii), only process i) yielded the most desired type of structure (1) of the invention, wherein substituent R12 is oxo and R5 hydrogen (i.e. R306 is preferred over R310 as R306 is more potent than R310 to induce a sexual enhancing effect; see WO 2008/145996); however process i) yielded only up to 17 g per ton of starting plant material which is by far inferior to the present process yielding between 191 to 639 g per ton starting dried plant material. In particular the process of the invention is highly efficient in affording the most desired compounds SAE5 (613 g per ton starting dried plant materials) and R306 (639 g/ton starting dried plant materials). SAE5 and R306 accordingly being among the most desired compounds of the invention.

The process of the invention to afford the compound (1), (5) or (5a) of the invention from a limonoid of structure (2a) or (2b), most preferably from a structure (2a), has the advantage that compounds with structure (2a) or (2b), in particular structures (2a), are richly available from many natural sources, and are even commercially available. Phragmalin is a type (2a) compound which can be obtained from *Chukrasia tabularis* seeds as demonstrated in Example 6 (as well as from stem bark and other parts of *Chukrasia tabularis*; see also Connolly et al. Perkin Transactions 1. 1978, (Issue 3) 285-288), as well as from *Entandrophragma caudatum* stem bark and leaves (R. R. Arndt and W. H. Baarshers, *Tetrahedron*, 1972, 28, 2333-2340). Other examples are the busseins, also being type (2a) compounds, which can be isolated in gram amounts per kg from *Entandrophragma bussei* trunk wood (Guex and Tamm, 1984, 1985); busseins even being commercially available from Gaia Chemical Corporation, 10 George Washington Plaza, Gaylordsville, Conn. 06755, USA). Many other species of the Meliaceae family are rich sources of phragmalin limonoids of the structure (2a) [and to a substantial less extent (2b)], as well, and can be used as starting materials for the process of the invention. For the sake of the present invention any part of a plant, preferably a Meliaceae, can be used in preparation of the compounds (2a), (2aa) or (2b), with (2aa) preferred, for use by the process of the invention. This includes stem bark, roots, root bark, trunk wood, branches, leaves, seeds and fruits, with seeds being most preferred.

The most preferred compound (2aa) for use in the process of the invention is phragmalin. This is because it can be used to prepare the most desired compounds SAE5, SAE6, R306, R306AB, R306BA, R306C, R306D, R306E, R306F of the invention and because phragmalin is readily obtainable in large quantities form plants grown for commercial/agricultural purposes, with the most important source being *Chukrasia tabularis* (also called *Chukrasia velutina*, *Chikrassia tabularis*, bastard cedar, Chittagong wood, Indian mahogany, Burmese almondwood, Lao mahagony, yonhim, yinma, chickrassy and Jamaica cedar). *Chukrasia tabularis* is a tree that is grown on plantations (or planted) in Bangladesh, Cambodia, China, India, Indonesia, Laos, Malaysia, Myanmar, Sri Lanka, Thailand, Vietnam, Cameroon, Costa Rica, Nigeria, Puerto Rico, South Africa, US, e.g. for its timber, for decorations and as wind shields at the side of other plantations, e.g. coffee plantations, as well as it's wide-spread in Asia in the wild.

Because of the fact that the process of the present invention is substantially more efficient than previously known processes, as well as that it can afford never before synthesized compounds in high yield, the present invention claims the compound (5) of the invention, more preferably the compound (1) of the invention, even more preferably the compound (1) of the invention where R12 is oxo, even more preferably the compound (1) of the invention where R5 is hydrogen, and even more preferably is the compound (1) of the invention where R12 is oxo and R5 is hydrogen, even more preferably anyone of compounds SAE5, SAE6, R306, R306AB, R306BA, R306C, R306D, R306E, R306F and most preferably the compound SAE5; (said compound preferably being a sexually enhancing compound), which is directly obtained by the process of the invention, preferably the process of the invention that proceeds first with the process according to schema (I) or (Ia) (followed by optional intermediate steps) followed then with the process according to schema (III), (IIIa) or (IIIb); in particular the present patent claims said compound which is a sexually enhancing compound.

However, in another closely related aspect of the invention, due to the fact that the process of the present invention is substantially more efficient than previously known processes, as well as that it can afford never before synthesized compounds in high yield, the present invention claims the compound (5) of the invention, more preferably more preferably the compound (1) of the invention, even more preferably the compound (1) of the invention where R12 is hydroxy, acyloxy, or acetyloxy, even more preferably the compound (1) of the invention where R5 is isobutyryl or 1-hydroxy-2-methylpropylidene and most preferably the compound (1) where R12 is hydroxy, acyloxy, or acetyloxy and R5 is isobutyryl or 1-hydroxy-2-methylpropylidene, even more preferably anyone of compounds GL-1203, R310, R310A, R310A3, R310A4, R310A5, R310B, R310B1, R310B2, R310B3, R310B4, R310B5, R310B6, R310B7, R310B8, R310B9, R310B10, R310B11, R310B12, R310B13, R310B14, R310B15, R310B16, R310B17, R310B18; (said compound preferably being a sexually enhancing compound), which is directly obtained by the process of the invention, preferably the process of the invention that first proceeds with the process according to schema (I) or (Ia) (followed by optional intermediate steps) prior to the process according to schema (III), (IIIa) or (IIIb); in particular the present patent claims said compound which is a sexually enhancing compound.

The present patent prefers any compound of structure (5), which is produced with the process of the invention with a yield of more than 50 g/ton, even more preferably more than 100 g/ton, more preferably more than 150 g/ton, even more preferably more than 180 g/ton of starting dried plant material.

This patent affords novel compounds (albeit known in principle from WO 2008/145996) with sexually enhancing activity which were never earlier manufactured, as well as it provides a process for which these compounds can readily be manufactured in large quantities from commercially available raw materials, simply by scaling up the process described herein (e.g. scaling up anyone of the procedures described in Examples 1 to 3 and 6 to afford a sexually enhancing compound as demonstrated in Example 5). This thus shows the industrial utility of the present patent as well as that it is inventive.

Yield of Compound (3)

Based on the yields given in Examples 1 to 3 and Example 6 the overall yields of compounds from Examples 1 to 3 complying with structure (3) from 1 ton (1000 kg) of dried *Chukrasia tabularis* seeds can be calculated as follows:

| Compound | Overall yield from 1 ton of seeds |
|---|---|
| 7 | 1756 g |
| 8 | 1649 g |
| 14 | 935 g |
| 15 | 503 g |
| 18 | 1576 g |
| 19 | 1414 g |

(These calculations take into account the purity of phragmalin used as well as molecular weights of compounds). Due to the high yield of the process of the invention the present patent claims the compound (3) of the invention which is produced with the process of the invention with a yield of more than 50 g/ton, even more preferably more than 100 g/ton, even more preferably more than 150 g/ton, even more preferably more than 180 g/ton, even more preferably more than 250 g/ton, even more preferably more than 390 g/ton, and most preferably more than 450 g/ton of starting dried plant material.

Dryness of Plant Materials

For the sake of the present patent a plant material is regarded to be dry when its content of water is less than 10%. The dryness of a plant material can be estimated by a process well known in the art where the plant material is weighed and then subjected to excessive drying at a temperature of between 40-60° C. in a well ventilated environment for as long time as the weight of the plant material does not appreciably reduce anymore over time (e.g. between 6 to 72 h; e.g. preferably to a time point where the reduction of weight being less than 0.2% per hour). The water content of the original materials can then be calculated as:

$$\text{Percent\_water\_content} = \frac{100 \times (\text{weight\_before\_drying} - \text{weight\_after\_drying})}{\text{weight\_before\_drying}}$$

For the plant material to be regarded as dry the Percent_water_content should be 10% or less.

COMPOUND OF THE INVENTION

The compound of the invention comprises compound (3) [and its variations (3a), (4), (4aa), (4bb), (4cc), (4dd), (4ee), (4ff), (4gg) and (4hh) described herein] when it has been produced directly by the process of the invention as well as when it has been produced by other means, the compound (2b) [and its variation (2bb) described herein] when it has been produced directly by the process of the invention, and compound (5) [and its variations described herein (5a) and (1) and the compound of claim 40 of WO 2008/145996) when it has been directly produced by the process of the invention].

The compound of the invention also includes the compound that upon systemic administration to an animal or human by virtue of the metabolism of said animal or human is converted to the compound of the invention defined in the previous paragraph. Such a compound is in this patent defined as a pro-drug to the compound of the invention. Pro-drugs are well known in the art. For example, by adding a chemical group to the compound of the invention that is easily removed by the metabolism of an organism, a medicinal chemist can create a pro-drug of the compound of the invention.

The compound of the invention may be obtained in radioactive form, e.g. by semi-synthesis, by exchanging suited group(s) or atom(s) in the compound of the invention with radioactive atom(s), or with group(s) where one or several atom(s) are radioactive. Preferred radioactive atoms for the purpose of this embodiment of the invention are $^3$H, $^{14}$C, $^{11}$C, $^{18}$O, $^{125}$I and $^{131}$I. Manufacturing of radioactive compounds comprises procedures well known in the art and can be applied to afford a radioactive compound of the invention.

Comprised by the invention is the salt of the compound of the invention; in particular the pharmaceutically acceptable salt(s); i.e. those salts of compounds of the invention that are safe and effective for systemic use in mammals and is particularly desired for those compound of the invention that are capable of forming salts.

Comprised by the invention are also the structures of the tautomeric forms wherein one of the structures of the tautomers is comprised by the structure of the invention.

Pharmaceutical Compositions

The compound of the invention [which includes compound (3) (and its variations described herein), the compound (2b) (and its variations described herein) when it has been produced directly by the process of the invention, and compound (5) (and its variations described herein) when it has been directly produced by the process of the invention] is preferably administered in a composition including a pharmaceutically acceptable carrier or excipient. The term "pharmaceutically acceptable" means a carrier or excipient that does not cause any untoward effects in patients to whom it is administered. Such pharmaceutically acceptable carriers and excipients are well known in the art (see e.g. Remington's Pharmaceutical Sciences, 1990, Rowe et al, 2005, and references therein). The exact dose to be administered depends on the circumstances. Normally, the dose should be capable of preventing or lessening the severity or spread of the condition or indication being treated. It will be apparent to those of skill in the art that an effective amount of the compound of the invention depends, inter alia, upon the condition, disease or purpose of treatment, the dose, the administration schedule, whether the compound of the invention is administered alone or in conjunction with other therapeutic agents, the general health of the patient, age, and the like. Generally, and in particular if administered via the oral route, the compound of the invention should be administered in a dose of 0.001 to 100 mg body weight per kilo throughout the treatment period.

The pharmaceutical composition may be formulated in a variety of forms, including liquid, gel, lyophilized, powder, compressed solid, or any other suitable form. The preferred form will depend upon the particular indication being treated and will be apparent to one of skill in the art.

The pharmaceutical composition may be administered orally, subcutaneously, intravenously, intracerebrally, intranasally, transdermally, intraperitoneally, intramuscularly, intrapulmonary, vaginally, rectally, intraocularly, or in any other acceptable manner, e.g. using PowderJect or ProLease technology. The composition can be administered continuously by infusion, although bolus injection is acceptable, using techniques well known in the art, such as pumps or implantation. In some instances the composition may be directly applied as a solution or spray. The preferred mode of administration will depend upon the particular indication being treated and will be apparent to one of skill in the art. However, the currently preferred mode of administration is via the oral route.

The pharmaceutical composition of the invention may be administered in conjunction with other therapeutic agents. These agents may be incorporated as part of the same pharmaceutical composition or may be administered separately from the composition of the invention, either concurrently or in accordance with any other acceptable treatment schedule.

Pharmaceutical Preparation for Oral Administration

For oral administration, the pharmaceutical composition may be in solid or liquid form, e.g. in the form of a capsule, tablet, suspension, emulsion or solution. The pharmaceutical composition is preferably made in the form of a dosage unit containing a given amount of the active ingredient. A suitable daily dose for a human or other mammal may vary widely depending on the condition of the patient and other factors, but can be determined by persons skilled in the art using routine methods.

Solid dosage forms for oral administration may include capsules, tablets, suppositories, powders and granules. In such solid dosage forms, the active compound may be admixed with at least one inert diluent such as sucrose, lactose, or starch. Such dosage forms may also comprise, as is normal practice, additional substances, e.g. lubricating agents such as magnesium stearate. In the case of capsules, tablets and pills, the dosage forms may also comprise buffering agents. Tablets and pills can additionally be prepared with enteric coatings.

The compound of the invention may be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compound of the invention may be dissolved in saline, water, polyethylene glycol, propylene glycol, ethanol, oils (such as corn oil, peanut oil, cottonseed oil or sesame oil), tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art In one embodiment of this aspect of the invention the pharmaceutical is manufactured by dissolving the compound of the invention in pharmaceutically acceptable oil (e.g. hydrogenated caster oil, olive oil, sun flower oil, cotton oil, peanut oil, Neobee M5; tri caprylic/capric triglyceride ester, Miglyol, propyleneglycol dicaprylate, Sefsol, ethoxylated plant fats, soybean oil, or any other suited oil or corresponding carrier) with other optional hydrophobic carrier, detergent or surfactant (e.g. triacetin, benzyl benzoate, ethyl oleate, ethanol, acylated monoglycerides, propyl dicaprylates/dicaprates, caprylic/capric acid triglycerides, polyethylene glycol (PEG); e.g PEG 500, PEG1500 or any other molecular size PEG, polyvinyl pyrrolidone (PVP), Tween; e.g. Tween-20, polyoxyethylenesorbitan monolaurate, or a combination thereof), and with optional addition of, or a combination thereof. A fat, which is solid at room temperature, may also be, such as cocoa butter. The fat is heated which allows the compound of the invention to be solubilized in the fat. After cooling to solidify the fat the preparation can be granulated and use in tablets, or it can be molded into tablets, or capsules can be filled with it. Any other solid fat, or pharmaceutically acceptable substitute thereof, capable of solubilizing the fat-soluble compound of the invention can be used, including with the addition of with any optional hydrophobic carrier.

The pharmaceutical compositions may be subjected to conventional pharmaceutical operations such as sterilization and/or may contain conventional adjuvants such as preservatives, stabilizers, wetting agents, emulsifiers, buffers, fillers, etc.

Liquid dosage forms for oral administration may include pharmaceutically acceptable emulsions, solutions, suspensions and syrups and elixirs containing inert diluents commonly used in the art, such as water. Such compositions may also comprise adjuvants, such as wetting agents, sweeteners, flavoring agents and perfuming agents.

An example of a pharmaceutical composition for a compound of the invention (SAE5) for oral use is given in Example 9.

Pharmaceutical Preparation for Parenteral Administration

The compound of the invention may be dissolved in pharmaceutically acceptable oil (e.g. hydrogenated caster oil, olive oil, peanut oil or any other oil) with an optional hydrophobic carrier (e.g. triacetin, benzyl benzoate or ethyl oleate or a combination thereof), and with optional addition of acylated monoglycerides, propyl dicaprylates/dicaprates, caprylic/capric acid triglycerides, or a combination thereof for use as an injectable.

The compound of the invention can be administered intravenously in a pharmaceutical preparation comprised by an emulsion. For example prepared so as to form lipid particles in water with the compound of the invention included (i.e. an emulsion), e.g. by using (but not limited to) mixtures with one or several of oil, vegetable oil, phospholipids, surfactant, sodium deoxycholate, cholesterol, ethyl oleate, Miglycol, lecithin, water and applying procedures well-known in the art (Remington's Pharmaceutical Sciences, 1990, Rowe et al, 2005, Yua et al, 1993, and references therein).

General Re. Pharmaceutical Preparations for the Compound of the Invention

Any other suitable pharmaceutically acceptable formulation can be used for preparing an injectable for the compound of the invention, as is well known in the art (Remington's Pharmaceutical Sciences, 1990, Rowe et al, 2005, and references therein).

Moreover, the pharmaceutical preparations (compositions) of WO 2008/145996 apply for the sake of the present patent, merely by exchanging the compound or extract of WO 2008/145996 with the compound of this invention.

The invention also includes processes for the manufacture of pharmaceutical preparations comprising one or more of the compounds of the invention, as well as to their uses for various medical and veterinary practices.

An example of a pharmaceutical composition for a compound of the invention (LG-1725) for injection is given in Example 9.

Use of the Compound of the Invention for Treatment of Medical or Veterinary Conditions or for Scientific Experimentation As is evident from WO 2008/145996 as well as from Example 5, compound (5) and all its variations described herein and those of claim 40 in WO 2008/145996 is useful for eliciting a sexual enhancing effect and for the treatment of sexual dysfunctions, including (but not limited to) including hypoactive sexual desire disorders in men and woman and erectile dysfunctions and ejaculatory dysfunctions in men.

As is evident from WO 2008/145996 treatment schedules are important aspects to achieve an optimal treatment effect, which relates to the long-lasting effect of the compound of the invention and the lag-time before its effect appears (this long-lasting effect is also evident from Example 5). A suited treatment schedule has to take into account this long lasting effect, which means that the compound of the invention is administered for an initial period lasting from one to seven days where after the administration is discontinued while the treatment effect may be seen for long time thereafter, even weeks or months in some cases.

As is evident from Example 3 the compound (3) of the invention and all its variations described herein induces marked aggression. For situations when it is so desired the compound of the invention can be used to induce aggressive behavior, or increased level of aggression, by systemic administration to an animal or human, including for treatment of phsychiatric and neurologic conditions.

Moreover, compound (2b) and all its variations described herein have useful therapeutic properties and can be administered systemically to an animal or human for treatment purposes.

Further variations and embodiments of the invention are evident from Examples 1 to 9 and the amended claims herein, which should not be taken to limit the scope of the invention in any way.

REFERENCES

Arndt R. R., Barschers W. H. Structure of phragmalin. Meliacin with a norbornane part skeleton. *Tetrahedron*, 1972, 28(8), 2333-2340.

Blay G, Cardona L, Garcia B, Garcia C, Pedro J R: Anon-catalysed ring-opening aminolysis reaction of sesquiterpene lactones. Tetrahedron Letters 1994, 35, 931-4.

Bloomfield J J, Lee S L: Control of lithium aluminum hydride reduction of cyclic dicarboxylic acid anhydrides to produce γ-lactones or diols: Journal of Organic Chemistry 1967, 32, 3919-24.

Brown D. A., Taylor D. A. H. Carbon-13 nuclear magnetic resonance spectra of some limonoids. Part I V. Extractives from *Chukrasia tabularis* A. Juss. J. Chem. Res., Synopses, 1978, (1), 20

Chen, F F, Younglee, Renesteinauer, Y, Benoiton, L N: Mixed anhydrides in peptide synthesis. A study of urethane formation with a contribution on minimization of racemization, NC. an. J. Chem. 1987, 65, 613.

Coombes P. H., Mulholland D. A., Randrianarivelojosia M. Phragmalin Limonoids from the Madagascan Meliaceae *Neobeguea leandreana*. *J. Nat. Prod.*, 2003, 66(6), 735-738

Connolly J. D., MacLellan M., Okorie D. A., Taylor D. A. H. Limonoids from *Xylocarpus moluccensis* (Lam.) M. Roem. *J. Chem. Soc., Perkin Trans.* 1, 1976 (9), 1993-1996.

Connolly, J D, Labbé. C L, and Rycroft. D S: Tetranortriterpenoids and Related Substances. Part 20.1 New Tetranortriterpenoids from the Seeds of *Chukrasia fabularis* (Meliaceae); Simple Esters of Phragmalin and 12α-Acetoxyphragmalin. Journal of the Chemical Society, Perkin Transactions 1. 1978, (Issue 3) 285-288 Published on 1 Jan. 1978 on http://pubs.rsc.org doi:10.1039/P19780000285

Connolly J, Phillips W R, Mulholland Dam Taylor D A H: Spicatin, a protolimonoid from *Entandrophragma spicatum*. *Phytochemistry.* 1981, 20, 2596-7.

Cui J, Wu J, Deng Z, Proksch P, Lin W: Xylocarpins A-I, limonoids from the Chinese mangrove plant *Xylocarpus granatum*. *J Nat Prod*. 2007, 70, 772-8.

Cui J., Wu J., Deng Z., Proksch P., Lin W. Xylocarpins A-I, limonoids from the Chinese mangrove plant *Xylocarpus granatum*. *J. Nat. Prod.*, 2007, 70(5), 772-778).

Ekong D. E. U., Olagbemi E. O. Novel meliacins (limonoids) from the wood of *Pceucedrela kotschyii*. *Tetrahedron Lett.*, 1967, 8(36), 3525-3527.

R M, Ferrari P F, Parmigiani S, Miczek K A.: Escalated aggressive behavior: dopamine, serotonin and GABA. Eur J. Pharmacol. 2005 Dec. 5; 526(1-3):51-64. Review.

de Boer S F, Koolhaas J M.: 5-HT1A and 5-HT1B receptor agonists and aggression: a pharmacological challenge of the serotonin deficiency hypothesis. Eur J Pharmacol. 2005 Dec. 5; 526(1-3):125-39. Epub 2005 Nov. 28.

Ekong D. E. U., Olagbemi E. O. *Tetrahedron Lett.*, 1967, 8(36), 3525-3527.

Guex M., Tamm C. Die Busseine C, D, E, F, G, H, J, K, L und M, zehn neue Tetranortriterpene aus *Entandrophragma bussei* Harms. Helv. Chim. Acta, 1984, 67(3), 885-901

Guex, M and Tamm, C: Die busseine C, D, E, F, G, H, J, K, L und M, zehn neue tetratriterpene aus *Entandrophramga bussei* Harms, Helvetica chimica Acta vol. 67, Fasc. 3 1984, Nr. 99, p. 885-901.

Guex M, Tamm C: Selective reactions of the tetranortriterpenes busseins A and B. *Helvetica Chimica Acta* 1985, 68, 522-33.

Hay A E, Ioset J R, Ahua K M, Diallo D, Brun R, Hostettmann K: Limonoid orthoacetates and antiprotozoal compounds from the roots of *Pseudocedrela kotschyi*. *J Nat Prod*. 2007, 70, 9-13.

Lebold, T P, Gallego, G M, Marth, C J, Sarpong, R: Synthesis of the bridging framework of phragmaline-type limonoids. Organic Letters, 2012, 14(8), 2110-2113.

Lin B.-D., Zhang C.-R., Yang S.-P., Zhang S., Wu Y., Yue J.-M. D-Ring-opened phragmalin-type limonoid orthoesters from the twigs of *Swietenia macrophylla*. *J. Nat. Prod.*, 2009, 72(7), 1305-1313

Liu, W. Xu, D D, Repič, O and Blacklock T J: A mild method for ring-opening aminolysis of lactones. *Tetrahedron Letters*. Volume 42, Issue 13, 26 Mar. 2001, Pages 2439-2441

Liu H B, Zhang H, Li P, Wu Y, Gao Z B, Yue J M.: Kv1.2 potassium channel inhibitors from *Chukrasia tabularis*. *Org Biomol Chem*. 2012 Feb. 21; 10(7):1448-58. Epub 2012 Jan. 4.

Luo J, Wang J-S, Wang X-B, Huang Z-F, Luo J-G, Kong L-Y: Chukvelutilides A-F, phragmalin limonoids from the stem barks of *Chukrasia tabularis* var. *velutina*. *Tetrahedron*. 2009, 65, 3425-31.

Luo J, Li Y, Wang J S, Kong L Y. D-ring-opened phragmalin-type limonoids from *Chukrasia tabularis* var. *velutina*. Chem Biodivers. 2011 December; 8(12):2261-9. doi: 10.1002/cbdv.201000285.

Luo J, Li Y, Wang J S, Kong L Y.: Two new C-15 enolic acyl phragmalin-type limonoids from *Chukrasia tabularis* var. *velutina*. Nat Prod Res. 2012 Apr. 27. [Epub ahead of print] PMID: 22537580

Miczek K A, Weerts E, Haney M, Tidey J.: Neurobiological mechanisms controlling aggression: preclinical developments for pharmacotherapeutic interventions. Neurosci Biobehav Rev. 1994 Spring; 18(1):97-110.

Mulholland D. A., Taylor D. A. H. *Phytochemistry*, 1988, 27(6), 1741-1743.

Mulholland D A, Parel B, Coombes P H: The chemistry of the Meliaceae and Ptaeroxylaceae of Southern and Eastern Africa and Madagascar. *Current Organic Chemistry*, 2000, 4, 1001-54.

Nakatani M, Abdelgaleil S A, Saad M M, Huang R C, Doe M, Iwagawa T: Phragmalin limonoids from *Chukrasia tabularis*. *Phytochemistry*. 2004, 65, 2833-41.

Narender T., Khaliq T., Shweta. $^{13}$C NMR spectroscopy of D and B, D-ring seco-limonoids of Meliaceae family. *Natural Product Research*, 2008, 22(9), 763-800.

Niven M L, Taylor D A H: Revision of the structure of the limonoid Pseudrelone B from *Pseudocedrela kotschyii*. *Phytochemistry*. 1988, 27, 1542.

Olivier B, van Oorschot R.: 5-HT1B receptors and aggression: a review. Eur J Pharmacol. 2005 Dec. 5; 526(1-3): 207-17. Epub 2005 Nov. 28. Review.

Pettit G R, Green B, Kasturi T R, Ghatak U R: Steroids and related natural products. X. Reduction of lactones. Tetrahedron. 1962, 18, 953-8.

Randrianarivelojosia M, Maria P. Kotsosb M P, Mulholland D A: A limonoid from *Neobeguea mahafalensis*. *Phytochemistry*. 1999, 52, 1141-43.

Ragettli V. T., Tamm C. Die Chukrasine A, B, C, D und E, fünf neue Tetranortriterpene aus *Chukrasia tabularis* A. JUSS. *Helv. Chim. Acta*, 1978, 174(5), 1814-1831

Remington's Pharmaceutical Sciences, 18th edition, A. R. Gennaro, Ed., Mack Publishing Company [1990]; ISBN-13: 978-0912734040.

Rowe, R C, Sheskey, P J, Owen, S C: Handbook of Pharmaceutical Excipients, 3rd edition, A. Kibbe, Ed., A PhA Publications, 5th edition (Dec. 14, 2005), ISBN-13: 978-1582120584

Saad M M G, Iwagawaa T, Doe M, Nakatani M: A Swietenialides, novel ring D opened phragmalin limonoid orthoesters from *Swietenia mahogani* JACQ. *Tetrahedron* 2003, 59, 8027-33.

Sarigaputi C., Teerawatananond T., Pengpreecha S., Muangsin N., Pudhom K. Xyloccensin E. *Acta Crystallographica*, Section E: Structure Reports Online, 2010, E66 (6), o1348-o1349

Smith, M B and Smith, M: Organic Synthesis, $2^{nd}$ edition, Mcgraw Hill, 2001, ISBN-13: 978-0070482425

Taylor D. A. H. Functional groups of bussein. *Chemistry & Industry* (London, United Kingdom), 1967, (14), 582

Taylor D A H: $^{13}$C nuclear magnetic resonance spectra of some limonoids. Part I. The structure of procerin, an extractive from *Carapa procera*. *J. Chem. Soc., Perkin Trans.* 1, 1974, 437-441

Warren, S and Wyatt, P: Organic Synthesis—Strategy and Control, Wiley-Blackwell, 2007, ISBN: 978-0471489405.

Warren, S and Wyatt, P: Organic Synthesis: The Disconnection Approach, $2^{nd}$ edition. Wiley, 2009, ISBN-13: 978-0470712375.

Yua, W. et al. A novel approach to the preparation of injectable emulsions by a spontaneous emulsification process. International Journal of Pharmaceutics-Volume 89, Issue 2, 15 Jan. 1993, Pages 139-146.

Yi L, Bandu M L, Desaire H: Identifying lactone hydrolysis in pharmaceuticals. A tool for metabolite structural characterization. Anal. Chem. 2005), 77, 6655-63.

EXAMPLES

Example 1

Synthesis of Compounds of Structure (5) Starting from Phragmalin

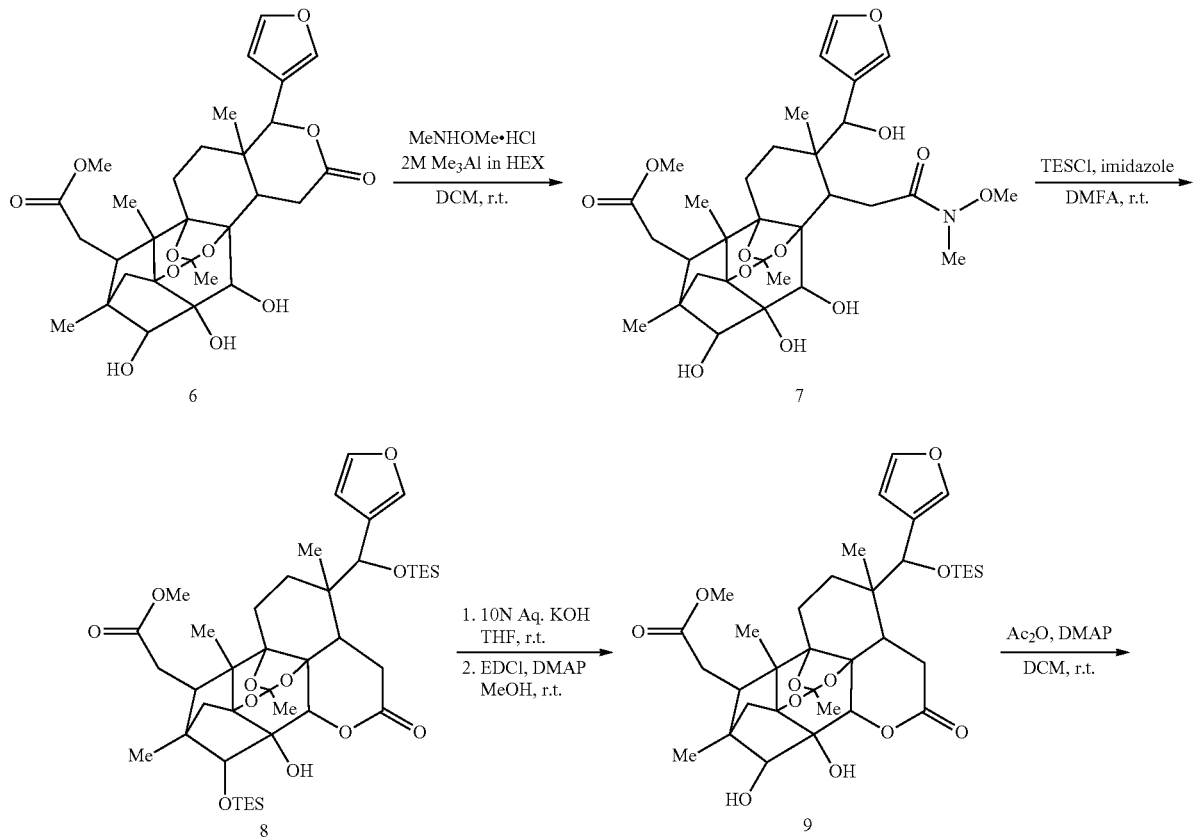

Scheme 1

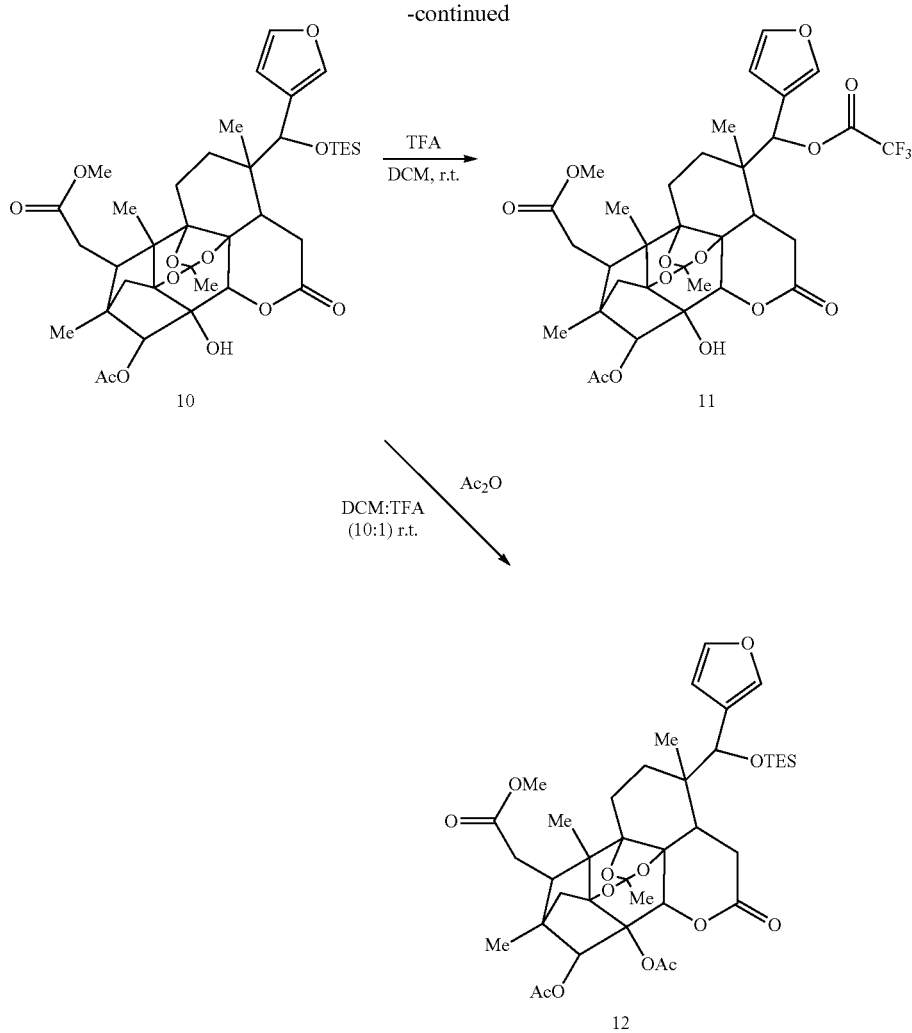

A summary of the steps is shown in Scheme 1

Compound 7

A suspension of MeNHOMe.HCl (O-dimethylhydroxylamine hydrochloride; N,O-dimethylhydroxylamine) (351 mg, 3.6 mmol) in DCM (dichloromethane) (20 mL) was cooled in an ice bath and to this 2 M Me$_3$Al in HEX (trimethylaluminium in hexane) (3.5 mL, 7.2 mmol) was added dropwise. After addition was complete, the cooling bath was removed and the reaction mixture was stirred for 15 min. The mixture was cooled again in an ice bath and to this a solution of compound 6 (phragmalin) (200 mg, 0.36 mmol) in DCM was added. The cooling bath was removed and the reaction mixture was stirred at room temperature (r.t.) for 30 min, and then cooled again in an ice bath. An aqueous solution of Rochelle's salt (potassium sodium tartrate, NaKC$_4$H$_4$O$_6$; here also termed "segnet") (30 mL) was added and the organic phase was separated. The aqueous phase was washed with DCM (5×20 mL) and the combined organic phase dried over sodium sulfate (Na$_2$SO$_4$) The solution was evaporated in vacuo and the residue was purified by flash chromatography on silica gel, eluting with EtOAc (ethyl acetate) to give compound 7 [i.e. a specific example of structure (3)] [yield of 7 from 6 was 45% (100 mg)] as colorless oil.

HRMS (M+H)$^+$: 622.2871, C$_{31}$H$_{44}$NO$_{12}$ requires 622.2863.

$^1$H-NMR (CDCl$_3$, TMS): δ 0.99 (3H, s); 1.10 and 1.11 (total 6H, both s); 1.35 (1H, br t, 14.5 Hz); 1.55 (3H, 5); 1.55 (1H, d, 10.5 Hz); 1.68 (1H, dd, 2.7 and 14.5 Hz); 2.22 (1H dd, 3.9 and 16.0); 2.32 (2H, br t, 6.7 Hz); 2.39 (1H, dd, 9.4 and 16.0 Hz); 2.45 (2H, m); 2.90-2.98 (3H, m); 3.08-3.20 (3H, br s); 3.17 (3H, s); 3.40-3.55 (1H, m); 3.56 (3H, s); 3.72 (3H, s); 4.21 (1H, d, 8.6 Hz); 4.72 (1H, d, 9.4 Hz); 5.23 (1H, s); 6.49 (1H, d, 1.5 Hz); 7.33 (1H, t, 1.5 Hz) and 7.48 (1H, s).

$^{13}$C-NMR (150 MHz, CDCl$_3$, TMS): δ 10.7; 14.7; 15.8; 20.1; 21.1; 23.8; 25.4; 29.4; 31.9; 32.2; 34.3; 35.8; 39.6; 40.0; 45.6; 45.8; 46.7; 51.9; 60.4; 69.5; 69.7; 78.9; 83.5; 110.2; 118.6; 126.9; 140.5; 142.4; 173.2; 174.7; 176.7.

Demonstration of the Requirements for Very Distinct Conditions for Formation of Weinreb Amide 7 from 6 (Phragmalin)

To afford 7 from 6 very distinct conditions were required; this amounted to applying the correct molar ratios of MeNHOMe.HCl, Me$_3$Al and phragmalin, as well as selection of narrow range of timing and the appropriate temperature, as is evident from the 12 experiments (denoted #1-12) in the below table:

| # | Conditions | Result |
|---|---|---|
| 1 | 20 mg scale of 6, MeNHOMe•HCl (4 eq), 1,8-diazabicyclo[5.4.0]undec-7-ene (DBU) (5 eq), DCM, r.t., 16 h, then heating at 60° C. for 5 h | Recovered 6; 7 was not formed. |
| 2 | 20 mg scale of 6, MeNHOMe•HCl (6 eq), 3M Me$_3$Al in toluene (5 eq), DCM, 0° C. to r.t., 30 min | Recovered 6; 7 was not formed. |
| 3 | 20 mg scale of 6, MeNHOMe•HCl (12 eq), 3M Me$_3$Al in toluene (12 eq), DCM, 0° C. to r.t., 16 h | 6:7 = 3:1 (molar proportion estimated by $^1$H-NMR of the crude reaction mixture); 7 isolated by preparative TLC, yield of 7 ca 20%. |
| 4 | 20 mg scale of 6, MeNHOMe•HCl (20 eq), 3M Me$_3$Al in toluene (20 eq), DCM, 0° C. to r.t., 2 days | 6:7 = 14:1 (molar proportion estimated by $^1$H-NMR of the crude reaction mixture) |
| 5 | 20 mg scale of 6, MeNHOMe•HCl (12 eq), 3M Me$_3$Al in toluene (15 eq), DCM, 0° C. to r.t., 2 days | 6:7 = 2.5:1 (molar proportion estimated by $^1$H-NMR of the crude reaction mixture). |
| 6 | 20 mg scale of 6, MeNHOMe•HCl (10 eq), 3M Me$_3$Al* in toluene (20 eq), DCM, 0° C., 1 h *Fresh batch of Me$_3$Al | 6:7 = 1:10 (molar proportion estimated by $^1$H-NMR of the crude reaction mixture, no other significant by-products identified). |
| 7 | 100 mg scale of 6, MeNHOMe•HCl (10 eq), 3M Me$_3$Al in toluene (20 eq), DCM, 0° C.-r.t., 60 min, quenching with aqueus segnet, extraction with EtOAc | Mixture of products, as revealed by $^1$H-NMR of the crude reaction mixture. |
| 8 | 20 mg scale of 6, MeNHOMe•HCl (10 eq), 3M Me$_3$Al in toluene (10 eq), DCM, r.t., 40 min, quenching with aqueous segnet, extraction with EtOAc | Mixture of products, as revealed by $^1$H-NMR of the crude reaction mixture. |
| 9 | 20 mg scale of 6, MeNHOMe•HCl (10 eq), 3M Me$_3$Al in toluene (5 eq), DCM, r.t. 60 min, quenching with aqueous segnet, extraction with EtOAc | Mixture of products, as revealed by $^1$H-NMR of the crude reaction mixture. |
| 10 | 20 mg scale of 6, MeNHOMe•HCl (10 eq), 3M Me$_3$Al in toluene (20 eq), DCM, r.t., 30 min, quenching with aqueous segnet, extraction with DCM | 6:7 = 1:1 (molar proportion estimated by $^1$H-NMR of the crude reaction mixture), 7 isolated by preparative TLC, yield of 7ca 40%. |
| 11 | 100 mg scale of 6, MeNHOMe•HCl (10 eq), 3M Me$_3$Al in toluene (20 eq), DCM, r.t., 30 min, quenching with aqueous segnet, extraction with DCM | 7 isolated by flash chromatography, yield of 7 51%. |
| 12 | 200 mg scale of 6, MeNHOMe•HCl (10 eq), 3M Me$_3$Al in toluene (20 eq), DCM, r.t., 30 min, quenching with aqueous segnet, extraction with DCM | 7 isolated by flash chromatography, yield of 7 45% (34% of 6 was also recovered). |

Note that for experiment #12 in the above table 34% of the starting material, substance 6 (phragmalin), was recovered, which can be entered once again in the process, thus effectively increasing the total yield for 7 beyond the above mentioned yield of 45% for the process, when it is iteratively repeated.

Note that the reaction does not proceed with DBU as catalyst; it only proceeds when Me$_3$Al is used as catalyst. Moreover, the ratio of MeNHOMe.HCl to Me$_3$Al is critical (the best is a molar ratio of 1:2) as well as temperature and time is critical; the best is room temperature and a short reaction times (30 min to 1 h); other molar ratios or temperature proceeds with formation of side products, or does not allow the reaction to proceed at all.

Compound 8

To a solution of compound 7 (97 mg, 0.16 mmol) and imidazole (163 mg, 2.4 mmol) in DMF (dimethylformamide) (3 mL) TESCl (triethylsilyl chloride) (268 µl, 1.6 mmol) was added and the mixture was stirred overnight. To this reaction mixture water (20 mL) was added and the product was taken up into EtOAc (30 mL). The aqueous phase was separated and the organic phase was washed with water (3×15 mL) and dried over Na$_2$SO$_4$. The solution was evaporated in vacuo and the residue was purified by flash chromatography on silica gel, eluting with a mixture of light petroleum ether and EtOAc (2:1) to give compound 8 (91 mg, 70%) as colorless oil.

HRMS (M+H)$^+$: 834.4638, C$_{43}$H$_{72}$NO$_{11}$Si$_2$ requires 834.4644.

$^1$H-NMR (CDCl$_3$, TMS): δ 0.46-0.53 (6H, m); 0.69-0.80 (6H, m); 0.89 (9H, t, 8.0 Hz); 0.92 (3H, s); 1.03 (9H, t, 7.8 Hz); 1.05 (3H, s); 1.10-1.30 (1H, m); 1.17 (3H, s); 1.49 (3H, s); 1.54-1.64 (3H, m); 1.74-1.79 (2H, m); 2.17 (1H, dd, 3.9 and 14.9 Hz); 2.29-2.38 (1H, m); 2.43 (1H, m); 2.68 (1H, d, 14.9 Hz); 2.75 (1H, s); 2.86 (1H, dd, 3.9 and 9.4 Hz); 3.15 (3H, s); 3.28 (1H, d, 9.8 Hz); 3.46 (1H, s); 3.53 (3H, s); 3.72 (3H, s); 3.80 (1H, br t, 13 Hz); 4.50 (1H, s); 5.19 (1H, s); 6.45 (1H, s); 7.33 (1H, s) and 7.39 (1H, s).

Note that the protection of the hydroxy groups at carbon 17 and carbon 3 provided by this example in conversion of 7 to 8 over any of the hydroxy groups at carbon 2 and 30 [atom numbering as in structure (2a) given above] is an important feature of this invention, as this allowed in the following step (i.e. the conversion of 8 to 9) to implement the hydrolysis of the Weinreb amide to form a free carboxylic acid and formation of a new lactone ring with the hydroxy group at position 30 using EDCI [1-ethyl-3(3-dimethylaminopropyl)carbodiimide]; without this regioselective protection of the hydroxy group at position 17 reformation of the lactone ring in the starting position would have occurred.

Compound 9 (AJ-2105)

To a solution of compound 8 (40 mg, 0.048 mmol) in THF (tetrahydrofuran) (4 mL) 10 M aqueous potassium hydroxide (KOH) (24.5 µl, 0.24 mmol) was added. The mixture was stirred at r.t. for 24 h and to this aqueous 5% potassium bisulfate (KHSO$_4$) (10 mL) was then added. The mixture was extracted with EtOAc (3×10 mL), the combined organic phase dried over Na$_2$SO$_4$, filtered and evaporated. The residue was dissolved in MeOH (methanol) (2 mL) and HOBt (1-hydroxybenzotriazole) (21 mg, 0.16 mmol) was added to the solution followed by DMAP (4-dimethylaminopyridine) (20 mg, 0.16 mmol) and EDCI [1-ethyl-3(3-dimethylaminopropyl)carbodiimide] (31 mg, 0.16 mmol). The reaction mixture was stirred for 6 h at r.t. and to this aqueous 5% KHSO$_4$ (10 mL) was added. The mixture was extracted with EtOAc (2×10 mL) and the combined organic phase was dried over Na$_2$SO$_4$. The solvent was evaporated and the residue was purified by radial chromatography on silica gel, eluting with a mixture of light petroleum ether and EtOAc (1:1) to give compound 9 (9.1 mg, 28%) as colorless oil.

Note1: The procedure was repeated four additional times starting with 34-44 mg of compound 8 in order to optimize it, varying the amount of 10 M aqueous KOH from 5 to 15 equivalents and without HOBt, with yields of compound 9 ranging 20 to 63%.

Note2: Surprisingly the process gives a regioselective deprotection of the hydroxy function at carbon 3, which allows getting the desired compound 10 in the next step by acetylation in this position.

HRMS (M+H)$^+$: 675.3211, C$_{35}$H$_{51}$O$_{11}$Si requires 675.3200.

$^1$H-NMR (600 MHz, CDCl$_3$, TMS): δ 0.46-0.53 (6H, m); 0.88 (9H, t, 7.8 Hz); 1.01 (3H, s); 1.10-1.30 (1H, m); 1.13 (3H, s); 1.20 (3H, s); 1.64 (3H, s); 1.65 (1H, d, 11.0 Hz); 1.75-1.95 (4H, m); 1.99 (1H, dd, 3.1 and 9.0 Hz); 2.28 (1H, dd, 3.1 and 16.4 Hz); 2.35-2.40 (1H, m); 2.45 (1H, dd, 9.8 and 16.0 Hz); 2.72 (1H, s); 2.73-2.78 (2H, m); 3.25 (1H, dd, 3.1 and 18.8 Hz); 3.65 (1H, s); 3.70 (3H, s); 4.96 (1H, s); 5.39 (1H, s); 6.44 (1H, s); 7.36 (1H, s) and 7.55 (1H, s).

$^{13}$C-NMR (150 MHz, CDCl$_3$, TMS): δ 4.8; 5.2; 5.3; 6.6; 6.8; 7.0; 14.8; 15.6; 21.0; 21.4; 23.9; 27.4; 29.5; 34.0; 36.0; 36.2; 39.5; 39.9; 45.4; 45.7; 51.8; 69.5; 74.6; 78.5; 81.0; 83.3; 84.6; 84.7; 110.6; 118.5; 124.7; 141.2; 142.5; 169.4; 173.1.

Compound 10 (AJ-2106)

To a solution of compound 9 (23 mg, 0.034 mmol) in DCM (2 mL) was added DMAP (17 mg, 0.016 mmol) followed by Ac$_2$O (acetic anhydride) (65 µL, 0.68 mmol). The reaction mixture was stirred at r.t. for 4 h and then 1 M aqueous sodium bicarbonate (NaHCO$_3$) (10 mL) was added. The mixture was extracted with EtOAc (3×10 mL), and the combined organic phases were dried over Na$_2$SO$_4$, filtered and evaporated. The residue was purified by radial chromatography on silica gel, eluting with a mixture of light petroleum ether and EtOAc (1:1) to give compound 10 (22.5 mg, 92%) as colorless oil.

HRMS (M+H)$^+$: 717.2998, C$_{37}$H$_{53}$O$_{12}$Si requires 717.3306.

$^1$H-NMR (600 MHz, CDCl$_3$, TMS): δ 0.45-0.61 (6H, m); 0.89 (9H, t, 8.0 Hz); 0.92 (3H, s); 1.10-1.30 (1H, m); 1.12 (3H, s); 1.21 (3H, s); 1.64 (3H, s); 1.65-1.90 (4H, m); 1.91 (1H, d, 11.0 Hz); 1.94 (1H, dd, 3.1 and 8.2 Hz); 2.19 (1H, d, 15.6 Hz); 2.22 (3H, s); 2.42 (1H, m); 2.44 (1H, dd, 10.6 and 16.8 Hz); 2.78 (1H, dd, 8.2 and 18.0 Hz); 2.85 (1H, dd, 2.3 and 10.6 Hz); 3.30 (1H, dd, 3.1 and 18.4 Hz); 3.67 (3H, s); 4.83 (1H, s); 4.91 (1H, s); 5.24 (1H, s); 6.44 (1H, s); 7.36 (1H, s) and 7.46 (1H, s).

Compound 11 (GL-1203)

A solution of compound 10 (8 mg, 0.011 mmol) in a mixture of DCM and TFA (trifluoroacetic acid) (2 mL, ratio 10:1) was stirred at r.t. for 18 h and then evaporated. The residue was purified by radial chromatography on silica gel eluting with a mixture of light petroleum ether and EtOAc (2:1) to give compound 11 (4 mg, 51%) as colorless oil.

HRMS (M+H)$^+$: 699.2256, C$_{33}$H$_{38}$F$_3$O$_{13}$ requires 699.2264.

$^1$H-NMR (600 MHz, CDCl$_3$, TMS) δ; 0.96 (3H, s); 1.17 (3H, s); 1.31 (3H, 5); 1.3-1.5 (2H, m); 1.66 (3H, s); 1.84 (1H, d, 11.0 Hz); 1.96 (1H, d, 11.0 Hz); 1.9-2.1 (2H, m); 2.11 (1H, dd, 1.2 and 9.0 Hz); 2.21 (3H, s); 2.30 (1H, dd, 2.8 and 16.4 Hz); 2.49 (1H, dd, 9.4 and 16.0 Hz); 2.78 (1H, s); 2.86 (1H, dd, 9.0 and 18.4 Hz); 2.92 (1H, dd, 2.7 and 9.8 Hz); 2.99 (1H, dd, 1.6 and 18.4 Hz); 3.73 (3H, s); 4.87 (1H, s); 5.31 (1H, s); 6.09 (1H, s); 6.45-6.47 (1H, m); 7.42 (1H, s) and 7.72 (1H, s).

$^{-13}$C-NMR (150 MHz, CDCl$_3$, TMS) δ: 14.7; 15.6; 20.5; 21.1; 21.6; 23.7; 27.2; 31.2; 33.8; 37.3; 38.4; 39.7; 45.4; 45.6; 45.9; 52.0; 74.6; 75.0; 77.8; 79.3; 82.7; 83.8; 84.7; 108; 8; 114.3; 118.9; 119.3; 142.1; 143.5; 156.5; 167.5; 170.2; 172.6.

Compound 12 (GL-1243)

Acetic anhydride (10 µL, 0.105 mmol) was added to a solution of compound 10 (3 mg, 0.0042 mmol) in DCM (1 mL) followed by TFA (0.1 mL). The mixture was stirred for 3 h at r.t. and then evaporated in vacuo. Saturated NaHCO$_3$ (2 mL) was added to the residue and the product was extracted with EtOAc (2×2 mL). The extract was dried over Na$_2$SO$_4$, filtered and evaporated. The residue was purified by radial chromatography on silica gel, eluting with a mixture of HEX and EtOAc (1:1) to give compound 12 (2.2 mg, 69% as colorless oil).

HRMS (M+H)$^+$: 759.3406, C$_{39}$H$_{55}$O$_{13}$Si requires 759.3412.

$^1$H-NMR (600 MHz, CDCl$_3$, TMS): δ 0.44-0.56 (6H, m); 0.88 (9H, t, 8.0 Hz); 0.94 (3H, s); 1.10-1.30 (1H, m); 1.12 (3H, s); 1.20 (3H, s); 1.63 (3H, s); 1.64-1.80 (2H, m); 1.77 (1H, d, 11.0 Hz); 1.82-1.90 (1H, m); 1.93 (1H, dd, 2.3 and 8.6 Hz); 1.98 (1H, d, 11.3 Hz); 2.11 (3H, 5); 2.17 (1H, dd, 2.3 and 16.0 Hz); 2.26 (3H, s); 2.45 (1H, dd, 10.6 and 16.8 Hz); 2.77 (1H, dd, 9.0 and 18.4 Hz); 2.81 (1H, dd, 2.0 and 10.6 Hz); 3.42 (1H, dd, 2.7 and 18.4 Hz); 3.66 (3H, s); 4.87 (1H, 5); 5.45 (2H, s); 6.46 (1H, s); 7.35 (1H, s) and 7.48 (1H, s).

$^{13}$C-NMR (150 MHz, CDCl$_3$, TMS): δ 4.9; 5.2; 5.3; 6.6; 6.8; 7.0; 14.8; 16.0; 21.0; 20.9; 21.6; 21.8; 23.6; 24.8; 27.3; 30.4; 33.3; 35.8; 39.6; 40.4; 44.0; 46.2; 52.0; 70.6; 66.4; 74.7; 80.2; 80.9; 81.1; 83.7; 84.7; 110.8; 118.4; 125.3; 141.2; 142.6; 168.8; 170.0; 172.5.

Calculation of Over-all Yield for 7, 8 and GL-1203 Starting from Phragmalin

Based on the maximum yields in each of the steps of Example 3 approximate yields of SAE5 and R306, as follows:

| Step | Maximum yield % (fraction) |
| --- | --- |
| Compound 6 → Compound 7 | 45% (0.45) |
| Compound 7 → Compound 8 | 70% (0.70) |
| Compound 8 → Compound 9 | 63% (0.63) |
| Compound 9 → Compound 10 | 92% (0.92) |
| Compound 10 → Compound 11 (GL-1203) | 51% (0.51) |

From this we can calculate an overall yield for GL-1203 from phragmalin as follows:

Yield of 7: 0.45 (45%)

Yield of 8: 0.45×0.70=0.315 (31.5%)

Yield of GL-1203: 0.45×0.70×0.63×0.92×0.51=0.0931 (9.31%)

Example 2

Synthesis of Compounds of Structure (5) Starting from Phragmalin Via Acylated Phragmalin

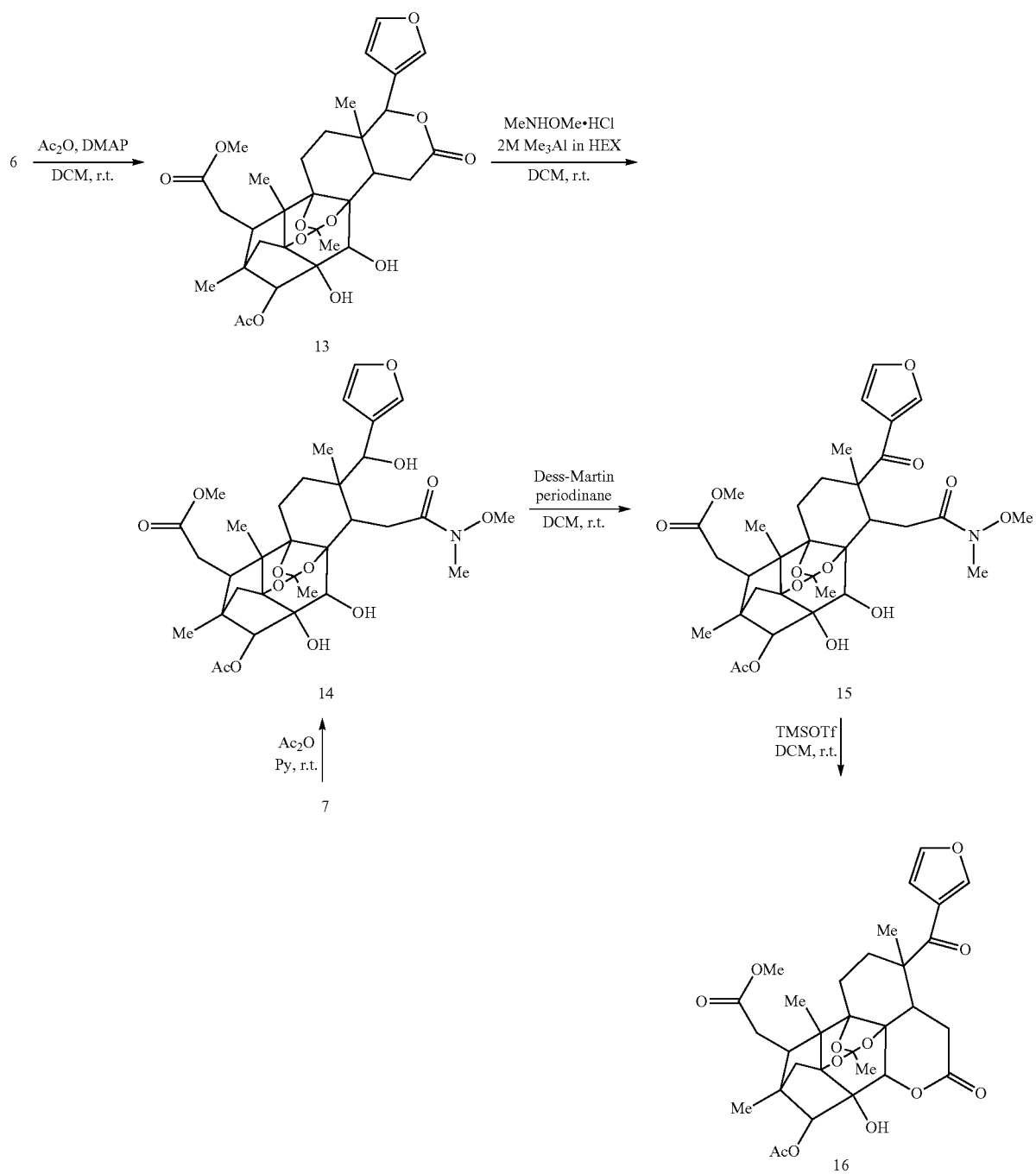

A summary of the steps is shown in Scheme 2

Compound 13

Acetic anhydride (0.17 ml, 1.8 mmol) and DMAP (4.4 mg, 0.036 mmol) was added to a solution of compound 6 (phragmalin) (100 mg, 0.18 mmol) in DCM (5 mL). The mixture was stirred for 2 h at r.t. and then partitioned between 5% aqueous $KHSO_4$ (10 mL) and EtOAc (10 mL). The organic phase was separated and dried over $Na_2SO_4$. The extract was filtered and evaporated and the residue was purified by radial chromatography on silica gel, eluting with a mixture of HEX and EtOAc (1:1 then 1:0) to give compound 13 (75 mg, 68%) as colorless oil.

HRMS (M+H)$^+$: 603.2444, $C_{31}H_{39}O_{12}$ requires 603.2441.

¹H-NMR (CDCl₃, TMS): δ 0.94 (3H, s); 1.07 (3H, s); 1.14 (3H, s); 1.20-1.30 (1H, m); 1.59 (1H, d, 11.0 Hz); 1.63 (3H, s); 1.73 (1H, d, 11.0 Hz); 1.92 (1H, d, 11.0 Hz); 1.96-1.99 (1H, m); 2.11 (3H, s); 2.26 (1H, dd, 3.1 and 16.4 Hz); 2.42 (2H, m); 2.46 (1H, dd, 9.4 and 16.4 Hz); 2.63 (1H, dd, 10.2 and 19.6 Hz); 2.86 (1H, s); 3.09 (1H, dd, 2.7 and 9.4 Hz); 3.21 (1H, d, 7.4 Hz); 3.40 (1H, dd, 1.6 and 19.2 Hz); 3.71 (3H, s); 4.57 (1H, d, 7.4 Hz); 4.70 (1H, s); 5.54 (1H, s); 6.49 (1H, d, 1.6 Hz); 7.42 (1H, t, 1.8 Hz) and 7.52 (1H, s).

Note that the conversion of 6 to 13 is an example of regioselective acylation of the hydroxy group at the carbon at position 3 over the hydroxy groups at carbon 2 and 30; this regioselective acylation was necessary to afford protection of the hydroxy group at carbon 3 as when it was unprotected, in the following oxidation step (see below) it resulted in the unwarranted oxidation of the hydroxy group at carbon 3 which led to the destruction of the entire phragmalin skeleton. Moreover, the regioselective acylation leaving the hydroxy group at carbon 30 unaffected was a necessary feature to allow the closing of the lactone ring with this hydroxy group (see below). Thus, accordingly the regioselective acylation demonstrated in this step and its generalization as described in this patent above, is an important feature provided by this invention, which was not foreseeable by any prior art. [Atom numberings are as in structure (2b) above.]

Compound 14

Method A, from Compound 7:

A solution of compound 7 (65 mg, 0.1 mmol) in a mixture of pyridine (Py) (2 mL) and acetic anhydride (0.65 mL) was stirred for 11 h at r.t. The mixture was diluted with 10% KHSO₄ (20 mL) and the product was taken up into EtOAc (10 mL). The organic phase was separated, dried over Na₂SO₄ and evaporated. The product was purified by radial chromatography on silica gel, eluting with EtOAc to give compound 14 (15 mg, 22%) as colorless oil.

Method B, from Compound 13:

A suspension of MeNHOMe.HCl (121 mg, 1.24 mmol) in DCM (10 mL) was cooled in an ice bath and to this was added dropwise 2 M Me₃Al in HEX (1.24 mL, 2.48 mmol). After the addition was complete, the cooling bath was removed and the reaction was stirred for 15 min. The mixture was cooled again in an ice bath and to this was added a solution of compound 13 (75 mg, 0.124 mmol) in DCM (5 mL). The cooling bath was removed and the reaction mixture was stirred at r.t. for 30 min, then cooled again in an ice bath. An aqueous solution of Rochelle's salt (100 mL) was added and the organic phase was separated. The aqueous phase was extracted with EtOAc (3×20 mL) and the combined organic phase dried over Na₂SO₄. The solution was evaporated in vacuo and the residue was purified by flash chromatography on silica gel, eluting with EtOAc to give compound 14 (27 mg, 33%) as colorless oil.

HRMS (M+H)⁺: 664.2959, $C_{33}H_{46}NO_{13}$ requires 664.2969

¹H-NMR (CDCl₃, TMS): δ 0.93 (3H, s) 1.10 and 1.11 (total 6H, both s); 1.40 (1H, broad t, 14.9 Hz); 1.56 (3H, s); 1.60-1.73 (2H, m); 1.85 (1H, dt, 2.8 and 14.6 Hz); 1.90 (1H, d, 11.0 Hz); 2.16-2.26 (1H, m); 2.21 (3H, s); 2.37-2.46 (2H, m); 2.45 (1H, m); 2.84-3.08 (4H, m); 3.18 (3H, s); 3.40-3.54 (2H, m); 3.66 (3H, s); 3.71 (3H, s); 4.54 (1H, d, 8.4 Hz); 4.72 (1H, s); 5.21 (1H, s); 6.53 (1H, d, 1.5 Hz); 7.37 (1H, t, 1.5 Hz) and 7.48 (1H, s).

Compound 15

A 0.39 M solution of Dess-Martin periodinane (1,1,1-triacetoxy-1,1-dihydro-1,2-benziodoxol-3(1H)-one) in DCM (0.18 mL, 0.069 mmol) was added to a solution of compound 14 (15 mg, 0.023 mmol) in DCM (1.8 mL). The reaction mixture was stirred at r.t. for 30 min and then diluted with 10% aqueous sodium hydrosulfite (Na₂S₂O₄) (10 mL). The product was extracted with EtOAc (3×10 mL) and the combined organic phase dried over Na₂SO₄. The extract was evaporated and the residue was purified by radial chromatography on silica gel, eluting with EtOAc to give compound 15 (8.2 mg, 54%) as colorless oil.

HRMS (M+H)⁺: 662.2807, $C_{33}H_{44}NO_{13}$ requires 662.2812.

¹H-NMR (CDCl₃, TMS): δ 0.92 (3H, s); 1.14 (3H, s); 1.24-1.27 (4H, m); 1.52 (3H, s); 1.70 (1H, d, 11.0 Hz); 1.73 (1H, dt, 4.3 and 14.9 Hz); 1.88 (1H, d, 10.6 Hz); 2.17 (3H, s); 2.28 (1H, dd, 3.5 and 16.0 Hz); 2.32-2.54 (3H, m); 2.43 (2H, m); 2.69 (1H, br t, 4.3 Hz); 2.92-3.00 (2H, m); 3.13 (3H, s); 3.61 (3H, s); 3.62 (3H, s); 3.70-3.77 (1H, m); 4.43 (1H, d, 6.7 Hz); 4.66 (1H, s); 6.80 (1H, d, 2.0 Hz); 7.42 (1H, t, 1.2 Hz) and 8.00 (1H, s).

Compound 16 (SAE6)

Trimethylsilyltrifluoromethanesulfonate (TMSOTf) (7 μL, 0.038 mmol) was added to a solution of compound 15 (5 mg, 0.0076 mmol) in DCM (1 mL). The mixture was stirred at r.t. for 17 h and diluted with saturated aqueous NaHCO₃ (3 mL). The product was extracted with EtOAc (3×3 mL) and the combined organic phase dried over Na₂SO₄. The extract was evaporated and the residue was purified by preparative TLC on silica gel eluting with EtOAc to give compound 16 (2 mg, 44%) as colorless oil.

Note: The reaction was repeated two additional times starting with 7-14 mg of compound 15, and with the reaction time being 2 h. Yields compound 16 were 43%. Using of ZnCl₂ or BF₃.Et₂O or mixture of THF and 5% aqueous KHSO₄ instead of TMSOTf did not result in the desired product 16.

HRMS (M+H)⁺: 601.2280, $C_{31}H_{37}O_{12}$ requires 601.2285.

¹H-NMR (600 MHz, CDCl₃), TMS): δ0.91 (3H, s); 1.11 (3H, s); 1.49 (3H, s); 1.20-1.40 (1H, m); 1.67 (3H, s); 1.78-1.85 (2H, m); 1.93 (1H, d, 11.0 Hz); 1.96 (1H, dd, 3.9 and 8.6 Hz); 2.11 (1H, dd, 3.1 and 16.0 Hz); 2.15-2.22 (2H, m); 2.29 (3H, s); 2.31-2.36 (1H, M); 2.61 (1H, dd, 3.5 and 9.8 Hz); 2.73 (1H, dd, 3.1 and 17.6 Hz); 2.79 (1H, dd, 8.2 and 17.6 Hz); 2.89 (1H, s); 3.54 (3H, s); 4.82 (1H, s); 5.41 (1H, s); 7.43 (1H, s); 7.43 (1H, s) and 8.08 (1H, s).

¹³C-NMR (150 MHz, CDCl₃, TMS): δ 14.7; 15.4; 20.8; 21.3; 23.6; 24.8; 24.9; 28.0; 31.6; 33.7; 36.5; 39.9; 44.9; 45.9; 48.9; 51.4; 51.5; 79.8; 74.9; 77.7; 83.1; 84.0; 84.4; 109.8; 118.9; 124.3; 143.3; 146.8; 168.8; 172.2; 199.0.

Calculation of Over-all Yield for 14, 15 and SAE6 Starting from Phragmalin

Based on the maximum yields in each of the steps of Example 3 approximate yields of SAE5 and R306, as follows:

| Step | Maximum yield % (fraction) |
|---|---|
| Compound 6 → Compound 13 | 68% (0.68) |
| Compound 13 → Compound 14; Method B | 33% (0.33) |
| Compound 14 → Compound 15 | 54% (0.54) |
| Compound 15 → Compound 16 (SAE6) | 44% (0.44) |

From this we can calculate an overall yield for compound 14, 15 and SAE6 from phragmalin as follows:

Yield of 14: 0.68×0.33=0.2244 (22.44%)

Yield of 15: 0.68×0.33×0.54=0.1211 (12.11%)

Yield of SAE6: 0.68×0.33×0.54×0.44=0.0533 (5.33%)

Example 3
Synthesis of Compounds of Structure (5) Starting from Phragmalin Via Isobutyrylated Phragmalin
Scheme 3
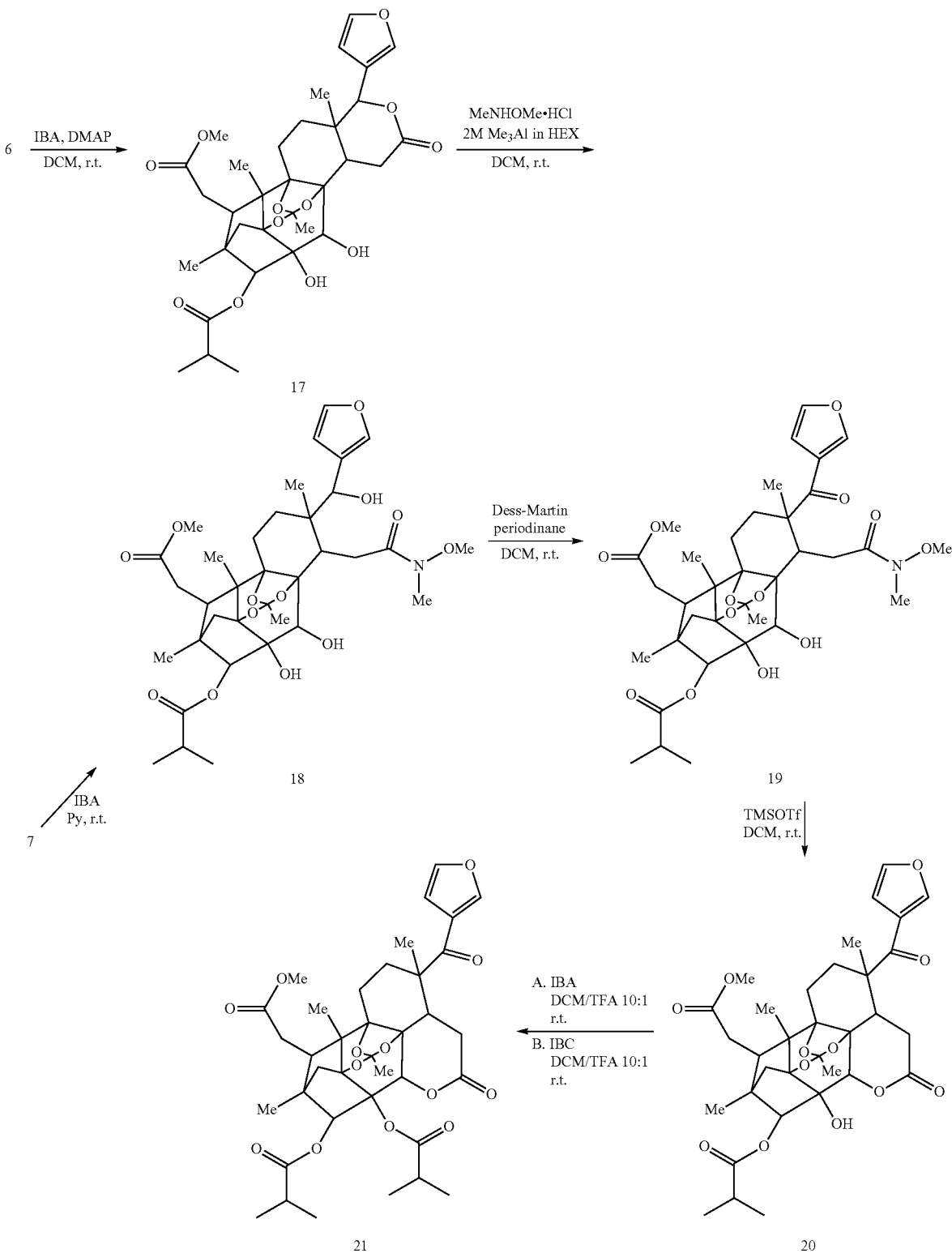
A summary of the steps is shown in Scheme 3.

Compound 17

Isobutyric anhydride [IBA; $(CH_3)_2CHCO)_2O$], (0.3 mL, 1.8 mmol) and DMAP (4.4 mg, 0.036 mmol) was added to a solution of compound 6 (phragmalin) (100 mg, 0.18 mmol) in DCM (5 mL). The mixture was stirred for 2 h at r.t. and then partitioned between 5% aqueous $KHSO_4$ (10 mL) and EtOAc (10 mL). The organic phase was separated and dried over $Na_2SO_4$. The extract was filtered and evaporated and the residue was purified by radial chromatography on silica gel, eluting with a mixture of HEX and EtOAc (1:1 then 1:0) to give compound 17 as colorless oil.

Note: This reaction was repeated five times, with yields 56% to 93% of compound 17, starting with 100 to 200 mg of compound 6.

HRMS $(M+H)^+$: 631.2751, $C_{33}H_{43}O_{12}$ requires 631.2754.

$^1$H-NMR (400 MHz, $CDCl_3$, TMS): δ 0.94 (3H, s); 1.04 (3H, s); 1.15 (3H, s); 1.17-1.19 (1H, m); 1.20 (6H, dd, 2.3 and 7.0 Hz); 1.62-1.65 (1H, m); 1.63 (3H, s); 1.74 (1H, d, 10.6 Hz); 1.93 (1H, d, 10.6 Hz); 1.97 (1H, dd, 1.6 and 10.2 Hz); 2.26 (1H, dd, 2.7 and 16.4 Hz); 2.47 (1H, dd, 9.4 and 16.4 Hz); 2.43 (2H, m); 2.59 (1H, septet, 7.0 Hz); 2.62 (1H, dd, 10.2, 19.2 Hz); 2.86 (1H, t, 3.5 Hz); 3.11 (1H, dd, 2.7 and 9.4 Hz); 3.19 (1H, d, 7.0 Hz); 3.41 (1H, dd, 1.6 and 19.2 Hz); 3.70 (3H, s); 4.58 (1H, d, 7.0 Hz); 4.69 (1H, s); 5.55 (1H, s); 6.48 (1H, d, 1.6 Hz); 7.42 (1H, t, 1.6 Hz) and 7.51 (1H, s).

$^{13}$C-NMR (100 MHz, $CDCl_3$, TMS): δ 14.3; 16.0; 18.5; 18.9; 19.9; 21.2; 25.2; 27.1; 29.1; 33.7; 34.4; 34.5; 37.2; 39.5; 42.2; 45.3; 45.6; 52.0; 69.1; 77.8; 78.4; 82.7; 84.1; 86.1; 86.8; 109.6; 119.0; 121.4; 140.2; 142.8; 171.1; 172.9; 175.9.

Compound 18

Method A, from Compound 7:

A solution of compound 7 (65 mg, 0.1 mmol) in a mixture of Py (2 mL) and IBA (0.166 mL, 1.0 mmol) was stirred for 11 h at r.t. The mixture was diluted with 10% $KHSO_4$ (20 mL) and the product was taken up into EtOAc (10 mL). The organic phase was separated, dried over $Na_2SO_4$ and evaporated. The product was purified by radial chromatography on silica gel, eluting with EtOAc to give compound 18 as colorless oil. However, the yield of compound 18 according to this route was low due to formation of many side products.

Method B, from Compound 17:

A suspension of MeNHOMe.HCl (121 mg, 1.24 mmol) in DCM (10 mL) was cooled in an ice bath and to this was added dropwise 2 M $Me_3Al$ in HEX (1.24 mL, 2.48 mmol). After the addition was complete, the cooling bath was removed and the reaction was stirred for 15 min. The mixture was cooled again in an ice bath and to this was added a solution of compound 17 (75 mg, 0.119 mmol) in DCM (5 mL). The cooling bath was removed and the reaction mixture was stirred at r.t. for 30 min and then cooled again in an ice bath. An aqueous solution of Rochelle's salt (100 mL) was added and the organic phase was separated. The aqueous phase was extracted with EtOAc (3×20 mL) and the combined organic phase dried over $Na_2SO_4$. The solution was evaporated in vacuo and the residue was purified by flash chromatography on silica gel, eluting with EtOAc to give compound 18 as colorless oil.

Note: The reaction according to the principle of Method B of this Example was repeated 13 additional times with systematic variations of the molar ratio of $Me_3Al$ versus MeNHOMe.HCl, starting with between 100-200 mg of compound 17 and using reaction times between 30 min to 16 hours at r.t.; the yield of compound 18 reaching maximally 39%.

Note: For the sake of this patent Method B of this Example is preferred, which starts from compound 17, over the Method A of this example which starts from compound 7, to obtain compound 18.

HRMS $(M+H)^+$: 692.3287, $C_{35}H_{50}NO_{13}$ requires 692.3282.

$^1$H-NMR (400 MHz, $CDCl_3$, TMS): δ 0.93 (3H, s); 1.09 (3H, s); 1.11 (3H, s); 1.26 (6H, dd, 7.0 and 8.6 Hz); 1.44 (1H, broad t, 14.9 Hz); 1.56 (3H, s); 1.69-1.77 (2H, m); 1.83-1.90 (1H, m); 1.91 (1H, d, 10.6 Hz); 2.24 (1H, dd, 2.7 and 16.4 Hz); 2.40-2.47 (2H, m); 2.67 (1H, septet, 7.0 Hz); 2.83 (1H, br s); 2.85 (1H, br s); 2.86 (1H, s); 2.96 (1H, dd, 5.9 and 15.7 Hz); 3.07 (1H, dd, 2.3 and 10.2 Hz); 3.17 (3H, s); 3.38 (1H, d, 9.0 Hz); 3.48 (1H, bs); 3.66 (3H, s); 3.71 (3H, s); 4.58 (1H, d, 8.6 Hz); 4.72 (1H, s); 5.17 (1H, d, 3.1 Hz); 6.53 (1H, d, 1.6 Hz); 7.37 (1H, t, 1.6 Hz) and 7.49 (1H, s).

$^{13}$C-NMR (100 MHz, $CDCl_3$, TMS): δ 14.3; 15.9; 18.9; 20.0; 23.4; 20.8; 25.4; 29.0; 29.7; 32.2; 32.6; 34.0; 34.4; 37.2; 39.6; 40.0; 45.3; 45.5; 46.0; 51.9; 61.3; 70.0; 70.6; 78.1; 83.1; 84.0; 86.8; 88.4; 110.3; 118.6; 126.9; 140.0; 142.3; 172.7; 176.3.

Demonstration of the Requirements for Very Distinct Conditions for Formation of the Weinreb Amide 18 from 17

To afford 18 from 17 very distinct conditions were required; this amounted to applying the correct molar ratios of MeNHOMe.HCl, $Me_3Al$ and 17, as well as selection of narrow range of timing as is evident from the 12 experiments (denoted #1-10) in the below table. (Conditions for the experiments were as follows: for all 12 experiments 25 mg of compound 17; for experiments #1-10 MeNHOMe.HCl: $Me_3Al$ was varied as indicated in the below table; all other conditions as detailed above "Method B, from compound 17"). Moreover, in experiment #11 $Me_3Al$ was exchanged for $Me_2AlCl$ and in experiment #12 $Me_3Al$ was exchanged for $Et_3Al$; all other conditions were as under "Method B, from compound 17":

| # | Reagent | MeNHOMe•HCl | Time, h | Yield of 18, % | Recovery of 17, % |
|---|---|---|---|---|---|
| 1 | $Me_3Al$ (2 equiv.) | 1.5 equiv. | 0.5 | 0 | 87 |
| 2 | $Me_3Al$ (10 equiv.) | 5 equiv. | 1 | 14 | 70 |
| 3 | $Me_3Al$ (10 equiv.) | 5 equiv. | 1.5 | 37 | 26 |
| 4 | $Me_3Al$ (10 equiv.) | 5 equiv. | 16 | 0 | 17 was not attempted to be recovered |
| 5 | $Me_3Al$ (10 equiv.) | 5 equiv. | 16 | 11 | 14 |
| 6 | $Me_3Al$ (20 equiv.) | 10 equiv. | 0.5 | 39 | 28 |
| 7 | $Me_3Al$ (20 equiv.) | 10 equiv. | 1 | 32 | 35 |
| 8 | $Me_3Al$ (20 equiv.) | 10 equiv. | 1.5 | 0 | 98 |
| 9 | $Me_3Al$ (20 equiv.) | 10 equiv. | 2 | 0 | 93 |
| 10 | $Me_3Al$ (30 equiv.) | 15 equiv. | 1 | 12 | 39 |
| 11 | $Me_2AlCl$ (6 equiv.) | 5 equiv. | 1 | 0 | 82 |
| 12 | $Et_3Al$ (10 equiv.) | 5 equiv. | 6 | 0 | 73 |

Thus, as seen from the table with low equivalent amounts of $Me_3Al$ and MeNHOMe.HCl the desired product 18 was not formed, as well as with high equivalent amounts of $Me_3Al$ and MeNHOMe.HCl the yield dropped sharply. The optimal ratio of $Me_3Al$: MeNHOMe.HCl is 2:1 and there is a narrow time window depending on the molar ratio of $Me_3Al$:MeNHOMe.HCl. With too short time no desired product 18 is formed while also with too long reaction times no desired product 18 is formed. The highest yield of 18, 39%, was achieved for experiment #6. Note that for experiment #6 28% of the starting material 17 was recovered, which can be entered once again in the process, thus effectively increasing the total yield for 18 beyond the above-mentioned yield of 39%, for the process when it is iteratively repeated.

Note also that exchanging $Me_3Al$ with $Me_2AlCl$ (#11) or $Et_3Al$ (#12) as catalyst was unsuccessful; this further demonstrates the strict requirement of additive for the reaction to proceed in producing the desired product 18.

Compound 19 (LG-1725)

A 0.39 M solution of Dess-Martin periodinane in DCM (0.18 mL, 0.069 mmol) was added to a solution of compound 18 (15 mg, 0.022 mmol) in DCM (1.8 mL). The reaction mixture was stirred at r.t. for 30 min and diluted with 10% aqueous $Na_2S_2O_4$ (10 mL). The product was extracted with EtOAc (3×10 mL) and the combined organic phase was dried over $Na_2SO_4$. The extract was evaporated and the residue was purified by radial chromatography on silica gel, eluting with EtOAc to give compound 19 as colorless oil.

Note: This reaction was repeated six times starting with 23-49 mg of compound 18 using between 30 min to one hour reaction time at r.t., with yields of compound 19 54-90%.

HRMS (M+H)$^+$: 690.3129, $C_{35}H_{48}NO_{13}$ requires 690.3126.

$^1$H-NMR (400 MHz, CDCl$_3$, TMS): δ 0.86 (3H, s); 1.12 (3H, s); 1.20 (6H, dd, 1.6 and 7.0 Hz); 1.51 (3H, s); 1.55 (3H, s); 1.71 (1H, d, 11.0 Hz); 1.83-1.98 (3H, m); 2.20-2.27 (2H, m); 2.24 (1H, m); 2.36-2.45 (2H, m); 2.61 (1H, septet, 7.0 Hz); 2.74 (1H, t, 4.7 Hz); 2.87 (1H, dd, 3.1 and 9.4 Hz); 3.03-3.12 (1H, m); 3.14 (3H, s); 3.57 (3H, s); 3.65 (3H, s); 3.70 (1H, bs); 4.11 (1H, bs); 4.35 (1H, d, 5.1 Hz); 4.69 (1H, 5); 6.76 (1H, d, 2.0 Hz); 7.42 (1H, t, 1.6 Hz) and 8.0 (1H, s).

$^{13}$C-NMR (100 MHz, CDCl$_3$, TMS): δ 14.6; 15.9; 18.6; 18.8; 20.7; 24.8; 25.5; 28.3; 31.3; 32.4; 34.2; 34.4; 36.8; 39.6; 44.4; 45.2; 45.7; 50.4; 51.7; 61.2; 68.7; 78.1; 83.7; 84.2; 86.2; 87.6; 110.6; 118.7; 125.9; 143.1; 146.9; 171.1; 172.8; 175.9 and 200.7.

Figure 5:
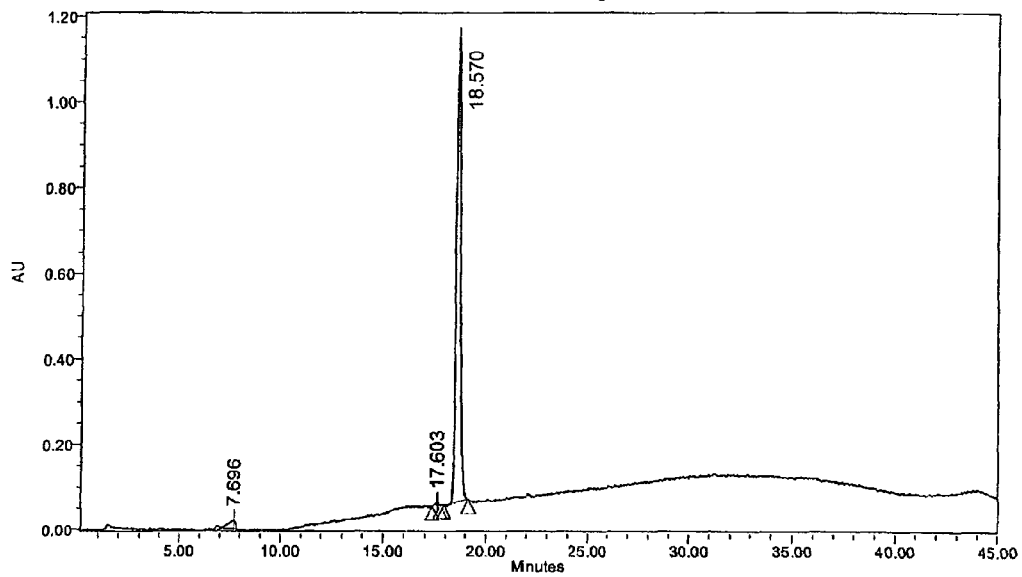

Analytical HPLC of LG-1725 was performed on a Waters system (Millenium32 workstation, 2690 separation module, 996 photodiode array detector) equipped with HiChrom LiChrospher RP18-5 (4.6×250 mm) column. The flow rate was 0.3 mL/min, UV detection at 220 nm for purity control, eluent MeCN/water with gradient from 37% to 100% MeCN during 45 min. LG-1725 was eluted at 18.57 min; purity better than 95% (FIG. 5); UV-absorption maxima at 198.4 and 258.5 nM.

Compound 20 (SAE5)

TMSOTf (7 μL, 0.038 mmol) was added to a solution of compound 19 (5 mg, 0.0072 mmol) in DCM (1 mL). The mixture was stirred at r.t. for 17 h and diluted with saturated aqueous NaHCO$_3$ (3 mL). The product was extracted with EtOAc (3×3 mL) and the combined organic phase dried over Na$_2$SO$_4$. The extract was evaporated and the residue purified by preparative TLC on silica gel eluting with EtOAc to give compound 20 (SAE5) as colorless oil.

Note: This reaction was repeated four times starting with 21-39 mg of compound 19, and with the reaction time being only 30 min. Yields of compound 20 varied between 35-50%.

HRMS (M+H)$^+$: 629.2590, $C_{33}H_{41}O_{12}$ requires 629.2598.

$^1$H-NMR (400 MHz, CDCl$_3$, TMS): δ 0.90 (3H, s); 1.11 (3H, s); 1.13-1.28 (1H, m); 1.38 (6H, d, 7.0 Hz); 1.48 (3H, s); 1.67 (3H, s); 1.73-1.85 (2H, m); 1.94 (1H, d, 11 Hz); 1.96 (1H, dd, 3.9 and 9.0 Hz); 2.11 (1H, dd, 2.7 and 15.7 Hz); 2.17-2.24 (2H, m); 2.31 (1H, dd, 9.8 and 15.7 Hz); 2.60 (1H, dd, 3.1 and 9.8 Hz); 2.69-2.81 (3H, m); 2.91 (1H, s); 3.52 (3H, s); 4.82 (1H, s); 5.38 (1H, s); 6.79 (1H, d, 1.2 Hz); 7.43 (1H, t, 1.6 Hz) and 8.1 (1H, s).

$^{13}$C-NMR (100 MHz, CDCl$_3$, TMS): δ 14.7; 15.6; 18.7; 18.8; 21.5; 24.9; 25.0; 28.1; 31.8; 33.9; 34.7; 37.1; 40.0; 45.3; 46.1; 49.1; 51.5; 51.6; 75.1; 77.9; 79.9; 83.1; 84.1; 84.3; 110.0; 119.0; 124.4; 143.5; 147.0; 168.7; 172.4; 175.9 and 199.1.

Figure 6:
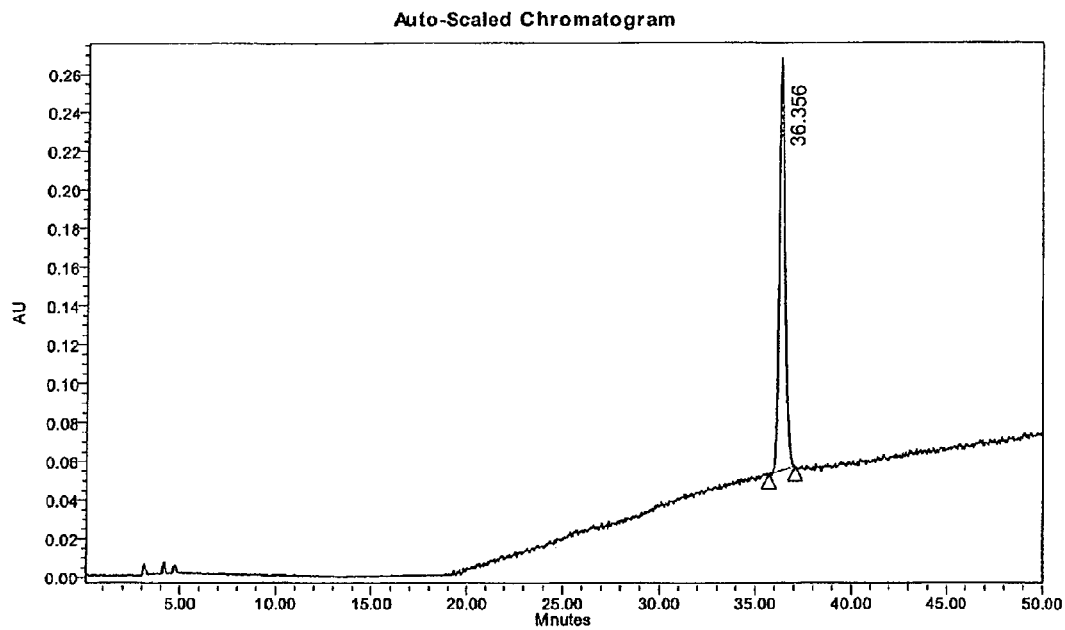

Analytical HPLC of SAE5 was performed on a Waters system (Millenium32 workstation, 2690 separation module, 996 photodiode array detector) equipped with HiChrom LiChrospher RP18-5 (4.6×250 mm) column. Flow rate 0.3 mL/min, UV detection at 220 nm for purity check, eluent MeCN/water with gradient from 40% to 90% MeCN during 50 min. Elution time was 36.36 min, purity 100.0% (FIG. 6). UV absorption maxima at 198.4 and 259.7 nM; sharp shoulder at 215.2 nM Compound 21 (R306)

Method A:

Compound 20 (5 mg, 0.00796 mmol) was dissolved in a mixture of DCM and TFA (10:1, 1 mL) and IBA (13.2 μL, 0.08 mmol) was added. The mixture was stirred at r.t. for 16 h and then diluted with saturated aqueous NaHCO$_3$ (3 mL). The product was extracted with EtOAc (3×3 mL) and the combined organic phase dried over Na$_2$SO$_4$. The extract was evaporated and the residue purified by preparative TLC on silica gel eluting with EtOAc to give compound 21 (4.6 mg, 83%) as colorless oil.

Note: Method A of this Example was repeated two additional times starting with 5-8 mg of compound 20, however with the exchange of TFA to TMSOTf (1 eq); the amount of isobutyric anhydride (IBA) used being 10 equivalents and the reaction time being 30 min at r.t.; with yields of compound 21 80-94%.

Method B:

Compound 20 (5 mg, 0.00796 mmol) was dissolved in a mixture of DCM and TFA (10:1, 1 mL) and isobutyryl chloride [IBC; (CH$_3$)$_2$CC(O)Cl], (8.5 μL, 0.08 mmol) was added. The mixture was stirred at r.t. for 16 h, diluted with saturated aqueous NaHCO$_3$ (3 mL). The product was extracted with EtOAc (3×3 mL) and the combined organic phase dried over Na$_2$SO$_4$. The extract was evaporated and the residue purified by preparative TLC on silica gel eluting with EtOAc to give compound 21 (4.8 mg, 86%) as colorless oil.

HRMS (M+H)$^+$: 699.2992, $C_{37}H_{47}O_{13}$ requires 699.3016.

$^1$H NMR (600 MHz, CDCl$_3$, 25° C.): δ 0.9 (3H, s), 1.10 (3H, s), 1.16 (3H, d, J=6.9 Hz), 1.19 (3H, d, J=6.9 Hz), 1.37 (3H, d, J=7.4 Hz), 1.38 (3H, d, J=7.4 Hz), 1.39 (1H, m), 1.48 (3H, s), 1.62 (3H, s), 1.80 (1H, d, J=11.1 Hz), 1.83 (1H, m), 1.96 (1H, dd, J=1.7, 8.1 Hz), 2.00 (1H, d, J=11.1 Hz), 2.08 (1H, dd, J=9.8, 15.5), 2.11 (1H, m), 2.17 (1H, m), 2.32 (1H, dd, J=2.4, 15.5 Hz), 2.54 (1H, dd, J=2.4, 9.8 Hz), 2.59 (1H, septet, J=6.9 Hz), 2.71 (1H, m), 2.73 (1H, m), 2.78 (1H, septet, J=7.4 Hz), 3.51 (3H, s), 5.37 (1H, s), 5.87 (1H, s), 6.79 (1H, dd, J=1.9, 0.8 Hz), 7.41 (1H, dd, J=1.9, 1.4 Hz), 8.06 (1H, dd, J=1.4, 0.8 Hz).

$^{13}$C NMR (150.9 MHz, CDCl$_3$, 25° C.): δ 199.0 (C$_{17}$), 175.8 (C=O), 175.3 (C=O), 172.3 (C$_7$), 169.0 (C$_{16}$), 147.1 (C$_{21}$), 143.4 (C$_{23}$), 124.6 (C$_{20}$), 118.6 (C$_{31}$), 110.1 (C$_{22}$), 84.4 (C$_1$), 83.7 (C$_9$), 83.3 (C$_2$), 80.4 (C$_{17}$), 79.7 (C$_8$), 74.8 (C$_{30}$), 51.7 (CH$_3$O—), 51.6 (C$_{13}$), 49.1 (C$_{14}$), 46.6 (C$_{10}$), 46.2 (C$_4$), 40.8 (C$_{29}$), 35.9 (C$_5$), 35.1 (CH), 34.8 (CH), 33.6 (C$_6$), 31.4 (C$_{12}$), 28.4 (C$_{15}$), 25.0 (C$_{11}$), 24.5 (C$_{18}$), 21.3 (C$_{32}$), 19.0 (CH$_3$), 18.9 (CH$_3$), 18.6 (CH$_3$), 18.5 (CH$_3$), 16.0 (C$_{19}$), 15.0 (C$_{28}$).

Calculation of Over-all Yield for Compound 18, 19, SAE5 and R306 Starting from Phragmalin Based on the maximum yields in each of the steps of Example 3 approximate yields of SAE5 and R306 can be calculated as follows:

| Step | Maximum yield % (fraction) |
|---|---|
| Compound 6 → Compound 17 | 93% (0.93) |
| Compound 17 → Compound 18; Method B | 37% (0.39) |

| Step | Maximum yield % (fraction) |
| --- | --- |
| Compound 18 → Compound 19 | 90% (0.90) |
| Compound 19 → Compound 20 (SAE5) | 50% (0.50) |
| Compound 20 → Compound 21 (R306); Method A | 94% (0.94) |

From this we can calculate an overall yields as follows:
Yield of 18: 0.93×0.39=0.3627 (36.37%)
Yield of 19: 0.93×0.39×0.90=0.3264 (33.64%)
Yield of SAE5: 0.93×0.39×0.90×0.50=0.1632 (16.32%)
Yield of R306: 0.93×0.39×0.90×0.50×0.94=0.1534 (15.34%)

Example 4

Aggression Inducing Effect of Compound 19 (LG-1725)

Compound 19 (LG-1725) of Example 3 was dissolved in olive oil and injected subcutaneously into six male mice on each day for three consecutive days at the dose 0.4 mg/kg (in 100 µl olive oil). Six control mice were sham operated and injected with olive oil only. The treatment was then stopped. On day 4, 7 and 14 the animals were then introduced to a female mice primed with 50 µg/kg β-estradiol 48 hours before the start of the test, and then with 2 mg/kg progesterone 4½ hours before the test, each by subcutaneous injection (compounds dissolved in olive oil) at a volume of 1 ml/kg, in order to make them sexually receptive, with the purpose of performing a standard sexual behavior test, using the method described in Example 5.

To our very large surprise LG-1725 did not induce any augmented sexual behavior as had been hoped for; instead it induced extreme aggressive behavior of a type that is not present in normal male mice. Thus, normal male mice introduced to a sexually receptive female will not at all or only occasionally show aggressive behavior directed to the female; instead mountings and other sexual activity is seen. However, the LG-1725 treated animals showed a pronounced aggressive behavior directed to the female which amounted to physical attacks directed towards the female, comprised of attack bites of the female and offensive leaps (including sideways leaps) towards the female. The number of these types of aggressive attacks (irrespectively of type) was counted over a period of 1 hour following the introduction of the male mice to the female mice. The results are shown in FIG. 1 for the LG-1725 treated group and compared with the sham-operated (control) group. As seen from the figure, on the $4^{th}$ day the average number of aggressive behaviors amounted to 15.0 for the LG-1725 treated group during the 1 h observation period; the number of aggressive attacks ranging between 9 to 17 for the individual six animals in the group). This contrasted sharply to the control group for which the average number of aggressive behaviors amounted to 0.33 (which in fact were none for all males except one which showed two aggressive attacks during the 1 h observation period). The effect induced by LG-1725 at the $4^{th}$ day was highly statistically significant ($p<0.0001$; Student's unpaired t-test); the aggression effect induced by LG-1725 is calculated to be 100×(15−0.33)/0.33=4445%; LG-1725 accordingly being an aggression inducing compound.

At day 7 the LG-1725 treated animals still showed a clear aggressive behavior, the average number of attacks being 4.0 over the 1 h observation period, while there were none in the control group. Also this was a highly statistically significant effect ($p<0.005$; Student's unpaired t-test).

At day 14 there was a tendency for some aggressive behavior in the treated animals, the average number of attacks being 0.8 over the one-hour observation period, while there were none in the control group. However, this was not a significant difference ($p=0.8$; Student's unpaired t-test).

Example 5

Sexual Enhancing Activities of GL-1203, SAE6 and SAE5

Animals

Mice of 9 weeks age weighing 30±2 g were used throughout the study. They were all sexually unskilled. At 4 weeks of age they had been separated from their parents and males and females had been placed in separated cages. The mice were fed with pellets enriched with proteins and lipids.

Sexual Behavior Test

Prior to the tests, male and female mice received specific treatments, as follows:

Each male mouse received 0.04, 0.4 or 4 mg/kg of GL-1203 or 0.004, 0.04, 0.4 or 4 mg/kg SAE6 by subcutaneous injection of the compound dissolved in olive oil on each day for three consecutive days (the days being termed D-1, D-2 and D-3). The injection volume was 100 µl. The treatment was then stopped. Control male mice received the identical treatment schedule with subcutaneous olive oil only.

In another set of experiments SAE5 was administered orally to male mice dissolved in olive oil (0.5 ml) at doses 0.004, 0.04, 0.4 or 4 mg/kg on each day for three consecutive days (i.e. D-1, D-2 and D-3). The treatment was then stopped. Control male mice received the identical treatment schedule with oral olive oil only.

The number of animals in each treatment and dosing group was from 5 to 6.

The GL-1203 used was prepared as described in Example 1 (compound 11); SAE6 was prepared as described in Example 2 (compound 16); SAE5 was prepared as shown in Example 3 (compound 20).

Female mice were first treated with 50 µg/kg β-estradiol 48 hours before the test, and then with 2 mg/kg progesterone 4½ hours before the test, each by subcutaneous injection (compounds dissolved in olive oil) at a volume of 1 ml/kg.

The behavioral test was performed in a dark room at ambient temperature, during the last enlightened period of the day (3.00 pm) and the first dark period of the night (7.00 pm). Each observation period lasted 4 hours.

At the fourth, seventh and fourteenth day (D-4, D-7 and D-14), the male control mice and the treated male mice were individually placed in Plexiglass cages, 30 min before the start of the test.

At 3.00 pm, a female mouse was introduced into each cage hosting a male mouse. The number of mounts of the male mouse, defined as a tentative of lateral or dorsal mounting on the female mouse with or without penis intromission, was then counted during a one-hour observation period and used as a simple measure of sexual behavior activity.

In case a female was sexually non-receptive it was immediately replaced with a new female mouse.

Results

Figure 2:
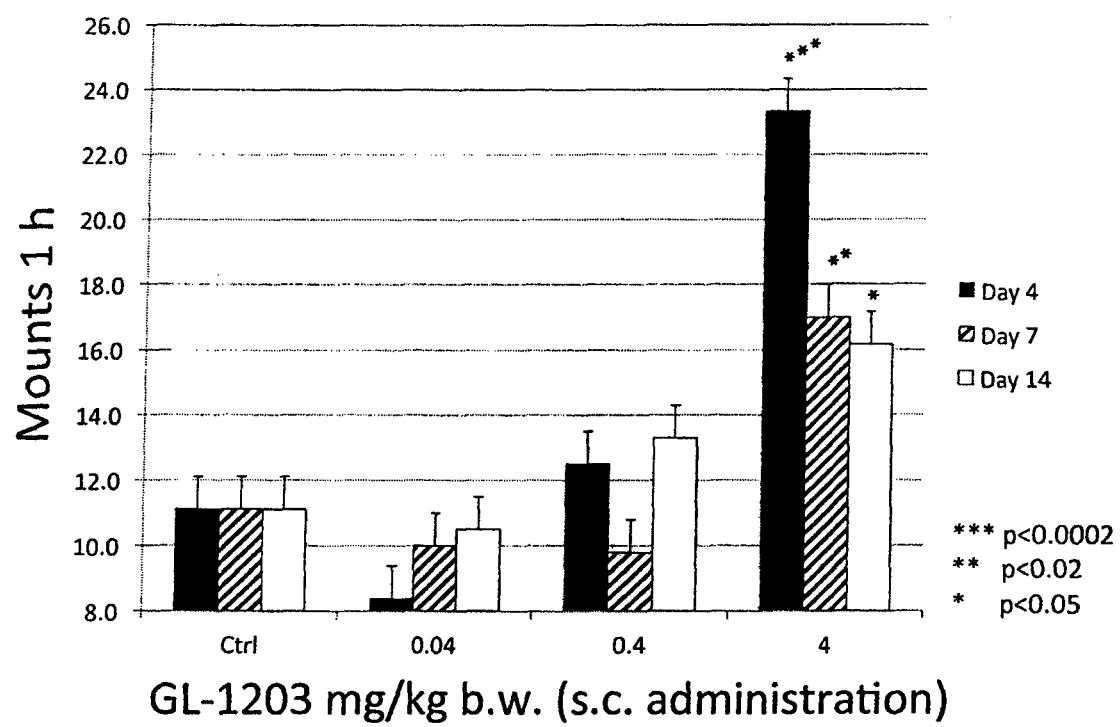
Figure 3:
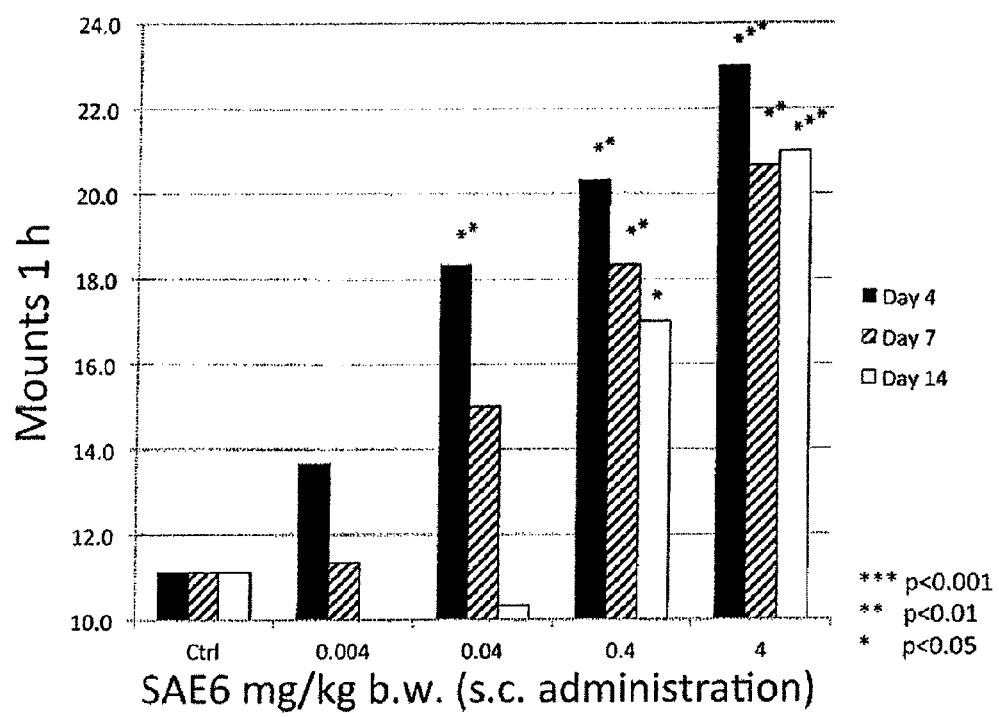
Figure 4:
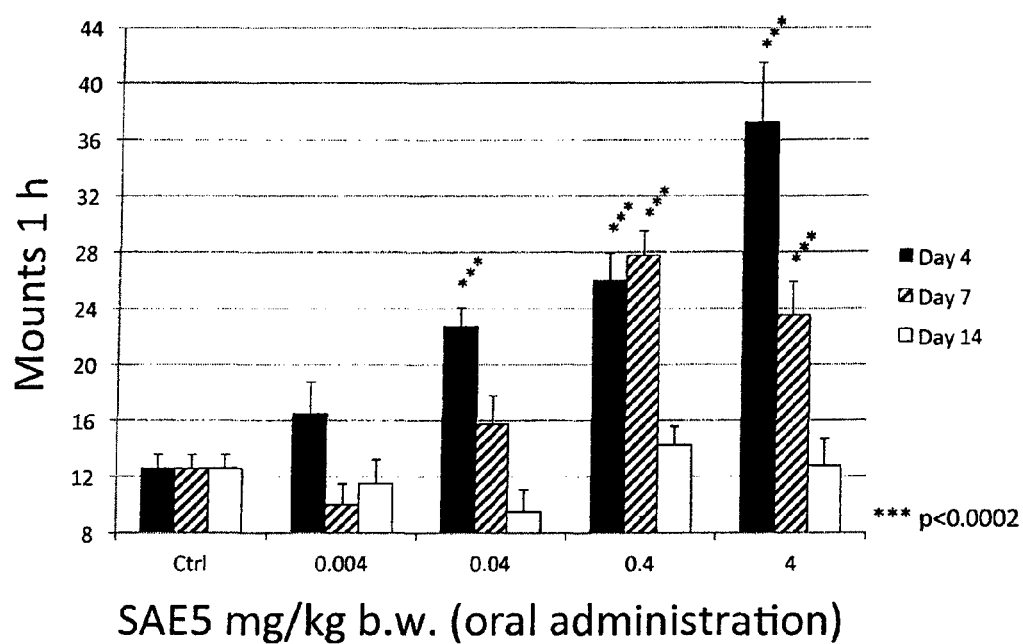

Results for GL-1203 are shown in FIG. 2, for SAE6 in FIG. 3 and For SAE5 in FIG. 4.

As seen from the Figures all compounds induced marked and highly significant dose-dependent increases in the number of mounts over the controls. The potency of GL-1203 was clearly less than for SAE6 and SAE5; for GL-1203 a clear and significant increase in the mounting frequency was seen only at the dose 4 mg/mg; for SAE6 and SAE5 clear and significant increases were seen already at the dose 0.04 mg/kg for both compounds, with even more significant effects being seen at the higher doses. The long duration of effect is also noteworthy both for SAE5 and SAE6; the duration being most sustained for SAE6.

Comparing SAE5 with SAE6 also shows a remarkable efficacy for oral SAE5 versus subcutaneous SAE6, as for the former the maximum number of mounts over the one hour observation period (at 4 mg/kg; D-4) amounted to the average 37 mounts while the maximum number of mounts for SAE6 (at 4 mg/kg; D-4) amounted to the average 23 mounts. The duration of the effect appeared to be more sustained for SAE6 than for SAE5, however.

From these data it can be computed that SAE6 and SAE5 and GL-1203 are sexually enhancing compounds as the effects at their effective doses onto the mounting frequence of male mice exceed a 50% increase in the number of mounts compared with the controls.

Example 6

Yield of Phragmalin Isolated from Seeds of *Chukrasia tabularis*

Extraction

Well-dried *Chukrasia tabularis* seeds (30 kg) (water content 6%) were purchased from a commercial *Chukrasia tabularis* tree plantation. 0.5 kg of the seeds were grinded and placed into a large round bottom flask with magnetic stirring. Chloroform ($CHCl_3$) (5 L) was added and the mixture was stirred at r.t. for 24 hours. The content was filtered through a glass pore filter into a round bottom flask. The materials remaining on the filter were washed twice with chloroform using 20 mL chloroform/5 g of seeds for each wash. The combined chloroform extract (SCE) was then evaporated, using a rotavapor at 25° C., which yielded an oily residue. From the total weight of the grinded seeds of 500 g, the oily residue amounted to 144.8 g.

First Flash Chromatography

This step was necessary for deoiling of SCE. Here one experiment is described in detail, as an example. Hexane (HEX) (40 mL) was added to a portion of the above oily residue, SCE (6.29 g), and the resulting emulsion was poured onto a column (18.3×3.3 cm) filled with silica gel (70-230 mesh, 60 Å, for column chromatography, Sigma-Aldrich, cat. 28, 862-4). 300 mL of HEX was then passed through the column; there-after increasing proportions of chloroform in HEX were applied; the ratios of HEX:chloroform (volume/volume) being varied from 20:1 to 1:20; in total 82 mL of HEX and 257 mL of chloroform was used. Finally 750 mL of chloroform was passed through the column. The total volume of solvents used for this step was 1554 mL, which amounted to 557 mL of HEX and 1007 mL of chloroform. Fractions of about 100 mL each were collected and analyzed by LC/MS, using a Perkin Elmer (PerkinElmer Life and Analytical Sciences, Boston, Mass., U.S.A.) PE SCIEX API 150EX instrument equipped with a turboionspray source using HPLC column packed with LiChrosorb RP18-5 (2.1 mm×100 mm, 5 µm); for elution a gradient was formed from water and acetonitrile (MeCN) (from 20% to 100% MeCN) with 5 mM ammonium acetate [$(NH_4)_2CO_3$] additive, at a flow rate of 0.2 mL/min during 15 min, and UV detection at 220 nm. Fractions 1-7 did not contain any ions; evaporation of these fractions yielded 5.79 g of vegetable oil. Fractions 8-11 contained the positive ions $(M+H)^+$ 701.4 (confirmed as being phragmalin 3,30-diisobutyrate) and 687.4, (confirmed as being phragmalin 3-isobutyrate-30-propionate). Fractions 12-15 contained the positive ions $(M+H)^+$ 736.4 (confirmed as being phragmalin 3-nicotinate-30-isobutyrate) and 794.4 (confirmed as being 12-alfa-acetoxyphragmalin 3-nicotinate-30-isobutyrate). Fractions 8-15 were combined and evaporated, yielding an oily residue.

After performing such flash chromatographies repeatedly, the entire 144.8 g SCE fraction obtained from 500 g of seeds yielded 96.2 g of plant oil, while after evaporation of the combined fractions 8-15 containing phragmalin derivatives, a total amount of 19.58 g (oily residue) was obtained.

Alkaline Hydrolysis

The procedure essentially according to Connolly J. D. at al., J. Chem. Soc., Perkin Trans. 1, 1978, 285-288, was used, as follows:

The combined oily residue from fractions 8-15 of the previous step was dissolved in 5% potassium hydroxide (KOH) in methanol (MeOH), using 10 mL/100 mg of the residue. The solution was refluxed for 0.5 h, then water was added and acidification using 3M hydrochloric acid (HO) to pH 3.5-4.0 was done. After evaporation of MeOH, the solution was diluted with water and MeCN until a ratio of MeCN/water 40:60 was achieved, and the materials were then lyophilized. The freeze-drying was carried out at 0.001 bar on a Beta 2-8 LD Freeze-Dryer (Martin Christ Gefriertrocknungsanlagen GmbH, Germany).

After freeze-drying the solid powder was obtained to which ethyl acetate (EtOAc) was added and the mixture was stirred for 4 h at r.t. This yielded a solution with a remainder of insoluble inorganic salts, which was filtered off using a glass pore filter. The filtrate was collected evaporated. From a total of 19.58 g of the starting material entered into the alkaline hydrolysis, 16.64 g of materials was obtained at the end of this step.

Second Flash Chromatography

This step was done in practically the same way as described in above under "First flash-chromatography". The collected fractions were analyzed using LC/MS essentially as described under "First flash chromatography", except that a gradient formed from 20% to 90% MeCN during 15 min was used. The fractions containing phragmalin were collected, combined and evaporated to dryness. Of the 16.64 g of the materials of the previous step applied to this step, plant oil (6.0 g) and the fractions enriched in phragmalin (9.43 g) was obtained.

HPLC

The 9.43 g of the enriched phragmalin containing mixture from the second flash chromatographic step was applied to repeated semi-preparative HPLC (high pressure liquid chromatography) purifications to obtain pure phragmalin. Here a single run is described, as an example. The mixture from the enriched phragmalin fraction of the second flash chromatographic step (30 mg) was dissolved in MeCN (0.9 mL), water (0.6 mL) was then added, the solution was centrifuged, and the supernatant was introduced into a semi preparative (10× 250 mm) HPLC column (filled with Lichrospher RP18, 10 µm; Merck KGaA, Germany) connected to a chromatograph (LKB, Sweden), consisting of a 2150 HPLC pump, 2152 LC controller, and 2151 variable wavelength monitor. Conditions: flow rate 5 mL/min, detection at 220 nm, eluent MeCN/water using a gradient from 30% to 50% MeCN. The fractions containing phragmalin were collected and analyzed by LC/MS (as mentioned above but with gradient from 20% to 90% MeCN during 15 min). All fractions containing phragmalin were collected and lyophilized.

The process of the previous paragraph was repeated until all the 9.43 g of the enriched phragmalin fraction had been applied; after lyophilization all runs combined gave 1.76 g of pure phragmalin; LC/MS indicated a mass (M+H)+ 561.3, (M−H)− 559.0; analytical HPLC indicated a purity of phragmalin more than 95%. HRMS (M+H)+: 561.2333, $C_{29}H_{37}O_{11}$ requires 561.2336. The identity of phragmalin was further confirmed with NMR, which was compliant with that the materials obtained is in fact phragmalin.

Thus from 500 g of *Chukrasia tabularis* seeds 1.76 g of pure phragmalin was obtained. Thus the content of phragmalin retrievable from these seeds amounts to 0.35% (i.e. 3.52 g/kg).

Example 7

HRMS

For the sake of the present patent compounds were characterized with High Resolution Mass Spectrometry (HRMS). Whenever HRMS is mentioned throughout this patent the compound was analyzed with a Q-T of 2 from Micromass (Macromass/Waters; Waters Corporation, 34 Maple Street, Milford Mass. 01757, USA) instrument was used. This is a high-resolution hybrid quadrupole time-of-flight mass spectrometer, equipped with Z-spray electrospray ionization inlet (i.e., the Micromass nanoflow interface with a glass capillary option was used). The spectrum was observed in positive ESI mode. Capillary voltage was 1.22 kV, cone voltage was 38.5 V, and source temperature was at 80° C.

For the assays a sample of the test compound was dissolved in 50% acetonitrile/water with 0.2% formic acid. To compensate for instrument drift a substance with well-known mass was used as the internal lock mass. To obtain responses of similar intensity a sample of reference substance was prepared with the same solvent and concentration.

Example 8

Synthesis of Compounds of Structure (2b) Starting from Phragmalin

Scheme 4

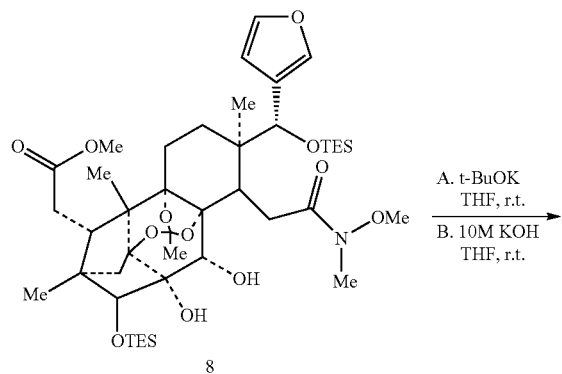

8

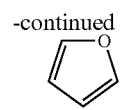
-continued

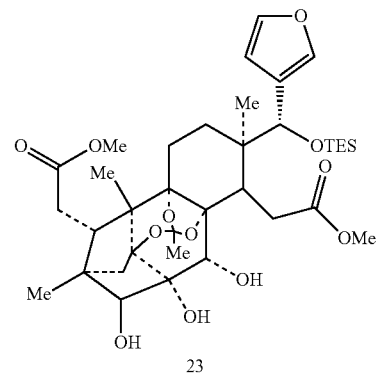

A summary of the steps is shown in Scheme 4.

Compound 22 (AJ-2095)

Method A:

To a solution of compound 8 (10 mg, 0.012 mmol) (prepared from phragmalin as detailed in Example 1) in tetrahydrofuran (THF) (2 mL), potassium tert-butoxide (t-BuOK) (1.35 mg, 0.012 mmol) was slowly added at stirring. The mixture was stirred at room temperature (r.t.) for 24 h and to this aqueous 5% potassium bisulfate (KHSO$_4$) (8 mL) was added. The mixture was extracted with ethyl acetate (EtOAc) (3×10 mL), the combined organic phase was dried over Na$_2$SO$_4$, filtered and then evaporated. The residue was purified by preparative thin layer chromatography (TLC) on silica gel, eluting with a mixture of light petroleum ether and EtOAc (1:1) to give compound 22 as colorless oil.

Note: The reaction was repeated three additional times with variations of equivalents of t-BuOK from 1 to 5, starting with between 5-26 mg of compound 8 and using reaction times between 7 h to 24 hours at r.t.; the yield of compound 22 reaching maximally 51%.

Method B:

To a solution of compound 8 (40 mg, 0.048 mmol) in THF (4 mL) 10 M aqueous potassium hydroxide (KOH) (24.5 µl, 0.24 mmol) was added. The mixture was stirred at room r.t. for 24 h and to this aqueous 5% KHSO$_4$ (10 mL) was then added. The mixture was extracted with EtOAc (3×10 mL), the combined organic phase was dried over Na$_2$SO$_4$, filtered and evaporated. The residue was purified by preparative TLC on silica gel, eluting with a mixture of light petroleum ether and EtOAc (1:1) to give compound 22 as colorless oil.

Note 1: The procedure was repeated four additional times starting with 34-44 mg of compound 8, however with variations of the amount of 10 M aqueous KOH from 5 to 15 equivalents, with yields of compound 22 40-53%.

Note 2: Using of 0.1 M aqueous NaOH (1.1 equivalent) in THF at r.t. for 7 days was also successful, but the exchange of THF to MeOH did not result in the desired product 22. Using of sodium hydride (NaH) (1.2 equivalent) in diethyl ether at r.t. for 16 h was also successful, but the exchange of NaH to lithium diisopropylamide (LDA) did not result in the desired product 22, as well as using of 1,8-diazobicyclo[5,4,0]-undec-7-ene (DBD) (1 equivalent) in chloroform (CHCl$_3$) at r.t. for 16 h was unsuccessful.

HRMS (M+H)$^+$: 693.3315, $C_{35}H_{53}O_{12}Si$ requires 693.3306.

$^1$H-NMR (CDCl$_3$, TMS): 0.51 (6H, q, 7.8 Hz); 0.88 (9H, q, 7.8 Hz); 0.99 (3H, s); 1.09 (3H, s); 1.16 (3H, s); 1.2-1.3 (1H, m); 1.49-1.64 (3H, m); 1.55 (3H, s); 1.76-1.80 (1H, m); 1.82 (1H, d, 10.6 Hz); 2.18 (1H, dd, 16.0 and 3.5 Hz); 2.23 (1H, dd, 10.2 and 3.1 Hz); 2.38 (1H, dd, 16.0 and 9.7 Hz); 2.56 (1H, br s); 2.89 (1H, dd, 10.2 and 2.3 Hz); 2.99 (1H, dd, 16.0 and 3.5 Hz); 3.08 (1H, br s); 3.39 (1H, dd, 15.7 and 10.2 Hz); 3.58 (1H, s); 3.61 (3H, s); 4.63 (1H, br s); 5.21 (1H, s); 6.42 (1H, s); 7.33 (1H, s) and 7.39 ppm (1H, s).

Compound 23 (AJ-2097A)

Method A:

To a solution of compound 22 (10 mg, 0.014 mmol) in diethyl ether (3 mL) a freshly prepared solution of diazomethane in diethyl ether (from Diazald; N-methyl-N-nitroso-p-toluenesulfonamide) (3.5 mL, 0.015 mmol) was dropwise added at −78° C. The mixture was stirred at −78° C. for 2 h and then at r.t. for 24 h and then evaporated. The residue was purified by radial chromatography on silica gel eluting with a mixture of light petroleum ether and EtOAc (2:1) to give compound 23 (7.7 mg, 93%) as colorless oil.

Method B:

To a solution of compound 22 (10 mg, 0.014 mmol) in N,N-dimethylformamide (DMF) ((2 mL), methyl iodide (iodomethane, CH$_3$I) (2.7 μL, 0.043 mmol) was added and after that 20% methanolic solution of tetramethylammonium hydroxide (TMAH) (7.9 μL, 0.017 mmol) was introduced. The reaction mixture was stirred at r.t. for 24 h. To the reaction mixture water (10 mL) was added and the product was taken up into EtOAc (15 mL). The aqueous phase was separated and the organic phase was washed with water (3×10 mL) and dried over Na$_2$SO$_4$. The solution was evaporated in vacuo and the residue was purified by flash chromatography on silica gel, eluting with a mixture of light petroleum ether and EtOAc (2:1) to give compound 23 (8.8 mg, 85%) as colorless oil.

HRMS (M+H)$^+$: 707.3456, $C_{36}H_{55}O_{12}Si$ requires 707.3463.

$^1$H-NMR (CDCl$_3$, TMS): 0.49 (6H, q, 7.8 Hz); 0.87 (9H, q, 7.8 Hz); 0.98 (3H, s); 1.08 (3H, s); 1.16 (3H, s); 1.2-1.3 (1H, m); 1.53-1.64 (2H, m); 1.54 (1H, d, 10.9 Hz); 1.55 (3H, s); 1.76-1.80 (1H, m); 1.80 (1H, d, 10.7 Hz); 2.18 (1H, dd, 16.0 and 3.5 Hz); 2.23 (1H, dd, 10.0 and 3.1 Hz); 2.37 (1H, dd, 16.0 and 9.7 Hz); 2.42 (1H, br s); 2.87-2.92 (3H, m); 3.35 (1H, dd, 15.7 and 10.1 Hz); 3.38 (1H, br s); 3.57 (1H, s); 3.60 (3H, s); 3.63 (3H, s); 4.59 (1H, d, 7.8 Hz); 5.19 (1H, s); 6.41 (1H, s); 7.31 (1H, s) and 7.37 ppm (1H, s).

$^{13}$C-NMR (CDCl$_3$, TMS): 5.0, 7.0; 14.6; 15.7; 20.5; 20.7; 25.6; 31.4; 34.1; 35.5; 39.6; 40.1; 45.3; 45.8; 47.2; 51.4; 51.9; 69.3; 69.8; 78.6; 83.7; 84.1; 87.0; 88.30; 110.7; 118.6; 126.7; 140.5; 142.2 173.2 and 176.1 ppm.

Overall Yields of 22 and 23 from Phragmalin

| Step | Maximum yield % (fraction) |
|---|---|
| Compound 6 → Compound 7 (Example 1) | 45% (0.45) |
| Compound 7 → Compound 8 (Example 1) | 70% (0.70) |
| Compound 8 → Compound 22 (Method B) | 53% (0.28) |
| Compound 22 → Compound 23 (Method A) | 93% (0.92) |

Overall yields for 22 and 23 starting from phragmalin:

Yield of 22: 0.45×0.70×0.53=0.1670 (16.7%)

Yield of 23: 0.45×0.70×0.53×0.93=0.1543 (15.43%)

Example 9

Pharmaceutical Compositions

Composition of SAE5 for oral use:

| SAE5 | 200 mg |
|---|---|
| Cocoa butter melted at 55° C. | 10 mL |

The SAE5 is placed in the heated cocoa butter under gentle stirring until all SAE5 has become dissolved. 1 mL of the solution is then dispensed into gelatin capsules and the cocoa is allowed to solidify. The capsules are thereafter caped.

Composition of LG-1725 for Subcutaneous Injection:

| LG-1725 | 15 mg |
|---|---|
| Cotton oil | ad 1 mL |

LEGENDS TO THE FIGURES

FIG. 1: Aggression inducing effect of 0.4 mg/kg of LG-1725 (LG1725)×3 adminstered sub-cutaneously for three consecutive days to male mice. The number of aggressive attacks directed to a female mouse was then assessed on day 4, 7, and 14, following the start of administration of LG-1725. Ctrl=control; i.e. sham operated.

FIG. 2: Sexually enhancing effect of 0.04-4 mg/kg GL-1203×3 adminstered for three consecutive days to male mice. The number of mounts to female mice was then assessed on day 4, 7 and 14 following the start of administration of GL-1203.

FIG. 3: Sexually enhancing effect of 0.004-4 mg/kg SAE6×3 administered sub-cutaneously for three consecutive days to male mice. The number of mounts to female mice was then assessed on day 4, 7 and 14 following the start of administration of SAE6.

FIG. 4: Sexually enhancing effect of 0.004-4 mg/kg SAE5×3 administered per orally for three consecutive days to male mice. The number of mounts to female mice was then assessed on day 4, 7 and 14 following the start of administration of SAE5.

FIG. 5: HPLC profile of an LG-1725 preparation, showing LG-1725 to be essentially pure.

FIG. 6: HPLC profile of an SAE5 preparation, showing SAE5 to be essentially pure.

The invention claimed is:

1. A compound according to structure (4gg) or (4hh):

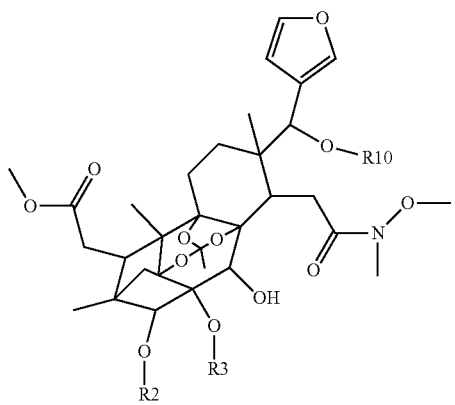
(4gg)

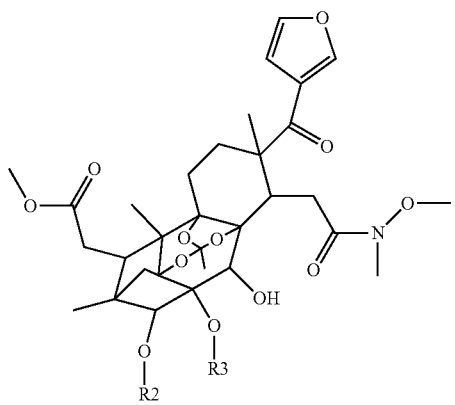
(4hh)

wherein R2 is any one of hydrogen, acetyl, isobutyryl or triethylsilyl (TES) or

R2 is —C(O)alkyl, where alkyl is from C1-C6 unbranched or branched, saturated or unsaturated hydrocarbyl group that may be unsubstituted or substituted with one or more halogen atoms, or R2 is —C(O)cycloalkyl, where cycloalkyl is saturated C3-C6 cycloalkyl hydrocarbyl group that may be unsubstituted or substituted with one or more halogen atoms, or R2 is triethylsilyl or tert-butyldimethylsilyl;

wherein R3 is any one of hydrogen, acetyl, or isobutyryl, or

R3 is —C(O)alkyl, where alkyl is from C1-C6 unbranched or branched, saturated or unsaturated hydrocarbyl group that may be unsubstituted or substituted with one or more halogen atoms, or R3 is —C(O)cycloalkyl, where cycloalkyl is saturated C3-C6 cycloalkyl hydrocarbyl group that may be unsubstituted or substituted with one or more halogen atoms;

and wherein R10 is any one of hydrogen, acetyl, trifluoroacetyl or triethylsilyl (TES); or R10 is —C(O)alkyl, where alkyl is from C1-O6 unbranched or branched, saturated or unsaturated hydrocarbyl group that may be unsubstituted or substituted with one or more halogen atoms, or R10 is —C(O)cycloalkyl, where cycloalkyl is saturated C3-6 cycloalkyl hydrocarbyl group that may be unsubstituted or substituted with one or more halogen atoms, or R10 is triethylsilyl or tert-butyldimethylsilyl.

* * * * *